US010792296B2

(12) United States Patent
Ray, II

(10) Patent No.: US 10,792,296 B2
(45) Date of Patent: *Oct. 6, 2020

(54) COMPOSITIONS AND METHODS FOR TREATING AN INFECTION

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/594,814

(22) Filed: Oct. 7, 2019

(65) Prior Publication Data

US 2020/0030354 A1 Jan. 30, 2020

Related U.S. Application Data

(63) Continuation of application No. 16/167,073, filed on Oct. 22, 2018, now Pat. No. 10,434,115, which is a continuation of application No. 15/602,395, filed on May 23, 2017, now Pat. No. 10,105,381.

(60) Provisional application No. 62/340,417, filed on May 23, 2016.

(51) Int. Cl.
| *A61K 31/7056* | (2006.01) |
| *A61K 9/00* | (2006.01) |
| *A61K 31/351* | (2006.01) |
| *A61K 31/4174* | (2006.01) |
| *A61K 31/573* | (2006.01) |
| *A61K 9/48* | (2006.01) |
| *A61K 9/14* | (2006.01) |
| *A61K 45/06* | (2006.01) |
| *A61K 47/02* | (2006.01) |
| *A61K 47/12* | (2006.01) |

(52) U.S. Cl.
CPC ........ *A61K 31/7056* (2013.01); *A61K 9/0014* (2013.01); *A61K 9/0046* (2013.01); *A61K 9/14* (2013.01); *A61K 9/48* (2013.01); *A61K 9/4858* (2013.01); *A61K 31/351* (2013.01); *A61K 31/4174* (2013.01); *A61K 31/573* (2013.01); *A61K 45/06* (2013.01); *A61K 47/02* (2013.01); *A61K 47/12* (2013.01)

(58) Field of Classification Search
None
See application file for complete search history.

(56) References Cited

U.S. PATENT DOCUMENTS

2005/0058725 A1* 3/2005 McKearn ............. A61K 31/135
424/687

* cited by examiner

*Primary Examiner* — Po-Chih Chen
(74) *Attorney, Agent, or Firm* — Akerman LLP

(57) ABSTRACT

A dry formulation may include one or more active agents including one or more anti-infective agents such as an anti-bacterial agent, anti-fungal agent, or other anti-active agent. The dry formulation may be prepared for administration by mixing the dry formulation with a diluent. In one example, the diluent is a hydrocortisone and acetic acid solution or a sodium chloride solution. The combined preparation may be administered to the ear or skin to treat or prevent an infection.

10 Claims, No Drawings

COMPOSITIONS AND METHODS FOR TREATING AN INFECTION

CROSS-REFERENCE TO RELATED APPLICATIONS

The present application is a continuation application of U.S. patent application Ser. No. 16/167,073, filed Oct. 22, 2018, now U.S. Pat. No. 10,434,115, which is a continuation of U.S. patent application Ser. No. 15/602,395, filed May 23, 2017, now U.S. Pat. No. 10,105,381, which claims priority to U.S. Provisional Patent Application No. 62/340,417, filed 23 May 2016. U.S. patent application Ser. No. 16/167,073, U.S. patent application Ser. No. 15/602,395, and U.S. Provisional Patent Application No. 62/340,417 are hereby incorporated herein by reference.

BACKGROUND

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection.

Despite advances in the understanding of the pathology of bacterial infections and fungal infections, there is still a need for compositions and methods that efficiently treat or prevent the progression and reoccurrence of bacterial infections and fungal infections that affect the skin, the ears, or the feet.

BRIEF SUMMARY

Disclosed herein is a dry formulation comprising a therapeutically effective amount of mupirocin, a therapeutically effective amount of an anti-bacterial agent, and a therapeutically effective amount of an anti-fungal agent.

Disclosed herein is a dry formulation comprising a therapeutically effective amount of mupirocin, a therapeutically effective amount of an anti-bacterial agent, a therapeutically effective amount of an anti-fungal agent, a sufficient amount of an excipient base powder, and a sufficient amount of xylitol.

Disclosed herein is a dry formulation comprising a therapeutically effective amount of mupirocin, a therapeutically effective amount of clindamycin hydrochloride, and a therapeutically effective amount of clotrimazole.

Disclosed herein is a dry formulation comprising a therapeutically effective amount of mupirocin, a therapeutically effective amount of clindamycin hydrochloride, a therapeutically effective amount of clotrimazole, a sufficient amount of an excipient base powder, and a sufficient amount of xylitol.

Disclosed herein is a dry formulation comprising a therapeutically effective amount of mupirocin, a therapeutically effective amount of a corticosteroid or a pharmaceutically acceptable salt thereof, and a therapeutically effective amount of an anti-fungal agent.

Disclosed herein is a dry formulation comprising a therapeutically effective amount of mupirocin, a therapeutically effective amount of a corticosteroid or a pharmaceutically acceptable salt thereof, a therapeutically effective amount of an anti-fungal agent, a sufficient amount of an excipient base powder, and a sufficient amount of xylitol.

Disclosed herein is a dry formulation comprising a therapeutically effective amount of mupirocin, a therapeutically effective amount of betamethasone sodium phosphate, and a therapeutically effective amount of clotrimazole.

Disclosed herein is a dry formulation comprising a therapeutically effective amount of mupirocin, a therapeutically effective amount of betamethasone sodium phosphate, a therapeutically effective amount of clotrimazole, a sufficient amount of an excipient base powder, and a sufficient amount of xylitol.

Disclosed herein is a dry formulation comprising a therapeutically effective amount of clotrimazole, a sufficient amount of an excipient base powder, and a sufficient amount of xylitol.

Disclosed herein is a dry formulation comprising a therapeutically effective amount of clotrimazole, a sufficient amount of an excipient base powder, a sufficient amount of xylitol, and a therapeutically effective amount of ceftriaxone.

Disclosed herein is a dry formulation comprising a therapeutically effective amount of clotrimazole, a therapeutically effective amount of a corticosteroid or a pharmaceutically acceptable salt thereof, a sufficient amount of an excipient base powder, and a sufficient amount of xylitol.

Disclosed herein is a dry formulation comprising a therapeutically effective amount of clotrimazole, a therapeutically effective amount of betamethasone sodium phosphate, a sufficient amount of an excipient base powder, and a sufficient amount of xylitol.

Disclosed herein is a dry formulation comprising a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent.

Disclosed herein is a dry formulation comprising a therapeutically effective amount of doxycycline or a pharmaceutically acceptable salt thereof, a therapeutically effective amount of an corticosteroid or a pharmaceutically acceptable salt thereof, a therapeutically effective amount of clotrimazole, a sufficient amount of an excipient base powder, and a sufficient amount of xylitol.

Disclosed herein is a dry formulation comprising a therapeutically effective amount of doxycycline hyclate, a therapeutically effective amount of betamethasone sodium phosphate, a therapeutically effective amount of clotrimazole, a sufficient amount of an excipient base powder, and a sufficient amount of xylitol.

Disclosed herein is a dry formulation comprising a therapeutically effective amount of doxycycline hyclate, a therapeutically effective amount of dexamethasone, and a therapeutically effective amount of clotrimazole.

Disclosed herein is a dry formulation comprising a therapeutically effective amount of doxycycline hyclate, a therapeutically effective amount of a dexamethasone, a therapeutically effective amount of clotrimazole, a sufficient amount of an excipient base powder and a sufficient amount of xylitol.

Disclosed herein is a dry formulation comprising a therapeutically effective amount of azithromycin, a therapeutically effective amount of fluticasone, and a therapeutically effective amount of fluconazole.

Disclosed herein is a dry formulation comprising a therapeutically effective amount of azithromycin, a therapeutically effective amount of fluticasone, a therapeutically effective amount of fluconazole, a sufficient amount of an excipient base powder, and a sufficient amount of xylitol.

Disclosed herein is a dry formulation comprising a therapeutically effective amount of sulfamethoxazole, a therapeutically effective amount of trimethoprim, a therapeutically effective amount of fluticasone, and a therapeutically effective amount of fluconazole.

Disclosed herein is a dry formulation comprising a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol.

Disclosed herein is a dry formulation comprising a therapeutically effective amount of levofloxacin hemihydrate, a therapeutically effective amount of fluticasone, and a therapeutically effective amount of fluconazole.

Disclosed herein is a dry formulation comprising a therapeutically effective amount of levofloxacin hemihydrate, a therapeutically effective amount of fluticasone, a therapeutically effective amount of fluconazole, a sufficient amount of an excipient base powder, and a sufficient amount of xylitol.

Disclosed herein is a dry formulation comprising a therapeutically effective amount of fluticasone and a therapeutically effective amount of fluconazole.

Disclosed herein is a dry formulation comprising a therapeutically effective amount of fluticasone, a therapeutically effective amount of fluconazole, a sufficient amount of an excipient base powder, and a sufficient amount of xylitol.

Disclosed herein is a dry formulation comprising a therapeutically effective amount of vancomycin hydrochloride and a therapeutically effective amount of mupirocin.

Disclosed herein is a dry formulation comprising a therapeutically effective amount of vancomycin hydrochloride, a therapeutically effective amount of mupirocin, a sufficient amount of an excipient base powder, and a sufficient amount of xylitol.

Disclosed herein is a dry formulation comprising a therapeutically effective amount of mupirocin and a therapeutically effective amount of clotrimazole.

Disclosed herein is a dry formulation comprising a therapeutically effective amount of mupirocin, a therapeutically effective amount of clotrimazole, a sufficient amount of an excipient base powder, and a sufficient amount of xylitol.

Disclosed herein is a dry formulation comprising a therapeutically effective amount of mupirocin, a therapeutically effective amount of clindamycin, and a therapeutically effective amount of clotrimazole.

Disclosed herein is a dry formulation comprising a therapeutically effective amount of mupirocin, a therapeutically effective amount of clindamycin, and a therapeutically effective amount of clotrimazole, a sufficient amount of an excipient base powder, and a sufficient amount of xylitol.

Disclosed herein is a dry formulation comprising a therapeutically effective amount of ceftriaxone.

Disclosed herein is a dry formulation comprising a therapeutically effective amount of ceftriaxone, a sufficient amount of an excipient base powder, and a sufficient amount of xylitol.

Disclosed herein is a dry formulation comprising a therapeutically effective amount of clotrimazole.

Disclosed herein is a dry formulation comprising a therapeutically effective amount of clotrimazole, a sufficient amount of an excipient base powder, and a sufficient amount of xylitol.

Disclosed herein is a dry formulation comprising a therapeutically effective amount of doxycycline or a pharmaceutically acceptable salt thereof and a therapeutically effective amount of clotrimazole.

Disclosed herein is a dry formulation comprising a therapeutically effective amount of doxycycline or a pharmaceutically acceptable salt thereof, a therapeutically effective amount of clotrimazole, a sufficient amount of an excipient base powder, and a sufficient amount of xylitol.

Disclosed herein are compounded compositions for treating an infection. Disclosed herein are compounded compositions for treating an infection comprising a diluent and a disclosed dry formulation, e.g., any of the above dry formulations or dry formulations disclosed elsewhere herein.

Disclosed herein is a capsule comprising a disclosed dry formulation. Disclosed herein is a container comprising a disclosed dry formulation. Disclosed herein is a kit comprising a disclosed dry formulation. Disclosed herein is a kit comprising a plurality of containers, each comprising a disclosed dry formulation. Disclosed herein is a kit comprising a plurality of containers, each comprising a disclosed dry formulation, and instructions for using the dry formulation.

Disclosed herein are methods of making a disclosed dry formulation.

In one example, the method of making a dry formulation may comprise mixing a therapeutically effective amount of mupirocin, a therapeutically effective amount of an anti-bacterial agent, and a therapeutically effective amount of an anti-fungal agent to make a homogenous dry formulation.

In another example, the method of making a dry formulation may comprise mixing a therapeutically effective amount of mupirocin, a therapeutically effective amount of an anti-bacterial agent, a therapeutically effective amount of an anti-fungal agent, a sufficient amount of an excipient base powder, and a sufficient amount of xylitol to make a homogenous dry formulation.

In yet another example, the method of making a dry formulation may comprise mixing a therapeutically effective amount of mupirocin, a therapeutically effective amount of clindamycin hydrochloride, and a therapeutically effective amount of clotrimazole to make a homogenous dry formulation.

In still another example, the method of making a dry formulation may comprise mixing a therapeutically effective amount of mupirocin, a therapeutically effective amount of clindamycin hydrochloride, a therapeutically effective amount of clotrimazole, a sufficient amount of an excipient base powder, and a sufficient amount of xylitol to make a homogenous dry formulation.

In still yet another example, the method of making a dry formulation may comprise mixing a therapeutically effective amount of mupirocin, a therapeutically effective amount of a corticosteroid or a pharmaceutically acceptable salt thereof, and a therapeutically effective amount of an anti-fungal agent to make a homogenous dry formulation.

In another example, the method of making a dry formulation may comprise mixing a therapeutically effective amount of mupirocin, a therapeutically effective amount of a corticosteroid or a pharmaceutically acceptable salt thereof, and a therapeutically effective amount of an anti-fungal agent, a sufficient amount of an excipient base powder, and a sufficient amount of xylitol to make a homogenous dry formulation.

In still another example, the method of making a dry formulation may comprise mixing a therapeutically effective amount of mupirocin, a therapeutically effective amount of a betamethasone sodium phosphate, and a therapeutically effective amount of clotrimazole to make a homogenous dry formulation.

In yet another example, the method of making a dry formulation may comprise mixing a therapeutically effective amount of mupirocin, a therapeutically effective amount of betamethasone sodium phosphate, a therapeutically effective amount of clotrimazole to make a homogenous dry formulation, a sufficient amount of excipient base powder, and a sufficient amount of xylitol.

In still yet another example, the method of making a dry formulation may comprise mixing a therapeutically effective amount of clotrimazole, a sufficient amount of an excipient base powder, and a sufficient amount of xylitol to make a homogenous dry formulation.

In another example, the method of making a dry formulation may comprise mixing a therapeutically effective amount of clotrimazole, a therapeutically effective amount of a corticosteroid or a pharmaceutically acceptable salt thereof, a sufficient amount of an excipient base powder, and a sufficient amount of xylitol to make a homogenous dry formulation.

In still another example, the method of making a dry formulation may comprise mixing a therapeutically effective amount of clotrimazole, a therapeutically effective amount of a betamethasone sodium phosphate, a sufficient amount of an excipient base powder, and a sufficient amount of xylitol to make a homogenous dry formulation.

In yet another example, the method of making a dry formulation may comprise mixing a therapeutically effective amount of doxycycline or pharmaceutically acceptable salt thereof, a therapeutically effective amount of a corticosteroid or a pharmaceutically acceptable salt thereof, and a therapeutically effective amount of clotrimazole to make a homogenous dry formulation.

In still yet another example, the method of making a dry formulation may comprise mixing a therapeutically effective amount of doxycycline or pharmaceutically acceptable salt thereof, a therapeutically effective amount of a corticosteroid or a pharmaceutically acceptable salt thereof, a therapeutically effective amount of an clotrimazole, a sufficient amount of an excipient base powder, and a sufficient amount of xylitol to make a homogenous dry formulation.

In another example, the method of making a dry formulation may comprise mixing a therapeutically effective amount of doxycycline hyclate, a therapeutically effective amount of a betamethasone sodium phosphate, and a therapeutically effective amount of clotrimazole to make a homogenous dry formulation.

In still another example, the method of making a dry formulation may comprise mixing a therapeutically effective amount of doxycycline hyclate, a therapeutically effective amount of betamethasone sodium phosphate, a therapeutically effective amount of an clotrimazole, a sufficient amount of an excipient base powder, and a sufficient amount of xylitol to make a homogenous dry formulation.

In yet another example, the method of making a dry formulation may comprise mixing a therapeutically effective amount of doxycycline hyclate, a therapeutically effective amount of a dexamethasone, and a therapeutically effective amount of clotrimazole to make a homogenous dry formulation.

In still yet another example, the method of making a dry formulation may comprise mixing a therapeutically effective amount of doxycycline hyclate, a therapeutically effective amount of dexamethasone, a therapeutically effective amount of an clotrimazole, a sufficient amount of an excipient base powder, and a sufficient amount of xylitol to make a homogenous dry formulation.

In another example, the method of making a dry formulation may comprise mixing a therapeutically effective amount of azithromycin, a therapeutically effective amount of fluticasone, and a therapeutically effective amount of fluconazole to make a homogenous dry formulation.

In still another example, the method of making a dry formulation may comprise mixing a therapeutically effective amount of azithromycin, a therapeutically effective amount of fluticasone, a therapeutically effective amount of fluconazole, a sufficient amount of an excipient base powder, and a sufficient amount of xylitol to make a homogenous dry formulation.

In yet another example, the method of making a dry formulation may comprise mixing a therapeutically effective amount of sulfamethoxazole, a therapeutically effective amount of trimethoprim, a therapeutically effective amount of fluticasone, and a therapeutically effective amount of fluconazole to make a homogenous dry formulation.

In still yet another example, the method of making a dry formulation may comprise mixing a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol to make a homogenous dry formulation.

In another example, the method of making a dry formulation may comprise mixing a therapeutically effective amount of levofloxacin hemihydrate, a therapeutically effective amount of fluticasone, and a therapeutically effective amount of fluconazole to make a homogenous dry formulation.

In still another example, the method of making a dry formulation may comprise mixing a therapeutically effective amount of levofloxacin hemihydrate, a therapeutically effective amount of fluticasone, a therapeutically effective amount of fluconazole, a sufficient amount of an excipient base powder, and a sufficient amount of xylitol to make a homogenous dry formulation.

In yet another example, the method of making a dry formulation may comprise mixing a therapeutically effective amount of fluticasone and a therapeutically effective amount of fluconazole to make a homogenous dry formulation.

In yet still another example, the method of making a dry formulation may comprise mixing a therapeutically effective amount of fluticasone, a therapeutically effective amount of fluconazole, a sufficient amount of an excipient base powder, and a sufficient amount of xylitol to make a homogenous dry formulation.

In another example, the method of making a dry formulation may comprise mixing a therapeutically effective amount of vancomycin hydrochloride and a therapeutically effective amount of mupirocin to make a homogenous dry formulation.

In still another example, the method of making a dry formulation may comprise mixing a therapeutically effective amount of vancomycin hydrochloride, a therapeutically effective amount of mupirocin, a sufficient amount of an excipient base powder, and a sufficient amount of xylitol to make a homogenous dry formulation.

In yet another example, the method of making a dry formulation may comprise mixing a therapeutically effective amount of mupirocin and a therapeutically effective amount of clotrimazole to make a homogenous dry formulation.

In still yet another example, the method of making a dry formulation may comprise mixing a therapeutically effective amount of mupirocin and a therapeutically effective amount of clotrimazole, a sufficient amount of an excipient base powder, and a sufficient amount of xylitol to make a homogenous dry formulation.

In another example, the method of making a dry formulation may comprise mixing a therapeutically effective amount of mupirocin, a therapeutically effective amount of clindamycin, and a therapeutically effective amount of clotrimazole to make a homogenous dry formulation.

In still another example, the method of making a dry formulation may comprise mixing a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol to make a homogenous dry formulation.

In yet another example, the method of making a dry formulation may comprise mixing a therapeutically effective amount of ceftriaxone, a sufficient amount of an excipient base powder, and a sufficient amount of xylitol to make a homogenous dry formulation.

In still yet another example, the method of making a dry formulation may comprise mixing a therapeutically effective amount of clotrimazole to make a homogenous dry formulation.

In another example, the method of making a dry formulation may comprise mixing a therapeutically effective amount of clotrimazole, a sufficient amount of an excipient base powder, and a sufficient amount of xylitol to make a homogenous dry formulation.

In still another example, the method of making a dry formulation may comprise mixing a therapeutically effective amount of doxycycline or a pharmaceutically acceptable salt thereof and a therapeutically effective amount of clotrimazole to make a homogenous dry formulation.

In yet another example, the method of making a dry formulation may comprise mixing a therapeutically effective amount of doxycycline or a pharmaceutically acceptable salt thereof, a therapeutically effective amount of clotrimazole, a sufficient amount of an excipient base powder, and a sufficient amount of xylitol to make a homogenous dry formulation.

Also disclosed herein is a method of making a compounded composition comprising mixing any dry formulation disclosed herein with a diluent to generate a homogenous compounded composition.

Disclosed herein are also methods of treatment.

In one example, a method of treating or preventing an ear infection may comprise administering to an affected ear of a subject a compounded composition, wherein the compounded composition comprises a disclosed dry formulation mixed with a diluent. In another example, the method of treating or preventing an ear infection may comprise (i) preparing a homogenous compounded composition, wherein the compounded composition comprises a disclosed dry formulation mixed with a diluent, and (ii) administering to an affected ear of a subject the compounded composition.

In another example, a method of treating or preventing a skin infection may comprise applying to the skin of a subject a compounded composition, wherein the compounded composition comprises a disclosed dry formulation mixed with a diluent. In another example the method of treating or preventing a skin infection may comprise (i) preparing a homogenous compounded composition, wherein the compounded composition comprises a dry formulation mixed with a diluent; and (ii) applying the compounded composition to the skin of the subject.

In another example, a method of treating or preventing a foot infection may comprise (i) adding a dry formulation to water contained within a foot bath; (ii) adding a diluent to the water contained within the foot bath; (iii) agitating the water contained within the foot bath; and (iv) contacting the agitated water with at least a part of one or both feet of a subject.

In another example, the method of treating or preventing a foot infection may comprise (i) agitating water contained within a foot bath; (ii) adding a dry formulation to the water contained with the foot bath; (iii) adding a diluent to the water contained within the foot bath; and (iv) contacting the agitated water with at least a part of one or both feet of a subject.

In still another example, the method of treating or preventing a foot infection may comprise (i) mixing a dry formulation with a diluent to create a compounded composition; (ii) adding the compounded composition to the water contained within the foot bath; (iii) agitating the water contained within the foot bath; and (iv) contacting the agitated water with at least part of one or both feet of a subject.

In yet another example, the method of treating or preventing a foot infection may comprise (i) mixing a dry formulation with a diluent to create a compounded composition; (ii) agitating water contained within a foot bath; (iii) adding the compounded composition to the water contained within the foot bath; and (iv) contacting the agitated water with at least part of one or both feet of a subject.

In still yet another example, the method of treating or preventing a foot infection may comprise (i) adding a dry formulation to water contained within a foot bath; (ii) adding a diluent to the water contained within the foot bath; (iii) agitating the water contained within the foot bath; and (iv) contacting the agitated water with at least a part of one or both feet of a subject.

In another example, the method of treating or preventing a foot infection may comprise (i) agitating water contained within a foot bath; (ii) adding a dry formulation to the water contained with the foot bath; (iii) adding a diluent to the water contained within the foot bath; and (iv) contacting the agitated water with at least a part of one or both feet of a subject.

In still another example, the method of treating or preventing a foot infection may comprise (i) adding a dry formulation to water contained within a foot bath; (ii) agitating the water contained within the foot bath; and (iii) contacting the agitated water with at least a part of one or both feet of a subject.

In yet another example, the method of treating or preventing a foot infection may comprise (i) agitating water contained within a foot bath; (ii) adding a dry formulation to the water contained with the foot bath; and (iii) contacting the agitated water with at least a part of one or both feet of a subject.

DETAILED DESCRIPTION

The present disclosure describes dry formulations, compounded compositions, kits, capsules, containers, and/or methods thereof. It is to be understood that the inventive aspects of which are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method. The phrase "consisting of" excludes any component, step, or element that is not recited in the claim. The phrase "comprising" is synonymous with "including", "containing", or "characterized by", and is inclusive or open-ended. "Comprising" does not exclude additional, unrecited components or steps.

As used herein, when referring to any numerical value, the term "about" means a value falling within a range that is ±10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. In an aspect, a disclosed method can optionally comprise one or more additional steps, such as, for example, repeating an administering step or altering an administering step.

As used herein, the term "subject" refers to the target of administration, e.g., a human being. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and child subjects, as well as fetuses, whether male or female, are intended to be covered. In an aspect, a subject can be a human patient. In an aspect, the subject can have diabetes, can be obese, can be immunocompromised, can be non-ambulatory, or can have poor blood flow, or a combination thereof. In an aspect, the subject can routinely wear thick socks or wear heavy boots.

A subject can have a bacterial infection, be suspected of having a bacterial infection, or be at risk of developing a bacterial infection. A subject can have a fungal infection, be suspected of having a fungal infection, or be at risk of developing a fungal infection. A subject can have a bacterial infection and a fungal infection, be suspected of having a bacterial infection and a fungal infection, or be at risk of developing a bacterial infection and a fungal infection.

For example, a subject at risk of developing a bacterial infection can have, for example, risk factors for developing a bacterial infection (e.g., have damaged or moist skin, have a chronic disease, and/or be immunocompromised). For example, a subject at risk for developing a bacterial infection can be exposed to a bacterium or bacteria due to employment (e.g., a health care worker) or due to the prevalence of a bacterium or bacteria at a specific location (e.g., a hospital).

For example, a subject at risk of developing a fungal infection can have, for example, risk factors for developing a fungal infection (e.g., have damaged or moist skin, have a chronic disease, and/or be immunocompromised). For example, a subject at risk for developing a fungal infection can be exposed to a fungus or fungi due to employment (e.g., a health care worker) or due to the prevalence of a fungus or fungi at a specific location (e.g., a hospital).

For example, a subject can have an infection that affects one or more parts of one or both ears of a subject (i.e., the inner ear, the middle ear, the auditory canal, the pinna, etc.). Ear infections can be inflammatory, ulcerative, and/or painful conditions of the ear, which include, but are not limited to, the following: otitis externa, otitis media, otorrhea, acute mastoiditis, otosclerosis, otic pain, otic bleeding, otic inflammation, Lermoyez's syndrome, Meniere's disease, vestibular neuronitis, benign paroxysmal positional vertigo, herpes zoster oticus, Ramsay Hunt's syndrome, viral neuronitis, ganglionitis, geniculate herpes, labyrinthitis, purulent labyrinthitis, perilymph fistulas, presbycusis, drug-induced ototoxicity, acoustic neuromas, aerotitis media, infectious myringitis, bullous myringitis, squamous cell carcinoma, basal cell carcinoma, pre-cancerous otic conditions, nonchromaffin paragangliomas, chemodectomas, glomus jugulare tumors, glomus tympanicum tumors, perichondritis, aural eczematoid dermatitis, malignant external otitis, subperichondrial hematoma, ceruminomas, impacted cerumen, sebaceous cysts, osteomas, keloids, otalgia, tinnitus, vertigo, tympanic membrane infection, tympanitis, otic furuncles, petrositis, conductive and sensorineural hearing loss, epidural abscess, lateral sinus thrombosis, subdural empyema, otitic hydrocephalus, Dandy's syndrome, bullous myringitis, diffuse external otitis, foreign bodies, keratosis obturans, otic neoplasm, otomycosis, trauma, acute barotitis media, acute eustachian tube obstruction, postsurgical otalgia, cholesteatoma, and infections related to an otic surgical procedure.

A "patient" refers to a subject afflicted with one or more infections. In an aspect, a patient can refer to a subject that has been diagnosed with or is suspected of having a bacterial infection. In an aspect, a bacterial infection or suspected bacterial infection can affect at least a portion of one or both feet of the subject, the subject's skin, one or both of the subject's ears, or another appendage, such as at least a portion of one or both of the subject's hands. In an aspect, a patient can refer to a subject that has been diagnosed with or is suspected of having a fungal infection. In an aspect, a fungal infection or suspected fungal infection can affect at least a portion of one or both feet of the subject, the subject's skin, one or both of the subject's ears, or another appendage, such as at least a portion of one or both of the subject's hands.

As used herein, the term "treatment" refers to the medical management of a patient with the intent to cure, ameliorate, stabilize, or prevent a disease, pathological condition, or disorder (such as, for example, a bacterial infection, a suspected bacterial infection, a fungal infection, or a suspected fungal infection, or both). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease, pathological condition, or disorder from occurring in a subject that can be predisposed to the disease but has not yet been diagnosed as having it; (ii) inhibiting the disease, pathological condition, or disorder, i.e., arresting its development; or (iii) relieving the disease, pathological condition, or disorder, i.e., causing regression of the disease.

In an aspect, "treating" means eradicating a bacterial infection, a fungal infection, a suspected bacterial infection, a suspected fungal infection, or a combination thereof. In an aspect, treating means reducing the effects of a bacterial infection or a fungal infection or symptoms of a bacterial infection or a fungal infection. For example, treating an infection can reduce the severity of an established infection in a subject by 1%-100% as compared to a control. In an aspect, treating can refer to a 1%, 2%, 3%, 4%, 5%, 6%, 7%, 8%, 9%, 10%, 20%, 30%, 40%, 50%, 60%, 70%, 80%, 90%, or 100% reduction in the severity of an established bacterial infection or an established fungal infection. For example, treating an infection can reduce one or more symptoms of an infection in a subject by 1%-100% as compared to a control. In an aspect, treating can refer to 1%, 2%, 3%, 4%, 5%, 6%, 7%, 8%, 9%, 10%, 20%, 30%, 40%, 50%, 60%, 70%, 80%, 90%, 100% reduction of one or more symptoms of an established bacterial infection or an established fungal infection. It is understood that treatment does not necessarily refer to a cure or complete ablation or eradication of the bacterial infection, the fungal infection, or both. However, in an aspect, treatment can refer to a cure or complete ablation or eradication of the bacterial infection, the fungal infection, or both.

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed. In an aspect, preventing a bacterial infection, a fungal infection, or both is intended.

As used herein, the term "diagnosed" means having been subjected to a physical examination by a person of skill, for example, a physician, and found to have a condition that can be diagnosed or treated by the disclosed dry formulations, compounded compositions, and/or methods. For example, "diagnosed with a bacterial infection" means having been subjected to a physical examination by a person of skill, for example, a physician, and found to have a condition that can be treated by the disclosed dry formulations, compounded compositions, and/or methods. For example, "suspected of having a bacterial infection" can mean having been subjected to a physical examination by a person of skill, for example, a physician, and found to have a condition that can likely be treated by the disclosed dry formulations, compounded compositions, and/or methods. For example, "diagnosed with a fungal infection" means having been subjected to a physical examination by a person of skill, for example, a physician, and found to have a condition that can likely be treated by the disclosed dry formulations, compounded compositions, and/or methods. For example, "suspected of having a fungal infection" can mean having been subjected to a physical examination by a person of skill, for example, a physician, and found to have a condition that can be likely be treated by the disclosed dry formulations, compounded compositions, and/or methods.

As used herein, the terms "administering" and "administration" refer to any method of providing the disclosed dry formulations and compounded compositions or a pharmaceutical preparation comprising the disclosed dry formulations and compounded compositions to a subject. Such methods are well known to those skilled in the art and include, but are not limited to, the following: oral administration, transdermal administration, administration by inhalation, nasal administration, topical administration, intravaginal administration, ophthalmic administration, intraaural administration, otic administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent.

In various aspects, a disclosed dry formulation, a disclosed compounded composition, or a disclosed pharmaceutical preparation comprising a disclosed dry formulation or a disclosed compounded composition can be administered therapeutically; that is, administered to treat an existing disease or condition. In further various aspects, a disclosed dry formulation, a disclosed compounded composition, or a pharmaceutical preparation comprising a disclosed dry formulation or a disclosed compounded composition can be administered prophylactically; that is, administered for prevention of a disease or condition. In an aspect, the skilled person can determine an efficacious dose, an efficacious schedule, and an efficacious route of administration for a disclosed dry formulation, a disclosed compounded composition, or a disclosed pharmaceutical preparation comprising a disclosed dry formulation or a disclosed compounded composition so as to treat or prevent an infection. In an aspect, the skilled person can also alter, change, or modify an aspect of an administering step so as to improve efficacy of a disclosed dry formulation or disclosed compounded composition or a disclosed pharmaceutical preparation comprising a disclosed dry formulation or a disclosed compounded composition.

In an aspect, administering means contacting at least a portion of one foot or both feet of a subject with agitated water comprising a disclosed dry formulation or a disclosed compounded composition. In an aspect, administering means contacting at least a portion of the subject's skin with a disclosed dry formulation or a disclosed compounded composition. In an aspect, administering means contacting at least a portion of one or both of the subject's ears with a disclosed dry formulation or a disclosed compounded composition. In an aspect, administering means contacting at least a portion of one foot or both feet of a subject with agitated water comprising a compounded composition comprising a disclosed dry formulation or a disclosed compounded composition. In an aspect, administering means contacting at least a portion of the subject's skin with a compounded composition comprising a disclosed compounded composition. In an aspect, administering means contacting one or both of the subject's ears with a compounded composition comprising a disclosed compounded composition.

As used herein, a "foot bath" refers to a container that can hold some volume (e.g., about 1.0 liters to about 10 liters) of an aqueous solution or suspension (e.g., water) and is designed to physically accommodate at least a portion of one or both feet of a subject. Foot baths are known to the skilled person. A foot bath can comprise several features or agents that effect various functions. For example, a foot bath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or feet of the subject, a massage agent (e.g., a roller) that provides massaging contact to at least a portion of one or both feet, a pedicure agent that can clean or contact a foot or feet with a pumice, or a combination thereof. In an aspect, a foot bath can have a water fall element. In an aspect, an agitation agent or an agitator can be coupled to both a motor and the foot bath. Motors and agitators are known to the art. In an aspect, a foot bath can comprise one or more splash guards and other spill-resistant features to ensure that the water remains enclosed within a container. A foot bath may also accommodate a subject's calves, meaning that the container is "deep" so as to allow the enclosed water to contact both the feet and at least a portion of the calves of the subject. Several manufacturers market foot baths including PIBB, Dr. Scholl's, Kendal, Conair (e.g., Model FB5X, FB3, FB27R, FB30, FB52, etc.), and Brookstone.

As used herein, a "mixing container" can be a container that can accommodate one more liquids (such as a diluent, for example) and one or more disclosed dry formulations. A mixing container can have a lid or a cover, which facilitates the mixing of any liquid with any solid that has been added to the container. A mixing container can be used to generate a solution or suspension. In an aspect, a mixing container can contain about 2 ounces to about 30 ounces. In an aspect, a mixing container can contain about 6 ounces. In an aspect, a mixing container can contain about 16 ounces. The art is familiar with mixing containers and mixing containers are commercially available.

As used herein, "modifying the method" can comprise modifying or changing one or more features or aspects of one or more steps of a disclosed method. For example, in an aspect, a method can be altered by changing the amount of a disclosed dry formulation or a disclosed compounded composition applied to a subject's skin, or by changing the frequency of the subject's use of a disclosed dry formulation or a disclosed compounded composition, or by changing the duration of time that the subject uses a disclosed dry formulation or a disclosed compounded composition, or a combination thereof.

In an aspect, a method can be altered by changing the amount of a disclosed dry formulation or a disclosed compounded composition added to a foot bath, by changing the frequency of the subject's use of the foot bath, or by changing the duration of time that the subject's foot or feet contact the water contained within the foot bath, or a combination thereof.

In an aspect, a method can be altered by changing the amount of a disclosed dry formulation or a disclosed compounded composition applied to one or both of the subject's ears. A method can be altered by changing the amount of a disclosed formulation or a disclosed compounded composition applied to the subject's skin.

The term "contacting" as used herein refers to bringing a disclosed dry formulation or a disclosed compounded composition together with a target area or intended target area in such a manner that the disclosed dry formulation or the disclosed compounded composition can exert an effect on the intended target or targeted area either directly or indirectly. A target or intended target area can be at least a portion of one or both feet of a subject, at least a portion of one or both of the subject's ears, or at least portion of the subject's skin or an area diagnosed with, suspected of having a bacterial infection or a fungal infection, or susceptible to developing a bacterial infection or a fungal infection.

In an aspect, "contacting" means to insert or immerse at least a portion of one or both feet of a subject into the water contained within a foot bath, wherein the water comprises a disclosed dry formulation or a disclosed compounded composition. In an aspect, "contacting" means topically applying a disclosed dry formulation or a disclosed compounded composition to the skin of a subject. In an aspect, a disclosed compounded composition can be contacted with one or both of the subject's ears.

The term "mixing" as used in a disclosed method means to physically combine the recited components so as to achieve a homogenous dry formulation. In an aspect, the recited components can be shaken, or stirred, or agitated so as to achieve a homogenous dry formulation. In an aspect, "mixing" can also include sifting the homogenous dry formulation though a fine mesh strainer. A suitable mixer is a TURBULA® mixer, which is able to mix powdery substances with differing specific weights and particle sizes. The mixing can be generally performed for a pre-determined amount of time, i.e., for 10 seconds, 20 seconds, 30 seconds, 45 seconds, 1 minute, 5 minute, 10 minutes, 20 minutes, 30 minutes, 40 minutes, 50 minutes, 1 hour, 2 hours, 3 hours, or more. A person skilled in the art could ascertain without undue experimentation, the amount of time required to mix the recited components so as to achieve a homogenous dry formulation.

In an aspect, "mixing" can be used to describe the process of making a compounded composition (i.e., a solution or suspension) by adding one or more disclosed dry formulations to a diluent (such as, for example, a hydrocortisone/acetic acid otic solution, a sodium chloride solution, etc.). For example, mixing means to physically combine a disclosed dry formulation with a diluent to make a compounded composition (i.e., a solution or a suspension). Such mixing can occur in a disclosed mixing container.

As used herein, "ointment" refers to a homogeneous, viscous preparation that can be applied to a subject. In aspect, the term "ointment" can be considered synonymous to a lotion, a cream, an emulsion, a gel, an emollient, etc. In an aspect, an ointment comprises a disclosed compounded composition. An ointment can be applied in a variety of ways, included, for example, but not limited to, direct topical application to the subject's skin or contact with skin in an enclosed environment, such as a foot bath.

As used herein, LoxaSperse™ refers to an excipient base powder comprising a blend of micronized xylitol and poloxamers. Such base compositions are known to those skilled in the art. LoxaSperse™ is manufactured by PCCA (Houston, Tex.) and is used as a chemical dispersing or solubilizing agent, thereby improving the solubility and dispersibility of poorly water soluble active pharmaceutical ingredients (APIs) or agents. LoxaSperse™ can be obtained from a bulk source.

As used herein, XyliFos™ refers to an excipient base powder comprising xylitol, poloxamer 407, hydroxylpropyl betadex, and epigallocatechin gallate. XyliFos™ is manufactured by PCCA (Houston, Tex.) and is used as a chemical dispersing or solubilizing agent, thereby improving the solubility and dispersibility of poorly water soluble active pharmaceutical ingredients (APIs) or agents. XyliFos™ can be obtained from a bulk source.

In an aspect, xylitol can comprise an ointment or can comprise a dry powder. In an aspect, xylitol can be xylitol NF (20-80 MESH).

As used herein, diluents are known to the art. In an aspect, a diluent can be a hydrocortisone/acetic acid otic solution. A hydrocortisone/acetic acid otic solution can be a commercially available hydrocortisone/acetic acid otic solution, for example, a hydrocortisone 1%/acetic acid 2% otic solution. In an aspect, a commercially available hydrocortisone 1%/acetic acid 2% otic solution can comprise a propylene glycol vehicle, which comprises one or more inactive ingredients including, but not limited to, propylene glycol diacetate (3%), benzethonium chloride (0.02%), sodium acetate (0.015%), and citric acid (0.05%), buffered to pH 3. Commercially available hydrocortisone/acetic acid otic solutions are known to the art (i.e., Hi-Tech Pharmacal, Amityville, N.Y.). The empirical formula for acetic acid is $CH_3COOH$ and the empirical formula for hydrocortisone is $C_{21}H_{30}O_5$. Acetic acid has anti-bacterial and anti-fungal properties. Hydrocortisone is a corticosteroid that is an anti-inflammatory, anti-allergic, and anti-pruritic. Propylene glycol is hydrophilic and provides a low surface tension. Benzethonium chloride is a surface active agent that promotes contact of the solution with tissues.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, or suspensions, which may include dispersions, colloids, or emulsions, as well as sterile powders for reconstitution into sterile injectable solutions, suspensions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. These compositions can also contain adjuvants such as preservatives, wetting agents, emulsifying agents and dispersing agents. Prevention of the action of microorganisms can be ensured by the inclusion of various anti-bacterial and anti-fungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, "determining" can refer to measuring or ascertaining the presence and severity of an infection, such as, for example, a bacterial infection or a fungal infection that affects at least a portion of a subject's skin, one or both of the subject's ears, or one or more of a subject's appendages (e.g., at least a portion of one or both feet). Methods and techniques used to determining the presence and/or severity of an infection are typically known to the medical arts. For example, the art is familiar with the ways to identify and/or diagnose the presence, severity, or both of a bacterial infection, a fungal infection, or both.

As used herein, "effective amount" and "amount effective" can refer to an amount that is sufficient to achieve the desired result such as, for example, the treatment and/or prevention of a bacterial infection or a suspected bacterial infection or a fungal infection or a suspected fungal infection. As used herein, the terms "effective amount" and "amount effective" can refer to an amount that is sufficient to achieve the desired an effect on an undesired condition (e.g., a bacterial or a fungal infection). For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific disclosed dry formulation or specific compounded composition, or methods employed; the age, body weight, general health, sex and diet of the patient; the time of administration; the route of administration; the rate of excretion of the disclosed dry formulation or the disclosed compounded composition employed; the duration of the treatment; drugs used in combination or coincidental with a disclosed dry formulation or a disclosed compounded composition employed and like factors well known in the medical arts. For example, it is well within the skill of the art to start doses of a disclosed dry formulation or a disclosed compounded composition at levels lower than those required to achieve the desired therapeutic effect and to gradually increase the dosage until the desired effect is achieved. If desired, then the effective daily dose can be divided into multiple doses for purposes of administration. Consequently, a single dose of a disclosed dry formulation or a single dose a disclosed compounded composition, or methods can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition, such as, for example, a bacterial infection or a fungal infection.

Disclosed are the components to be used to prepare a disclosed dry formulation or a disclosed compounded composition as well as the disclosed dry formulations and disclosed compounded compositions used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

B. Active Agents

1. Anti-Infective Agents

As used herein, an anti-infective agent can be an anti-bacterial agent, an anti-fungal agent, a combination of anti-bacterial agents, a combination of anti-fungal agents, or a combination of anti-bacterial agents and anti-fungal agents.

Anti-bacterial agents are known to the art. For example, the art generally recognizes several categories of anti-bacterial agents including (1) enicillins, (2) cephalosporins, (3) quinolones, (4) aminoglycosides, (5) monobactams, (6) carbapenems, (7) macrolides, and (8) other agents.

For example, as used herein, an anti-bacterial agent can comprise Afenide, Amikacin, Amoxicillin, Ampicillin, Arsphenamine, Augmentin, Azithromycin, Azlocillin, Aztreonam, Bacampicillin, Bacitracin, Balofloxacin, Besifloxacin, Capreomycin, Carbacephem (loracarbef), Carbenicillin, Cefacetrile (cephacetrile), Cefaclomezine, Cefaclor, Cefadroxil (cefadroxyl), Cefalexin (cephalexin), Cefaloglycin (cephaloglycin), Cefalonium (cephalonium), Cefaloram, Cefaloridine (cephaloradine), Cefalotin (cephalothin), Cefamandole, Cefaparole, Cefapirin (cephapirin), Cefatrizine, Cefazaflur, Cefazedone, Cefazolin (cephazolin), Cefcanel, Cefcapene, Cefclidine, Cefdaloxime, Cefdinir, Cefditoren, Cefedrolor, Cefempidone, Cefepime, Cefetamet, Cefetrizole, Cefivitril, Cefixime, Cefluprenam, Cefmatilen, Cefmenoxime, Cefmepidium, Cefmetazole, Cefodizime, Cefonicid, Cefoperazone, Cefoselis, Cefotaxime, Cefotetan, Cefovecin, Cefoxazole, Cefoxitin, Cefozopran, Cefpimizole, Cefpirome, Cefpodoxime, Cefprozil (cefproxil), Cefquinome, Cefradine (cephradine), Cefrotil, Cefroxadine, Cefsumide, Ceftaroline, Ceftazidime, Ceftazidime/Avibactam, Cefteram, Ceftezole, Ceftibuten, Ceftiofur, Ceftiolene, Ceftioxide, Ceftizoxime, Ceftobiprole, Ceftriaxone, Cefuracetime, Cefuroxime, Cefuzonam, Cephalexin, Chloramphenicol, Chlorhexidine, Ciprofloxacin, Clarithromycin, Clavulanic Acid, Clinafloxacin, Clindamycin, Cloxacillin, Colimycin, Colistimethate, Colistin, Crysticillin, Cycloserine 2, Demeclocycline, Dicloxacillin, Dirithromycin, Doripenem, Doxycycline, Efprozil, Enoxacin, Ertapenem, Erythromycin, Ethambutol, Flucloxacillin, Flumequine, Fosfomycin, Furazolidone, Gatifloxacin, Geldanamycin, Gemifloxacin, Gentamicin, Glycopeptides, Grepafloxacin, Herbimycin, Imipenem, Isoniazid, Kanamycin, Levofloxacin, Lincomycin, Linezolid, Lipoglycopeptides, Lomefloxacin, Meropenem, Meticillin, Metronidazole, Mezlocillin, Minocycline, Mitomycin, Moxifloxacin, Mupirocin, Nadifloxacin, Nafcillin, Nalidixic Acid, Neomycin, Netilmicin, Nitrofurantoin, Norfloxacin, Ofloxacin, Oxacillin, Oxazolidinones, Oxolinic Acid, Oxytetracycline, Oxytetracycline, Paromomycin, Pazufloxacin, Pefloxacin, Penicillin G, Penicillin V, Pipemidic Acid, Piperacillin, Piromidic Acid, Pivampicillin, Pivmecillinam, Platensimycin, Polymyxin B, Pristinamycin, Prontosil, Prulifloxacin, Pvampicillin, Pyrazinamide, Quinupristin/dalfopristin, Rifabutin, Rifalazil, Rifampin, Rifamycin, Rifapentine, Rosoxacin, Roxithromycin, Rufloxacin, Sitafloxacin, Sparfloxacin, Spectinomycin, Spiramycin, Streptomycin, Sulbactam, Sulfacetamide, Sulfamethizole, Sulfamethoxazole, Sulfanilimide, Sulfisoxazole, Sulphonamides, Sultamicillin, Teicoplanin, Telavancin, Telithromycin, Temafloxacin, Tetracycline, Thiamphenicol, Ticarcillin, Tigecycline, Tinidazole, Tobramycin, Tosufloxacin, Trimethoprim, Trimethoprim-Sulfamethoxazole, Troleandomycin, Trovafloxacin, Tuberactinomycin, Vancomycin, Viomycin, or pharmaceutically acceptable salts thereof, or a combination thereof.

In an aspect, an anti-bacterial agent can be a quinolone. Quinolones include, but are not limited to, the following: moxifloxacin, levofloxacin, and ciprofloxacin. In an aspect, an anti-bacterial agent can be an aminoglycoside. Aminoglycosides include, but are not limited to, the following: tobramycin and gentamicin. In an aspect, an anti-bacterial agent can be a cephalosporin. Cephalosporins include, but are not limited to, the following: ceftriaxone, ceftazidime, and cefepime. In an aspect, an anti-bacterial agent can be mupirocin, vancomycin, azithromycin, colistemethate, sulfamethoxazole, trimethoprim, meropenem, clindamycin, doxycycline, and linezolid.

In an aspect, an anti-bacterial agent can comprise an ointment or can comprise a dry powder. In an aspect, the dry powder can be obtained from crushed tablets comprising an anti-bacterial agent or from a container comprising the anti-bacterial agent as a dry powder. In an aspect, an anti-bacterial agent can be pure or substantially pure and can be obtained from a bulk source. In an aspect, an anti-bacterial agent can be commercially available as, for example, a tablet, a troche, a cream, an ointment, or a powder.

Anti-fungal agents are known to the art. The art generally recognizes several categories of anti-fungal agents including (1) azoles (imidazoles), (2) antimetabolites, (3) allylamines, (4) morpholine, (5) glucan synthesis inhibitors (echinocandins), (6) polyenes, (7) benoxaaborale; (8) other antifungal/onychomycosis agents, and (9) new classes of antifungal/onychomycosis agents.

For example, as used herein, an anti-fungal agent can comprise Abafungin, Albaconazole, Amorolfin, Amphotericin B, Anidulafungin, Bifonazole, Butenafine, Butoconazole, Candicidin, Caspofungin, Ciclopirox, Clotrimazole, Econazole, Fenticonazole, Filipin, Fluconazole, Flucytosine, Griseofulvin, Haloprogin, Hamycin, Isavuconazole, Isoconazole, Itraconazole, Ketoconazole, Micafungin, Miconazole, Naftifine, Natamycin, Nystatin, Omoconazole, Oxiconazole, Polygodial, Posaconazole, Ravuconazole, Rimocidin, Sertaconazole, Sulconazole, Terbinafine, Terconazole, Tioconazole, Tolnaftate, Undecylenic Acid, Voriconazole, or pharmaceutically acceptable salts thereof, or a combination thereof.

In an aspect, an anti-fungal agent can be an azole. Azoles include, but are not limited to, the following: clotrimazole, econazole, fluconazole, itraconazole, ketoconazole, miconazole, oxiconazole, sulconazole, and voriconazole. In an aspect, an anti-fungal agent can be amphotericin.

In an aspect, an anti-fungal agent can comprise an ointment or can comprise a dry powder. In an aspect, the dry powder can be obtained from crushed tablets comprising an anti-fungal agent or from a container comprising the anti-fungal agent as a dry powder. In an aspect, an anti-fungal agent can be pure or substantially pure and can be obtained from a bulk source. In an aspect, an anti-fungal agent can be commercially available as, for example, a tablet, a troche, a cream, an ointment, or a powder.

Clindamycin is a semisynthetic broad spectrum antibiotic produced by chemical modification of the parent compound lincomycin. The molecular formula for clindamycin is $C_{22}H_{24}N_2O_8$.

In an aspect, clindamycin can comprise an ointment or can comprise a dry powder. In an aspect, the dry powder can be obtained from crushed tablets comprising clindamycin or from a container comprising clindamycin as a dry powder. In an aspect, clindamycin can be pure or substantially pure and can be obtained from a bulk source. In an aspect, clindamycin can be commercially available.

Clindamycin hydrochloride is the hydrochloride salt form of clindamycin. The molecular formula for clindamycin hydrochloride is $C_{18}H_{34}Cl_2N_2O_5S$.

In an aspect, clindamycin hydrochloride can comprise an ointment or can comprise a dry powder. In an aspect, the dry powder can be obtained from crushed tablets comprising clindamycin hydrochloride or from a container comprising clindamycin hydrochloride as a dry powder. In an aspect, clindamycin hydrochloride can be pure or substantially pure and can be obtained from a bulk source. In an aspect, clindamycin hydrochloride can be commercially available. In an aspect, clindamycin hydrochloride can be clindamycin hydrochloride USP 83.22. In an aspect, about 1.13 g of clindamycin HCl is approximately equivalent to 1.0 g of pure or substantially pure clindamycin.

Doxycycline is a synthetic tetracycline derivative. The molecular formula for doxycycline is $C_{22}H_{24}N_2O_8$.

In an aspect, doxycycline can comprise an ointment or can comprise a dry powder. In an aspect, the dry powder can be obtained from crushed tablets comprising doxycycline or from a container comprising doxycycline as a dry powder. In an aspect, doxycycline can be pure or substantially pure and can be obtained from a bulk source. In an aspect, doxycycline can be commercially available.

Doxycycline hyclate is a salt form of doxycycline. The molecular formula for doxycycline hyclate is $C_{46}H_{58}Cl_2N_4O_{18}$.

In an aspect, doxycycline hyclate can comprise an ointment or can comprise a dry powder. In an aspect, the dry powder can be obtained from crushed tablets comprising doxycycline hyclate or from a container comprising doxycycline hyclate as a dry powder. In an aspect, doxycycline hyclate can be pure or substantially pure and can be obtained from a bulk source. In an aspect, doxycycline hyclate can be doxycycline hyclate USP powder 83.97 In an aspect, doxycycline hyclate can be commercially available, for example, as doxycycline hyclate 100 mg tablets.

Mupirocin is an anti-bacterial agent that has excellent activity against gram-positive staphylococci and streptococci. The molecular formula for mupirocin is $C_{26}H_{44}O_9$.

In an aspect, mupirocin can comprise an ointment or can comprise a dry powder. In an aspect, the dry powder can be obtained from crushed tablets comprising mupirocin or from a container comprising mupirocin as a dry powder. In an aspect, mupirocin can be pure or substantially pure and can be obtained from a bulk source. In an aspect, mupirocin can be commercially available, for example, as a mupirocin 2.0% ointment or a mupirocin powder USP 95.41.

Clotrimazole is an azole antifungal with a broad spectrum of antimycotic activity. The molecular formula for clotrimazole is $C_{22}H_{17}ClN_2$.

In an aspect, clotrimazole can comprise an ointment or can comprise a dry powder. In an aspect, the dry powder can be obtained from crushed tablets comprising clotrimazole or from a container comprising clotrimazole as a dry powder. In an aspect, clotrimazole can be pure or substantially pure and can be obtained from a bulk source. In an aspect, clotrimazole can be commercially available, for example, as clotrimazole powder USP 100.2 or as a 10 mg troche.

As used herein, the recitation of any anti-infective agent inherently encompasses the pharmaceutically acceptable salts thereof.

2. Corticosteroids

Corticosteroids are well-known in the art. Corticosteroids mimic the effects of hormones that the body produces naturally in your adrenal glands. Corticosteroids can suppress inflammation and can reduce the signs and symptoms of inflammatory conditions (e.g., arthritis and asthma). Corticosteroids can also suppress the immune system. Corticosteroids can act on a number of different cells (e.g., mast cells, neutrophils, macrophages and lymphocytes) and a number of different mediators (e.g., histamine, leukotriene, and cytokine subtypes).

Steroids include, but are not limited to, the following: triamcinolone and its derivatives (e.g., diacetate, hexacetonide, and acetonide), betamethasone and its derivatives (e.g., dipropionate, benzoate, sodium phosphate, acetate, and valerate), dexamethasone and its derivatives (e.g., dipropionate and valerate), flunisolide, prednisone and its derivatives (e.g., acetate), prednisolone and its derivatives (e.g., acetate, sodium phosphate, and tebutate), methylprednisolone and its derivatives (e.g., acetate and sodium succinate), fluocinolone and its derivatives (e.g., acetonide), diflorasone and its derivatives (e.g., diacetate), halcinonide, desoximetasone (desoxymethasone), diflucortolone and its derivatives (e.g., valerate), flucloronide (fluclorolone acetonide), fluocinonide, fluocortolone, fluprednidene and its derivatives (e.g., acetate), flurandrenolide (flurandrenolone), clobetasol and its derivatives (e.g., propionate), clobetasone and its derivatives (e.g., butyrate), alclometasone, flumethasone and its derivatives (e.g., pivalate), fluocortolone and its derivatives (e.g., hexanoate), amcinonide, beclometasone and its derivatives (e.g., dipropionate), fluticasone and its derivatives (e.g., propionate), difluprednate, prednicarbate, flurandrenolide, mometasone, and desonide.

Betamethasone is a glucocorticoid with metabolic, immunosuppressive and anti-inflammatory activities. The molecular formula for betamethasone is $C_{22}H_{29}FO_5$.

In an aspect, the betamethasone can comprise an ointment or can comprise a dry powder. In an aspect, the dry powder can be obtained from crushed tablets comprising betamethasone or from a container comprising betamethasone as a dry powder. The betamethasone can be pure or substantially pure and can be obtained from a bulk source. In an aspect, betamethasone can be powder for injection USP. In an aspect, betamethasone can be commercially available.

Betamethasone sodium phosphate is the disodium salt of the 21-phosphate ester of betamethasone. The molecular formula for betamethasone sodium phosphate is $C_{22}H_{28}FNa_2O_8P$.

In an aspect, the betamethasone sodium phosphate can comprise an ointment or can comprise a dry powder. In an aspect, the dry powder can be obtained from crushed tablets comprising betamethasone sodium phosphate or from a container comprising betamethasone sodium phosphate as a dry powder. The betamethasone sodium phosphate can be pure or substantially pure and can be obtained from a bulk source. In an aspect, betamethasone sodium phosphate can be commercially available. In an aspect, betamethasone sodium phosphate can be powder for injection USP 90.94. In an aspect, about 4 mg of betamethasone sodium phosphate is equivalent to about 3 mg of bethamethasone.

Dexamethasone is a corticosteroid with potent anti-inflammatory properties. The molecular formula for dexamethasone is $C_{22}H_{29}FO_5$.

In an aspect, the dexamethasone can comprise an ointment or can comprise a dry powder. In an aspect, the dry powder can be obtained from crushed tablets comprising dexamethasone or from a container comprising dexamethasone as a dry powder. The dexamethasone can be pure or substantially pure and can be obtained from a bulk source. In an aspect, dexamethasone can be powder for injection. In an aspect, dexamethasone can be commercially available, for example, such as a 6 mg dexamethasone tablet.

3. Antihistamines

Antihistamines are well-known to the art. Antihistamines act to reduce or block histamine receptors (e.g., $H_1$ receptors and $H_2$ receptors). Antihistamines include, but are not limited to, the following: Acrivastine, Azelastine, Bilastine, Bromodiphenhydramine, Brompheniramine, Buclizine, Carbinoxamine, Cetirizine, Chlorodiphenhydramine, Chlorphenamine, Chlorpheniramine, Chlorpromazine, Cimetidine, Clemastine, Cyclizine, Cyproheptadine, Desloratadine, Dexbrompheniramine, Dexchlorpheniramine, Dimenhydrinate, Dimetindene, Diphenhydramine, Doxylamine, Ebastine, Embramine, Emedastine, Famotidine, Fexofenadine, Hydroxyzine, Lafutidine, Levocabastine, Loratadine, Meclozine, Mirtazapine, Nizatidine, Olopatadine, Orphenadrine, Phenindamine, Pheniramine, Phenyltoloxamine, Promethazine, Pyrilamine, Quetiapine, Ranitidine, Roxatidine, Rupatadine, Tiotidine, Tripelennamine, and Triprolidine, or pharmaceutically acceptable salts thereof, or a combination thereof.

4. Anticholinergics

Anticholinergics are well-known to the art. Anticholinergics act to block the action of the neurotransmitter acetylcholine in both the central and peripheral nervous systems. Anticholinergics include, but are not limited to, the following: Atropine, Belladonna alkaloids, Benzatropine, Benztropine Mesylate, Biperiden, Bupropion, Chlorpheniramine, Clemastine, Darifenacin, Dextromethorphan, Dicyclomine, Dimenhydrinate, Diphenhydramine, Doxacurium, Doxepin, Doxylamine, Fesoterodine, Flavoxate, Glycopyrrolate, Hexamethonium, Hydroxyzine, Hyoscyamine, Ipratropium, Mecamylamine, Orphenadrine, Oxitropium, Oxybutynin, Procyclidine, Propantheline, Scopolamine, Solifenacin, Tiotropium, Tolterodine, Trihexyphenidyl, Tropicamide, and Tubocurarine, or pharmaceutically acceptable salts thereof, or a combination thereof.

5. Mucolytics

Mucolytics are well-known to the art. Mucolytics act to loosen and clear mucus from the airways. Mucolytics include, but are not limited to, the following: Acetylcysteine, Bromheksin, Carbocysteine, Erdosteine, Guiafenesin, and Iodinated Glycerol, or pharmaceutically acceptable salts thereof, or a combination thereof.

6. Leukotriene Receptor Antagonists

Leukotriene receptor antagonists are well-known to the art. Leukotriene receptor antagonists function as a leukotriene-related enzyme inhibitor or a leukotriene receptor antagonist to oppose the function of these inflammatory mediators. Leukotriene receptor antagonists include, but are not limited to, the following: montelukast, zafirlukast, and zilueton, or pharmaceutically acceptable salts thereof, or a combination thereof.

C. Dry Formulations

Disclosed herein are dry formulations for treating an infection.

1. Mupirocin, an Anti-Bacterial Agent, and an Anti-Fungal Agent

Disclosed herein is a dry formulation comprising a therapeutically effective amount of mupirocin, a therapeutically effective amount of an anti-bacterial agent, and a therapeutically effective amount of an anti-fungal agent. Disclosed herein is a dry formulation comprising a therapeutically effective amount of mupirocin, a therapeutically effective amount of an anti-bacterial agent, a therapeutically effective amount of an anti-fungal agent, a sufficient amount of an excipient base powder, and a sufficient amount of xylitol.

In an aspect, a disclosed dry formulation comprising mupirocin, an anti-bacterial agent, and an anti-fungal agent can comprise mupirocin and the anti-bacterial agent in a ratio from about a 1:1 to about 1:2. In an aspect, a disclosed dry formulation comprising mupirocin, an anti-bacterial agent, and an anti-fungal agent can comprise mupirocin and the anti-bacterial agent in a ratio of about 1:1.25.

In an aspect, a disclosed dry formulation comprising mupirocin, an anti-bacterial agent, and an anti-fungal agent can comprise mupirocin and the anti-fungal agent in a ratio from about 1:0.05 to about 1:0.3. In an aspect, a disclosed dry formulation comprising mupirocin, an anti-bacterial agent, and an anti-fungal agent can comprise mupirocin and the anti-fungal agent in a ratio of about 1:0.15.

In an aspect, a disclosed dry formulation comprising mupirocin, an anti-bacterial agent, and an anti-fungal agent can comprise the anti-bacterial agent and the anti-fungal agent in a ratio from about 1:0.01 to about 1:0.3. In an aspect, a disclosed dry formulation comprising mupirocin, an anti-bacterial agent, and an anti-fungal agent can comprise the anti-bacterial agent and the anti-fungal agent in a ratio of about 1:0.12.

In an aspect, a disclosed dry formulation comprising mupirocin, an anti-bacterial agent, and an anti-fungal agent can comprise the excipient base powder and xylitol in a ratio from about 1:9.0 to about 1:10. In an aspect, a disclosed dry formulation comprising mupirocin, an anti-bacterial agent, and an anti-fungal agent can comprise the excipient base powder and xylitol in about a ratio of about 1:9.2.

In an aspect, 1 g of the dry formulation comprising mupirocin, an anti-bacterial agent, an anti-fungal agent, an excipient base powder, and xylitol can comprise about 0.0256 g mupirocin, about 0.0320 g anti-bacterial agent, about 0.0038 g anti-fungal agent, about 0.0918 g excipient base powder, and about 0.8448 g xylitol.

Mupirocin is known to the art and is discussed supra. In an aspect, mupirocin can be mupirocin powder USP 95.41. Anti-bacterial agents are known to the art and discussed supra. For example, in an aspect, the anti-bacterial agent can comprise a dry powder. In an aspect, the dry powder can be obtained from crushed tablets comprising the anti-bacterial agent or from a container comprising the anti-bacterial agent as a dry powder. In an aspect, the anti-bacterial agent clotrimazole can be pure or substantially pure and can be obtained from a bulk source. In an aspect, the anti-bacterial agent can be commercially available. In an aspect, the anti-bacterial agent can be clindamycin or a pharmaceutically acceptable salt thereof (e.g., hydrochloride). In an aspect, clindamycin hydrochloride can be clindamycin hydrochloride USP 83.22. Anti-fungal agents are known to the art and discussed supra. For example, in an aspect, the anti-fungal agent can comprise a dry powder. In an aspect, the dry powder can be obtained from crushed tablets comprising the anti-fungal agent or from a container comprising the anti-fungal as a dry powder. In an aspect, the anti-fungal agent can be pure or substantially pure and can be obtained from a bulk source. In an aspect, the anti-fungal agent can be commercially available. In an aspect, the anti-fungal agent can be clotrimazole USP 100.2. Excipient base powders are known to the art and are discussed supra. In an aspect, an excipient base powder can be LoxaSperse™ excipient base powder or XyliFos™ excipient base powder. Xylitol is known to the art and is discussed supra.

In an aspect, a disclosed dry formulation comprising mupirocin, an anti-bacterial agent, and an anti-fungal agent can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising mupirocin, an anti-bacterial agent, and an anti-fungal agent can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising mupirocin, an anti-bacterial agent, and an anti-fungal agent can be encapsulated in a capsule or in one or more capsules.

In an aspect, each capsule can comprise about 2.0% mupirocin, about 2.5% anti-bacterial agent, about 0.3% anti-fungal agent, about 7.16% excipient base powder, and about 65.9% xylitol. In an aspect, each capsule can comprise about 0.02 g (20 mg) mupirocin, about 0.025 g (25 mg) anti-bacterial agent, about 0.003 g (3 mg) anti-fungal agent, about 0.0716 g (71.6 mg) excipient base powder, and about 0.659 g (659 mg) xylitol.

In an aspect, the disclosed dry formulation comprising mupirocin, an anti-bacterial agent, and an anti-fungal agent can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

2. Mupirocin, Clindamycin Hydrochloride, and Clotrimazole

Disclosed herein is a dry formulation comprising a therapeutically effective amount of mupirocin, a therapeutically effective amount of clindamycin hydrochloride, and a therapeutically effective amount of clotrimazole. Disclosed herein is a dry formulation comprising a therapeutically effective amount of mupirocin, a therapeutically effective amount of clindamycin hydrochloride, a therapeutically effective amount of clotrimazole, and a sufficient amount of an excipient base powder.

Disclosed herein is a dry formulation comprising a therapeutically effective amount of mupirocin, a therapeutically effective amount of clindamycin hydrochloride, a therapeutically effective amount of clotrimazole, a sufficient amount of an excipient base powder, and a sufficient amount of xylitol.

In an aspect, a disclosed dry formulation comprising mupirocin, clindamycin hydrochloride, and clotrimazole can comprise mupirocin and clindamycin hydrochloride in a ratio from about a 1:1 to about 1:2. In an aspect, a disclosed dry formulation comprising mupirocin, clindamycin hydrochloride, and clotrimazole can comprise mupirocin and clindamycin hydrochloride in a ratio of about 1:1.25. In an aspect, a disclosed dry formulation comprising mupirocin, clindamycin hydrochloride, and clotrimazole can comprise mupirocin and clotrimazole in a ratio from about 1:0.0.5 to about 1:0.3. In an aspect, a disclosed dry formulation comprising mupirocin, clindamycin hydrochloride, and clotrimazole can comprise mupirocin and clotrimazole in a ratio of about 1:0.15. In an aspect, a disclosed dry formulation comprising mupirocin, clindamycin hydrochloride, and clotrimazole can comprise clindamycin hydrochloride and clotrimazole in a ratio from about 1:0.1 to about 1:0.3. In an aspect, a disclosed dry formulation comprising mupirocin, clindamycin hydrochloride, and clotrimazole can comprise clindamycin hydrochloride and clotrimazole in a ratio of about 1:0.12. In an aspect, a disclosed dry formulation comprising mupirocin, clindamycin hydrochloride, and clotrimazole can comprise the excipient base powder and xylitol in a ratio from about 1:9.0 to about 1:10. In an aspect, a disclosed dry formulation comprising mupirocin, clindamycin hydrochloride, and clotrimazole can comprise the excipient base powder and xylitol in about a ratio of about 1:9.2.

In an aspect, 1 g of the dry formulation comprising mupirocin, clindamycin hydrochloride, clotrimazole, an excipient base powder, and xylitol can comprise about 0.0256 g mupirocin, about 0.0320 g clindamycin hydrochloride, about 0.0038 g clotrimazole, about 0.0918 g excipient base powder, and about 0.8448 g of xylitol. In an aspect, 1 g of the dry formulation comprising mupirocin, clindamycin hydrochloride, clotrimazole, and an excipient base powder can comprise about 0.0285 g mupirocin, about 0.0357 g clindamycin hydrochloride, about 0.004 g clotrimazole, and about 0.924 g excipient base powder.

Mupirocin is known to the art and is discussed supra. In an aspect, mupirocin can be mupirocin USP 95.41. Clindamycin hydrochloride is known to the art and is discussed supra. In an aspect, clindamycin hydrochloride can be clindamycin hydrochloride USP 83.22. Clotrimazole is known to the art and is discussed supra. In an aspect, clotrimazole can be clotrimazole USP 100.2. Excipient base powders are known to the art and are discussed supra. In an aspect, an excipient base powder can be LoxaSperse™ excipient base powder or XyliFos™ excipient base powder. Xylitol is known to the art and is discussed supra.

In an aspect, a disclosed dry formulation comprising mupirocin, clindamycin hydrochloride, and clotrimazole can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising mupirocin, clindamycin hydrochloride, and clotrimazole can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising mupirocin, clindamycin hydrochloride, clotrimazole, an excipient base powder, and xylitol can be encapsulated in a capsule or in one or more capsules. In an aspect, each capsule can comprise about 2.0% mupirocin, about 2.5% clindamycin hydrochloride, about 0.3% clotrimazole, about 7.16% excipient base powder, and about 65.9% xylitol. In an aspect, each capsule can comprise about 0.02 g mupirocin, about 0.025 g clindamycin hydrochloride, about 0.003 g clotrimazole, about 0.0716 g excipient base powder, and about 0.659 g xylitol.

In an aspect, a disclosed dry formulation comprising mupirocin, clindamycin hydrochloride, clotrimazole, and an excipient base powder can be encapsulated in a capsule or in one or more capsules. In an aspect, each capsule can comprise about 2.0% mupirocin, about 2.5% clindamycin hydrochloride, about 0.3% clotrimazole, and about 64.7% excipient base powder. In an aspect, each capsule can comprise about 0.02 g mupirocin, about 0.025 g clindamycin hydrochloride, about 0.003 g clotrimazole, and about 0.647 g excipient base powder.

In an aspect, a disclosed dry formulation comprising mupirocin, clindamycin hydrochloride, clotrimazole, an excipient base powder, and xylitol can be encapsulated in a capsule or in one or more capsules. In an aspect, each capsule can comprise about 20 mg mupirocin, about 25 mg clindamycin hydrochloride, and about 3 mg clotrimazole.

In an aspect, the disclosed dry formulation comprising mupirocin, clindamycin hydrochloride, clotrimazole, an excipient base powder, and xylitol can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

3. Mupirocin, A Corticosteroid or a Salt Thereof, and an Anti-Fungal Agent

Disclosed herein is a dry formulation comprising a therapeutically effective amount of mupirocin, a therapeutically effective amount of a corticosteroid or a pharmaceutically acceptable salt thereof, and a therapeutically effective amount of an anti-fungal agent. Disclosed herein is a dry formulation comprising a therapeutically effective amount of mupirocin, a therapeutically effective amount of a corticosteroid or a pharmaceutically acceptable salt thereof, a therapeutically effective amount of an anti-fungal agent, a sufficient amount of an excipient base powder, and a sufficient amount of xylitol.

In an aspect, a disclosed dry formulation comprising mupirocin, a corticosteroid or a pharmaceutically acceptable salt thereof, and an anti-fungal agent can comprise mupirocin and the corticosteroid or a salt thereof in a ratio from about a 1:0.01 to about 1:0.2. In an aspect, a disclosed dry formulation comprising mupirocin, a corticosteroid or a pharmaceutically acceptable salt thereof, and an anti-fungal agent can comprise mupirocin and the corticosteroid or a salt thereof in a ratio of about 1:0.05. In an aspect, a disclosed dry formulation comprising mupirocin, a corticosteroid or a pharmaceutically acceptable salt thereof, and an anti-fungal agent can comprise mupirocin and the anti-fungal agent in a ratio from about 1:0.1 to about 1:0.3. In an aspect, a disclosed dry formulation comprising mupirocin, a corticosteroid or a pharmaceutically acceptable salt thereof, and an anti-fungal agent can comprise mupirocin and the anti-fungal agent in a ratio of about 1:0.15. In an aspect, a disclosed dry formulation comprising mupirocin, a corticosteroid or a pharmaceutically acceptable salt thereof, and an anti-fungal agent can comprise the corticosteroid or a salt thereof and the anti-fungal agent in a ratio from about 1:1 to about 1:5. In an aspect, a disclosed dry formulation comprising mupirocin, a corticosteroid or a salt thereof, and an anti-fungal agent can comprise the corticosteroid or a salt thereof and the anti-fungal agent in a ratio of about 1:3. In an aspect, a disclosed dry formulation comprising mupirocin, a corticosteroid or a pharmaceutically acceptable salt thereof, and an anti-fungal agent can comprise the excipient base powder and xylitol in a ratio from about 1:9 to about 1:10. In an aspect, a disclosed dry formulation comprising mupirocin, a corticosteroid or a pharmaceutically acceptable salt thereof, and an anti-fungal agent can comprise the excipient base powder and xylitol in about a ratio of about 1:9.6.

In an aspect, 1 g of the dry formulation comprising mupirocin, a corticosteroid or a pharmaceutically acceptable salt thereof, an anti-fungal agent, an excipient base powder, and xylitol can comprise about 0.0256 g mupirocin, about 0.0012 g corticosteroid or a pharmaceutically acceptable salt thereof, about 0.0038 g anti-fungal agent, about 0.0918 g excipient base powder, and about 0.879 g xylitol.

Mupirocin is known to the art and is discussed supra. In an aspect, mupirocin can be mupirocin USP 95.41. Corticosteroids as well as the pharmaceutically acceptable salts thereof are known to the art and are discussed supra. In an aspect, a corticosteroid can be betamethasone sodium phosphate. Anti-fungal agents are known to the art and are discussed supra. In an aspect, an anti-fungal agent can comprise clotrimazole. Excipient base powders are known to the art and are discussed supra. In an aspect, an excipient base powder can be LoxaSperse™ excipient base powder or XyliFos™ excipient base powder. Xylitol is known to the art and is discussed supra.

In an aspect, a disclosed dry formulation comprising mupirocin, a corticosteroid or a pharmaceutically acceptable salt thereof, and an anti-fungal agent can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising mupirocin, a corticosteroid or a pharmaceutically acceptable salt thereof, and an anti-fungal agent can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising mupirocin, a corticosteroid or a pharmaceutically acceptable salt thereof, and an anti-fungal agent can be encapsulated in a capsule or in one or more capsules. In an aspect, each capsule can comprise about 2.0% mupirocin, about 0.1% corticosteroid or a pharmaceutically acceptable salt thereof, about 0.3% anti-fungal agent, about 7.16% excipient base powder, and about 68.6% xylitol. In an aspect, each capsule can comprise about 0.02 g mupirocin, about 0.001 g corticosteroid or a pharmaceutically acceptable salt thereof, about 0.003 g anti-fungal agent, about 0.0716 g excipient base powder, and about 0.659 g xylitol.

In an aspect, the disclosed dry formulation comprising mupirocin, a corticosteroid or a pharmaceutically acceptable salt thereof, and an anti-fungal agent can be combined with a diluent to generate a homogenous compounded composition (i.e., a compounded solution or suspension). In an aspect, the disclosed dry formulation comprising mupirocin, a corticosteroid or a pharmaceutically acceptable salt thereof, an anti-fungal agent, an excipient base powder, and xylitol can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

4. Mupirocin, Betamethasone Sodium Phosphate, and Clotrimazole

Disclosed herein is a dry formulation comprising a therapeutically effective amount of mupirocin, a therapeutically effective amount of betamethasone sodium phosphate, and a therapeutically effective amount of clotrimazole. Disclosed herein is a dry formulation comprising a therapeutically effective amount of mupirocin, a therapeutically effective amount of betamethasone sodium phosphate, a therapeutically effective amount of clotrimazole, a sufficient amount of an excipient base powder, and a sufficient amount of xylitol.

In an aspect, a disclosed dry formulation comprising mupirocin, betamethasone sodium phosphate, and clotrimazole can comprise mupirocin and betamethasone sodium phosphate in a ratio from about a 1:0.01 to about 1:0.2. In an aspect, a disclosed dry formulation comprising mupirocin, betamethasone sodium phosphate, and clotrimazole can comprise mupirocin and the betamethasone in a ratio of about 1:0.05. In an aspect, a disclosed dry formulation comprising mupirocin, betamethasone sodium phosphate, and clotrimazole can comprise mupirocin and clotrimazole in a ratio from about 1:0.1 to about 1:0.3. In an aspect, a disclosed dry formulation comprising mupirocin, betamethasone sodium phosphate, and clotrimazole can comprise mupirocin and clotrimazole in a ratio of about 1:0.15. In an aspect, a disclosed dry formulation comprising mupirocin, betamethasone sodium phosphate, and clotrimazole agent can comprise betamethasone sodium phosphate and clotrimazole in a ratio from about 1:1 to about 1:5. In an aspect, a disclosed dry formulation comprising mupirocin, betamethasone sodium phosphate, and clotrimazole can comprise betamethasone sodium phosphate and clotrimazole in a ratio of about 1:3. In an aspect, a disclosed dry formulation comprising mupirocin, betamethasone sodium phosphate, and clotrimazole can comprise the excipient base powder and xylitol in a ratio from about 1:9 to about 1:10. In an aspect, a disclosed dry formulation comprising mupirocin, betamethasone sodium phosphate, and clotrimazole can comprise the excipient base powder and xylitol in about a ratio of about 1:9.6.

In an aspect, 1 g of the dry formulation comprising mupirocin, betamethasone, clotrimazole, an excipient base powder, and xylitol can comprise about 0.0256 g mupirocin, about 0.0012 g betamethasone sodium phosphate, about 0.0038 g clotrimazole, about 0.0918 g an excipient base powder, and about 0.879 g xylitol.

Mupirocin is known to the art and is discussed supra. In an aspect, mupirocin can be mupirocin USP 95.41. Betamethasone sodium phosphate is known to the art and is discussed supra. Bethamethasone sodium phosphate can be betamethasone sodium phosphate USP 90.94. Clotrimazole is known to the art and is discussed supra. In an aspect, clotrimazole can be clotrimazole USP 100.2. Excipient base powders are known to the art and are discussed supra. In an aspect, an excipient base powder can be LoxaSperse™ excipient base powder or XyliFos™ excipient base powder. Xylitol is known to the art and is discussed supra.

In an aspect, a disclosed dry formulation comprising mupirocin, betamethasone sodium phosphate, and clotrimazole can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising mupirocin, betamethasone sodium phosphate, and clotrimazole can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising mupirocin, betamethasone sodium phosphate, and clotrimazole can be encapsulated in a capsule or in one or more capsules. In an aspect, each capsule can comprise about 2.0% mupirocin, about 0.1% betamethasone sodium phosphate, about 0.3% clotrimazole, about 7.16% excipient base powder, and about 68.6% xylitol. In an aspect, each capsule can comprise about 0.02 g mupirocin, about 0.001 g betamethasone sodium phosphate, about 0.003 g clotrimazole, about 0.0716 g excipient base powder, and about 0.686 g xylitol. In an aspect, each capsule can comprise about 20 mg mupirocin, about 0.750 mg betamethasone sodium phosphate, and about 3 mg clotrimazole.

In an aspect, the disclosed dry formulation comprising mupirocin, betamethasone sodium phosphate, and clotrimazole can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, the disclosed dry formulation comprising mupirocin, betamethasone sodium phosphate, clotrimazole, an excipient base powder, and xylitol can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

5. Clotrimazole and an Excipient Base Powder

Disclosed herein is a dry formulation comprising a therapeutically effective amount of clotrimazole and a sufficient amount of an excipient base powder. Disclosed herein is a dry formulation comprising a therapeutically effective amount of clotrimazole, a sufficient amount of an excipient base powder, and a therapeutically effective amount of ceftriaxone.

In an aspect, a disclosed dry formulation comprising clotrimazole and an excipient base powder can comprise clotrimazole and the excipient base powder in a ratio from about 1:65 to about 1:75. In an aspect, a disclosed dry formulation comprising clotrimazole and an excipient base powder can comprise clotrimazole and the excipient base powder in a ratio of about 1:70.5.

In an aspect, 1 g of the dry formulation comprising clotrimazole and an excipient base powder can comprise about 0.014 g clotrimazole and about 0.992 g excipient base powder.

Clotrimazole is known to the art and is discussed supra. In an aspect, clotrimazole can be clotrimazole USP 100.2. Excipient base powders are known to the art and are discussed supra. In an aspect, an excipient base powder can be LoxaSperse™ excipient base powder or XyliFos™ excipient base powder. Ceftriaxone is known to the art and is discussed supra. In an aspect, ceftriaxone can be commercially available.

In an aspect, a disclosed dry formulation comprising clotrimazole and an excipient base powder can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising clotrimazole and an excipient base powder can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising clotrimazole and an excipient base powder can be encapsulated in a capsule or in one or more capsules. In an aspect, each capsule can comprise about 1.0% clotrimazole and about 70.5% excipient base powder. In an aspect, each capsule can comprise about 0.01 g clotrimazole and about 0.705 g excipient base powder.

In an aspect, the disclosed dry formulation comprising clotrimazole and an excipient base powder can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

6. Clotrimazole, an Excipient Base Powder, and Xylitol

Disclosed herein is a dry formulation comprising a therapeutically effective amount of clotrimazole, a sufficient amount of an excipient base powder, and a sufficient amount of xylitol. Disclosed herein is a dry formulation comprising a therapeutically effective amount of clotrimazole, a sufficient amount of an excipient base powder, a sufficient amount of xylitol, and a therapeutically effective amount of ceftriaxone.

In an aspect, a disclosed dry formulation comprising clotrimazole, an excipient base powder, and xylitol can comprise clotrimazole and the excipient base powder in a ratio from about 1:7 to about 1:7.5. In an aspect, a disclosed dry formulation comprising clotrimazole, an excipient base powder, and xylitol can comprise clotrimazole and the excipient base powder in a ratio of about 1:7.16. In an aspect, a disclosed dry formulation comprising clotrimazole, an excipient base powder, and xylitol can comprise clotrimazole and xylitol in a ratio from about 1:70 to about 1:75. In an aspect, a disclosed dry formulation comprising clotrimazole, an excipient base powder, and xylitol can comprise clotrimazole and xylitol in about a ratio of about 1:72.6. In an aspect, a disclosed dry formulation comprising clotrimazole, an excipient base powder, and xylitol can comprise the excipient base powder and xylitol in a ratio from about 1:9 to about 1:12. In an aspect, a disclosed dry formulation comprising clotrimazole, an excipient base powder, and xylitol can comprise the excipient base powder and xylitol in about a ratio of about 1:10.14. In an aspect, 1 g of the dry formulation comprising clotrimazole, an excipient base powder, and xylitol can comprise about 0.01234 g clotrimazole, about 0.08839 g an excipient base powder, and about 0.8962 g xylitol.

Clotrimazole is known to the art and is discussed supra. In an aspect, clotrimazole can be clotrimazole USP 100.2. Excipient base powders are known to the art and are discussed supra. In an aspect, an excipient base powder can be LoxaSperse™ excipient base powder or XyliFos™ excipient base powder. Xylitol is known to the art and is discusses supra. Ceftriaxone is known to the art and is discussed supra. In an aspect, ceftriaxone can be commercially available.

In an aspect, a disclosed dry formulation comprising clotrimazole, an excipient base powder, and xylitol can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising clotrimazole, an excipient base powder, and xylitol can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising clotrimazole, an excipient base powder, and xylitol can be encapsulated in a capsule or in one or more capsules. In an aspect, each capsule can comprise about 1.0% clotrimazole, about 7.16% excipient base powder, and about 72.6% xylitol. In an aspect, each capsule can comprise about 0.01 g clotrimazole, about 0.0716 g excipient base powder, and about 0.726 g xylitol.

In an aspect, the disclosed dry formulation comprising clotrimazole, an excipient base powder, and xylitol can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

7. Clotrimazole, a Corticosteroid or a Salt Thereof, an Excipient Base Powder, and Xylitol Disclosed herein is a dry formulation comprising a therapeutically effective amount of clotrimazole, a therapeutically effective amount of a corticosteroid or a pharmaceutically acceptable salt thereof, a sufficient amount of an excipient base powder, and a sufficient amount of xylitol.

In an aspect, a disclosed dry formulation comprising clotrimazole, a corticosteroid or a pharmaceutically acceptable salt thereof, an excipient base powder, and xylitol can comprise clotrimazole and the corticosteroid or a salt thereof in a ratio from about 1:0.1 to about 1:0.5. In an aspect, a disclosed dry formulation comprising clotrimazole, a corticosteroid, an excipient base powder, and xylitol can comprise clotrimazole and the corticosteroid or a salt thereof in a ratio of about 1:0.33. In an aspect, a disclosed dry formulation comprising clotrimazole, a corticosteroid or a pharmaceutically acceptable salt thereof, an excipient base powder, and xylitol can comprise the excipient base powder and xylitol in a ratio from about 1:9 to about 1:12. In an aspect, a disclosed dry formulation comprising clotrimazole, a corticosteroid or a pharmaceutically acceptable salt thereof, an excipient base powder, and xylitol can comprise the excipient base powder and xylitol in about a ratio of about 1:10.23.

In an aspect, 1 g of the dry formulation comprising clotrimazole, a corticosteroid or a pharmaceutically acceptable salt thereof, an excipient base powder, and xylitol can comprise about 0.0037 g clotrimazole, about 0.0012 g corticosteroid or a pharmaceutically acceptable salt thereof, 0.08839 g excipient base powder, and about 0.9049 g xylitol.

Clotrimazole is known to the art and is discussed supra. In an aspect, clotrimazole can be clotrimazole USP 100.2. Corticosteroids as well as the pharmaceutically acceptable salts thereof are known to the art and are discussed supra. In an aspect, the corticosteroid can be betamethasone sodium phosphate. In an aspect, betamethasone sodium phosphate can be betamethasone sodium phosphate USP 90.94. Excipient base powders are known to the art and are discussed supra. In an aspect, an excipient base powder can be LoxaSperse™ excipient base powder or XyliFos™ excipient base powder. Xylitol is known to the art and is discussed supra.

In an aspect, a disclosed dry formulation comprising clotrimazole, a corticosteroid or a pharmaceutically acceptable salt thereof, an excipient base powder, and xylitol can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising clotrimazole, a corticosteroid or a pharmaceutically acceptable salt thereof, an excipient base powder, and xylitol can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising clotrimazole, a corticosteroid or a pharmaceutically acceptable salt thereof, an excipient base powder, and xylitol can be encapsulated in a capsule or in one or more capsules. In an aspect, each capsule can comprise about 0.3% clotrimazole, about 0.1% corticosteroid, about 7.16% excipient base powder, and about 73.3% xylitol. In an aspect, each capsule can comprise about 0.003 g clotrimazole, about 0.001 g corticosteroid or a pharmaceutically acceptable salt thereof, about 0.0716 g excipient base powder, and about 0.733 g xylitol.

In an aspect, the disclosed dry formulation comprising clotrimazole, a corticosteroid or a pharmaceutically acceptable salt thereof, an excipient base powder, and xylitol can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

8. Clotrimazole, Betamethasone Sodium Phosphate, an Excipient Base Powder, and Xylitol Disclosed herein is a dry formulation comprising a therapeutically effective amount of clotrimazole, a therapeutically effective amount of betamethasone sodium phosphate, a sufficient amount of an excipient base powder, and a sufficient amount of xylitol.

In an aspect, a disclosed dry formulation comprising clotrimazole, betamethasone sodium phosphate, an excipient base powder, and xylitol can comprise clotrimazole and betamethasone sodium phosphate in a ratio from about 1:0.1 to about 1:0.5. In an aspect, a disclosed dry formulation comprising clotrimazole, betamethasone sodium phosphate, an excipient base powder, and xylitol can comprise clotrimazole and the excipient base powder in a ratio of about 1:0.33. In an aspect, a disclosed dry formulation comprising clotrimazole, betamethasone sodium phosphate, an excipient base powder, and xylitol can comprise the excipient base powder and xylitol in a ratio from about 1:9 to about 1:12. In an aspect, a disclosed dry formulation comprising clotrimazole, betamethasone sodium phosphate, an excipient base powder, and xylitol can comprise the excipient base powder and xylitol in about a ratio of about 1:10.23.

In an aspect, 1 g of the dry formulation comprising clotrimazole, betamethasone sodium phosphate, an excipient base powder, and xylitol can comprise about 0.0037 g clotrimazole, about 0.0012 g betamethasone sodium phosphate, about 0.08839 g of an excipient base powder, and about 0.9049 g of xylitol.

Clotrimazole is known to the art and is discussed supra. In an aspect, clotrimazole can be clotrimazole USP 100.2. Betamethasone sodium phosphate is known to the art and is discussed supra. In an aspect, betamethasone sodium phosphate can be betamethasone sodium phosphate USP 90.94. Excipient base powders are known to the art and are discussed supra. In an aspect, an excipient base powder can be LoxaSperse™ excipient base powder or XyliFos™ excipient base powder. Xylitol is known to the art and is discussed supra.

In an aspect, a disclosed dry formulation comprising clotrimazole, betamethasone sodium phosphate, an excipient base powder, and xylitol can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising clotrimazole, betamethasone sodium phosphate, an excipient base powder, and xylitol can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising mupirocin, betamethasone sodium phosphate, an excipient base powder, and xylitol can be encapsulated in a capsule or in one or more capsules. In an aspect, each capsule can comprise about 0.3% clotrimazole, about 0.1% betamethasone sodium phosphate, about 7.16% excipient base powder, and about 73.3% xylitol. In an aspect, each capsule can comprise about 0.003 g clotrimazole, about 0.001 g betamethasone sodium phosphate, about 0.0716 g excipient base powder, and about 0.733 g xylitol. In an aspect, each capsule can comprise 0.750 mg betamethasone sodium phosphate and 3 mg clotrimazole.

In an aspect, the disclosed dry formulation comprising clotrimazole, betamethasone sodium phosphate, an excipient base powder, and xylitol can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation comprising can be stored at room temperature.

9. Doxycycline or a Salt Thereof, a Corticosteroid or a Salt Thereof, and an Anti-Fungal Agent Disclosed herein is a dry formulation comprising a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent. Disclosed herein is a dry formulation comprising a therapeutically effective amount of doxycycline or a pharmaceutically acceptable salt thereof, a therapeutically effective amount of an corticosteroid or a pharmaceutically acceptable salt thereof, a therapeutically effective amount of clotrimazole, a sufficient amount of an excipient base powder, and a sufficient amount of xylitol.

In an aspect, a disclosed dry formulation comprising doxycycline or a pharmaceutically acceptable salt thereof, a corticosteroid or a pharmaceutically acceptable salt thereof, and an anti-fungal agent can comprise doxycycline or a salt thereof and the corticosteroid or a salt thereof in a ratio from about a 1:0.01 to about 1:0.06. In an aspect, a disclosed dry formulation comprising doxycycline or a pharmaceutically acceptable salt thereof, a corticosteroid or a pharmaceutically acceptable salt thereof, and an anti-fungal agent can comprise doxycycline or a salt thereof and the corticosteroid or a salt thereof in a ratio of about 1:0.033. In an aspect, a disclosed dry formulation comprising doxycycline or a pharmaceutically acceptable salt thereof, a corticosteroid or a pharmaceutically acceptable salt thereof, and an anti-fungal agent can comprise doxycycline or a salt thereof and an anti-fungal agent in a ratio from about 1:0.05 to about 1:1. In an aspect, a disclosed dry formulation comprising doxycycline or a pharmaceutically acceptable salt thereof, a corticosteroid or a pharmaceutically acceptable salt thereof, and an anti-fungal agent can comprise doxycycline or a salt thereof and an anti-fungal agent in a ratio of about 1:0.1. In an aspect, a disclosed dry formulation comprising doxycycline or a pharmaceutically acceptable salt thereof, a corticosteroid or a pharmaceutically acceptable salt thereof, and an anti-fungal agent can comprise a corticosteroid or a salt thereof and an anti-fungal agent in a ratio from about 1:1 to about 1:6. In an aspect, a disclosed dry formulation comprising doxycycline or a pharmaceutically acceptable salt thereof, a corticosteroid or a pharmaceutically acceptable salt thereof, and an anti-fungal agent can comprise a corticosteroid or a salt thereof and an anti-fungal agent in a ratio of about 1:3. In an aspect, a disclosed dry formulation comprising doxycycline or a pharmaceutically acceptable salt thereof, a corticosteroid or a pharmaceutically acceptable salt thereof, and an anti-fungal agent can comprise the excipient base powder and xylitol in a ratio from about 1:0.1 to about 1:2. In an aspect, a disclosed dry formulation comprising doxycycline or a pharmaceutically acceptable salt thereof, a corticosteroid or a pharmaceutically acceptable salt thereof, and an anti-fungal agent can comprise the excipient base powder and xylitol in about a ratio of about 1:1.08.

In an aspect, 1 g of the dry formulation comprising doxycycline or a pharmaceutically acceptable salt thereof, a corticosteroid or a pharmaceutically acceptable salt thereof, an anti-fungal agent, an excipient base powder, and xylitol can comprise about 0.0394 g doxycycline or a pharmaceutically acceptable salt thereof, about 0.0013 g corticosteroid or a pharmaceutically acceptable salt thereof, about 0.0039 g anti-fungal agent, about 0.4605 g an excipient base powder, and about 0.4986 g xylitol.

Doxycycline as well as its pharmaceutically acceptable salts thereof are known to the art and are discussed supra. In an aspect, doxycycline can be doxycycline hyclate USP 83.97. Corticosteroids as well as their pharmaceutically acceptable salts thereof are known to the art and discussed supra. In an aspect, a corticosteroid can be betamethasone sodium phosphate USP 90.94. Anti-fungal agents are known to the art and discussed supra. In an aspect, an anti-fungal agent can be clotrimazole USP 100.2. Excipient base powders are known to the art and are discussed supra. In an aspect, an excipient base powder can be LoxaSperse™ excipient base powder or XyliFos™ excipient base powder. Xylitol is known to the art and is discussed supra.

In an aspect, a disclosed dry formulation comprising doxycycline or a pharmaceutically acceptable salt thereof, a corticosteroid or a pharmaceutically acceptable salt thereof, and clotrimazole can comprise one or more excipients or additives. In an aspect, a disclosed dry formulation comprising doxycycline or a pharmaceutically acceptable salt thereof, a corticosteroid or a pharmaceutically acceptable salt thereof, clotrimazole, an excipient base powder, and xylitol can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising doxycycline or a pharmaceutically acceptable salt thereof, a corticosteroid or a pharmaceutically acceptable salt thereof, and clotrimazole can comprise a therapeutically effective amount of one or more additional active agents. In an aspect, a disclosed dry formulation comprising doxycycline or a pharmaceutically acceptable salt thereof, a corticosteroid or a pharmaceutically acceptable salt thereof, clotrimazole, an excipient base powder, and xylitol can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising doxycycline or a pharmaceutically acceptable salt thereof, a corticosteroid or a pharmaceutically acceptable salt thereof, and an anti-fungal agent can be encapsulated in a capsule or in one or more capsules. In an aspect, a disclosed dry formulation comprising doxycycline or a pharmaceutically acceptable salt thereof, a 5 corticosteroid or a pharmaceutically acceptable salt thereof, an anti-fungal agent, an excipient base powder, and xylitol can be encapsulated in a capsule or in one or more capsules.

In an aspect, each capsule can comprise about 0.03 g doxycycline or a pharmaceutically acceptable salt thereof, about 0.001 g corticosteroid or a pharmaceutically acceptable salt thereof, and about 0.003 g an anti-fungal agent. In an aspect, each capsule can comprise about 0.03 g doxycycline or a pharmaceutically acceptable salt thereof, about 0.001 g corticosteroid or a pharmaceutically acceptable salt thereof, about 0.003 g anti-fungal agent, about 0.35 g excipient base powder, and about 0.379 g xylitol. In an aspect, each capsule can comprise about 3% doxycycline or a pharmaceutically acceptable salt thereof, and about 0.1% corticosteroid or a pharmaceutically acceptable salt thereof. In an aspect, each capsule can comprise about 3% doxycycline or a pharmaceutically acceptable salt thereof, about 0.1% corticosteroid or a pharmaceutically acceptable salt thereof, about 0.3% anti-fungal agent, about 35% excipient base powder, and about 37.9% xylitol.

In an aspect, the disclosed dry formulation comprising doxycycline or a pharmaceutically acceptable salt thereof, a corticosteroid or a pharmaceutically acceptable salt thereof, and an anti-fungal agent can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, the disclosed dry formulation comprising doxycycline or a pharmaceutically acceptable salt thereof, a corticosteroid or a pharmaceutically acceptable salt thereof, an anti-fungal agent, an excipient base powder, and xylitol can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

10. Doxycycline Hyclate, Betamethasone Sodium Phosphate, and Clotrimazole

Disclosed herein is a dry formulation comprising a therapeutically effective amount of doxycycline hyclate, a therapeutically effective amount of betamethasone sodium phosphate, a therapeutically effective amount of clotrimazole, a sufficient amount of an excipient base powder, and a sufficient amount of xylitol.

In an aspect, a disclosed dry formulation comprising doxycycline hyclate, betamethasone sodium phosphate, and clotrimazole can comprise doxycycline hyclate and betamethasone sodium phosphate in a ratio from about a 1:0.01 to about 1:0.06. In an aspect, a disclosed dry formulation comprising doxycycline hyclate, betamethasone sodium phosphate, and clotrimazole can comprise doxycycline hyclate and betamethasone sodium phosphate in a ratio of about 1:0.033. In an aspect, a disclosed dry formulation comprising doxycycline hyclate, betamethasone sodium phosphate, and clotrimazole can comprise doxycycline hyclate and clotrimazole in a ratio from about 1:0.05 to about 1:1. In an aspect, a disclosed dry formulation comprising doxycycline hyclate, betamethasone sodium phosphate, and clotrimazole can comprise doxycycline hyclate and clotrimazole in a ratio of about 1:0.1. In an aspect, a disclosed dry formulation comprising doxycycline hyclate, betamethasone sodium phosphate, and clotrimazole agent can comprise betamethasone sodium phosphate and clotrimazole in a ratio from about 1:1 to about 1:6. In an aspect, a disclosed dry formulation comprising doxycycline hyclate, betamethasone sodium phosphate, and clotrimazole can comprise betamethasone sodium phosphate and clotrimazole in a ratio of about 1:3. In an aspect, a disclosed dry formulation comprising doxycycline hyclate, betamethasone sodium phosphate, and clotrimazole can comprise the excipient base powder and xylitol in a ratio from about 1:0.1 to about 1:2. In an aspect, a disclosed dry formulation comprising doxycycline hyclate, betamethasone sodium phosphate, and clotrimazole can comprise the excipient base powder and xylitol in about a ratio of about 1:1.08.

In an aspect, 1 g of the dry formulation comprising doxycycline hyclate, betamethasone sodium phosphate, clotrimazole, an excipient base powder, and xylitol can comprise about 0.0394 g doxycycline hyclate, about 0.0013 g betamethasone sodium phosphate, about 0.0039 g clotrimazole, about 0.4605 g the excipient base powder, and about 0.4986 g xylitol.

Doxycycline hyclate is known to the art and is discussed supra. In an aspect, doxycycline hyclate can be commercially available, for example, as 100 mg tablets. Betamethasone sodium phosphate is known to the art and is discussed supra. In an aspect, betamethasone sodium phosphate can be betamethasone sodium phosphate USP 90.94. Clotrimazole is known to the art and is discussed supra. In an aspect, clotrimazole can be clotrimazole USP 100.2. In an aspect, clotrimazole can comprise a 10 mg troche. Excipient base powders are known to the art and are discussed supra.

In an aspect, an excipient base powder can be LoxaSperse™ excipient base powder or XyliFos™ excipient base powder. Xylitol is known to the art and is discussed supra.

In an aspect, a disclosed dry formulation comprising doxycycline hyclate, betamethasone sodium phosphate, clotrimazole, an excipient base powder, and xylitol can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising doxycycline hyclate, betamethasone sodium phosphate, clotrimazole, an excipient base powder, and xylitol can comprise can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising doxycycline hyclate, betamethasone sodium phosphate, clotrimazole, an excipient base powder, and xylitol can be encapsulated in a capsule or in one or more capsules. In an aspect, each capsule can comprise about 0.03 g doxycycline hyclate, about 0.001 g betamethasone sodium phosphate, about 0.003 g clotrimazole, about 0.35 g excipient base powder, and about 0.379 g xylitol. In an aspect, each capsule can comprise about 3.0% doxycycline hyclate, about 0.1% betamethasone sodium phosphate, about 0.3% clotrimazole, about 35.0% excipient base powder, and about 37.9% xylitol. In an aspect, each capsule can comprise about 30 mg doxycycline hyclate, about 0.750 mg betamethasone sodium phosphate, and about 3 mg clotrimazole.

In an aspect, the disclosed dry formulation comprising doxycycline hyclate, betamethasone sodium phosphate, and clotrimazole can be combined with a diluent to generate a homogenous compounded composition (i.e., a compounded solution or suspension). In an aspect, the disclosed dry formulation comprising doxycycline hyclate, betamethasone sodium phosphate, clotrimazole, an excipient base powder, and xylitol can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

11. Doxycycline Hyclate, Dexamethasone, and Clotrimazole

Disclosed herein is a dry formulation comprising a therapeutically effective amount of doxycycline hyclate, a therapeutically effective amount of dexamethasone, and a therapeutically effective amount of clotrimazole. Disclosed herein is a dry formulation comprising a therapeutically effective amount of doxycycline hyclate, a therapeutically effective amount of a dexamethasone, a therapeutically effective amount of clotrimazole, a sufficient amount of an excipient base powder and a sufficient amount of xylitol.

In an aspect, a disclosed dry formulation comprising doxycycline hyclate, dexamethasone, and clotrimazole can comprise doxycycline hyclate and dexamethasone in a ratio from about a 1:0.01 to about 1:0.1. In an aspect, a disclosed dry formulation comprising doxycycline hyclate, dexamethasone, and clotrimazole can comprise doxycycline hyclate and dexamethasone in a ratio of about 1:0.017. In an aspect, a disclosed dry formulation comprising doxycycline hyclate, dexamethasone, and clotrimazole can comprise doxycycline hyclate and clotrimazole in a ratio from about 1:0.01 to about 1:1. In an aspect, a disclosed dry formulation comprising doxycycline hyclate, dexamethasone, and clotrimazole can comprise doxycycline hyclate and clotrimazole in a ratio of about 1:0.02. In an aspect, a disclosed dry formulation comprising doxycycline hyclate, dexamethasone, and clotrimazole agent can comprise dexamethasone and clotrimazole in a ratio from about 1:1 to about 1:3. In an aspect, a disclosed dry formulation comprising doxycycline hyclate, dexamethasone, and clotrimazole can comprise dexamethasone and clotrimazole in a ratio of about 1:1.23.

Doxycycline hyclate is known to the art and is discussed supra. In an aspect, doxycycline can be doxycycline hyclate. In an aspect, doxycycline hyclate can be commercially available, for example, as 100 mg tablets. Dexamethasone is known to the art and is discussed supra. In an aspect, dexamethasone can comprise dexamethasone USP (e.g., a 6 mg tablets). Clotrimazole is known to the art and is discussed supra. In an aspect, clotrimazole can be clotrimazole USP 100.2. Excipient base powders are known to the art and are discussed supra. In an aspect, an excipient base powder can be LoxaSperse™ excipient base powder or XyliFos™ excipient base powder. Xylitol is known to the art and is discussed supra.

In an aspect, a disclosed dry formulation comprising doxycycline hyclate, dexamethasone, and clotrimazole can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed dry formulation comprising doxycycline hyclate, dexamethasone, and clotrimazole can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed dry formulation comprising doxycycline hyclate, dexamethasone, and clotrimazole can be encapsulated in a capsule or in one or more capsules. In an aspect, each capsule can comprise about 0.1175 g doxycycline hyclate, about 0.02 g dexamethasone, and about 0.0246 g clotrimazole.

In an aspect, the disclosed dry formulation comprising doxycycline hyclate, dexamethasone, and clotrimazole can be combined with a diluent to generate a homogenous compounded composition (i.e., a compounded solution or suspension). Diluents are known to the art and are discussed supra. For example, in an aspect, a diluent can be a hydrocortisone/acetic acid otic solution or a sodium chloride solution.

In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject. In an aspect, a disclosed dry formulation can be stored at room temperature.

12. Miscellaneous

Disclosed herein is a dry formulation comprising a therapeutically effective amount of azithromycin, a therapeutically effective amount of fluticasone, and a therapeutically effective amount of fluconazole. Disclosed herein is a dry formulation comprising a therapeutically effective amount of azithromycin, a therapeutically effective amount of fluticasone, a therapeutically effective amount of fluconazole, a sufficient amount of an excipient base powder, and a sufficient amount of xylitol. In an aspect, a disclosed dry formulation can comprise about 1 mg to about 50 mg azithromycin, about 1 mg to about 5 mg fluticasone, and about 1 mg to about 50 mg fluconazole. In an aspect, a disclosed dry formulation can comprise about 5.0% azithromycin, about 1.5% fluticasone, and about 1.5% fluconazole. In an aspect, a disclosed dry formulation comprising azithromycin, fluticasone, and fluconazole can be combined with a hydrocortisone/acetic acid otic solution to generate a homogenous compounded composition (i.e., a compounded solution or suspension). In an aspect, a disclosed dry formulation comprising azithromycin, fluticasone, and fluconazole can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of sulfamethoxazole, a therapeutically effective amount of trimethoprim, a therapeutically effective amount of fluticasone, and a therapeutically effective amount of fluconazole. Disclosed herein is a dry formulation comprising a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol. In an aspect, a disclosed dry formulation can comprise about 1 mg to about 180 mg sulfamethoxazole, about 1 mg to about 50 mg trimethoprim, about 1 mg to about 5 mg fluticasone, and about 1 mg to about 50 mg fluconazole. In an aspect, a disclosed dry formulation can comprise about 8.0% sulfamethoxazole, about 5.0% trimethoprim, about 1.5% fluticasone, and about 1.5% fluconazole. In an aspect, a disclosed dry formulation comprising sulfamethoxazole, trimethoprim, fluticasone, and fluconazole can be combined with a hydrocortisone/acetic acid otic solution to generate a homogenous compounded composition (i.e., a compounded solution or suspension). In an aspect, a disclosed dry formulation comprising sulfamethoxazole, trimethoprim, fluticasone, and fluconazole can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of levofloxacin hemihydrate, a therapeutically effective amount of fluticasone, and a therapeutically effective amount of fluconazole. Disclosed herein is a dry formulation comprising a therapeutically effective amount of levofloxacin hemihydrate, a therapeutically effective amount of fluticasone, a therapeutically effective amount of fluconazole, a sufficient amount of an excipient base powder, and a sufficient amount of xylitol. In an aspect, a disclosed dry formulation can comprise about 1 mg to about 150 mg levofloxacin hemihydrate, about 1 mg to about 5 mg fluticasone, and about 1 mg to about 50 mg fluconazole. In an aspect, a disclosed dry formulation can comprise about 12.8% levofloxacin hemihydrate, about 1.5% fluticasone, and about 1.5% fluconazole. In an aspect, a disclosed dry formulation comprising levofloxacin hemihydrate, fluticasone, and fluconazole can be combined with a hydrocortisone/acetic acid otic solution to generate a homogenous compounded composition (i.e., a compounded solution or suspension). In an aspect, a disclosed dry formulation comprising levofloxacin hemihydrate, fluticasone, and fluconazole can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of fluticasone and a therapeutically effective amount of fluconazole. Disclosed herein is a dry formulation comprising a therapeutically effective amount of fluticasone, a therapeutically effective amount of fluconazole, a sufficient amount of an excipient base powder, and a sufficient amount of xylitol. In an aspect, a disclosed dry formulation can comprise about 1 mg to about 5 mg fluticasone and about 1 mg to about 50 mg fluconazole. In an aspect, a disclosed dry formulation can comprise about 1.5% fluticasone and about 1.5% fluconazole. In an aspect, a disclosed dry formulation comprising fluticasone and fluconazole can be combined with a hydrocortisone/acetic acid otic solution to generate a homogenous compounded composition (i.e., a compounded solution or suspension). In an aspect, a disclosed dry formulation comprising fluticasone and fluconazole can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of vancomycin hydrochloride and a therapeutically effective amount of mupirocin. Disclosed herein is a dry formulation comprising a therapeutically effective amount of vancomycin hydrochloride, a therapeutically effective amount of mupirocin, a sufficient amount of an excipient base powder, and a sufficient amount of xylitol. In an aspect, a disclosed dry formulation can comprise about 1 mg to about 100 mg vancomycin hydrochloride and about 1 mg to about 200 mg mupirocin. In an aspect, a disclosed dry formulation can comprise about 5.15% vancomycin hydrochloride and about 20% mupirocin. In an aspect, the disclosed dry formulation comprising vancomycin hydrochloride and mupirocin can be combined with a hydrocortisone/acetic acid otic solution to generate a homogenous compounded composition (i.e., a compounded solution or suspension). In an aspect, the disclosed dry formulation comprising vancomycin hydrochloride and mupirocin can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of mupirocin and a therapeutically effective amount of clotrimazole. Disclosed herein is a dry formulation comprising a therapeutically effective amount of mupirocin, a therapeutically effective amount of clotrimazole, a sufficient amount of an excipient base powder, and a sufficient amount of xylitol. In an aspect, a disclosed dry formulation can comprise about 1 mg to about 100 mg mupirocin and about 0.50 mg to about 10 mg clotrimazole. In an aspect, a disclosed dry formulation comprising mupirocin and clotrimazole can be combined with a hydrocortisone/acetic acid otic solution to generate a homogenous compounded composition (i.e., a compounded solution or suspension). In an aspect, a disclosed dry formulation comprising mupirocin and clotrimazole can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of mupirocin, a therapeutically effective amount of clindamycin, and a therapeutically effective amount of clotrimazole. Disclosed herein is a dry formulation comprising a therapeutically effective amount of mupirocin, a therapeutically effective amount of clindamycin, and a therapeutically effective amount of clotrimazole, a sufficient amount of an excipient base powder, and a sufficient amount of xylitol. In an aspect, a disclosed dry formulation can comprise about 1 mg to about 100 mg mupirocin, about 1 mg to about 100 mg clindamycin, and about 0.50 mg to about 10 mg clotrimazole. In an aspect, a disclosed dry formulation can comprise about 20 mg mupirocin, about 25 mg clindamycin, and about 3 mg clotrimazole. In an aspect, a disclosed dry formulation can comprise about 20 mg mupirocin, about 25 mg clindamycin, about 3 mg clotrimazole, and about 647 mg of an excipient base powder such as LoxaSperse™. In an aspect, a disclosed dry formulation can comprise about 2.0% mupirocin, about 2.5% clindamycin, about 3.0% clotrimazole, and about 64.7% excipient base powder such as LoxaSperse™. In an aspect, a disclosed dry formulation comprising mupirocin, clindamycin, and clotrimazole can be combined with a hydrocortisone/acetic acid otic solution to generate a homogenous compounded composition (i.e., a compounded solution or suspension). In an aspect, a disclosed dry formulation comprising mupirocin, clindamycin, and clotrimazole can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of ceftriaxone. Disclosed herein is a dry formulation comprising a therapeutically effective amount of ceftriaxone, a sufficient amount of an excipient base powder, and a sufficient amount of xylitol. In an aspect, a disclosed dry formulation can comprise about 250 mg to about 750 mg ceftriaxone. In an aspect, a disclosed dry formulation can comprise about 500 mg ceftriaxone. In an aspect, a disclosed dry formulation can comprise about 500 mg of ceftriaxone and about 200 mg of an excipient base powder such as LoxaSperse™. In an aspect, a disclosed dry formulation can comprise about 50.0% ceftriaxone and about 20.0% excipient base powder such as LoxaSperse™. In an aspect, the disclosed dry formulation comprising ceftriaxone can be combined with a hydrocortisone/acetic acid otic solution to generate a homogenous compounded composition (i.e., a compounded solution or suspension). In an aspect, a disclosed dry formulation comprising ceftriaxone can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of clotrimazole. Disclosed herein is a dry formulation comprising a therapeutically effective amount of clotrimazole, a sufficient amount of an excipient base powder, and a sufficient amount of xylitol. In an aspect, a disclosed dry formulation can comprise about 5 mg to about 20 mg clotrimazole. In an aspect, a disclosed dry formulation can comprise about 10 mg clotrimazole. In an aspect, a disclosed dry formulation can comprise about 10 mg of clotrimazole and about 705 mg of LoxaSperse™. In an aspect, a disclosed dry formulation can comprise about 1.0% clotrimazole and about 70.5% excipient base powder such as LoxaSperse™. In an aspect, the disclosed dry formulation comprising clotrimazole can be combined with a hydrocortisone/acetic acid otic solution to generate a homogenous compounded composition (i.e., a compounded solution or suspension). In an aspect, a disclosed dry formulation comprising clotrimazole can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

Disclosed herein is a dry formulation comprising a therapeutically effective amount of doxycycline or a pharmaceutically acceptable salt thereof and a therapeutically effective amount of clotrimazole. Disclosed herein is a dry formulation comprising a therapeutically effective amount of doxycycline or a pharmaceutically acceptable salt thereof, a therapeutically effective amount of clotrimazole, a sufficient amount of an excipient base powder, and a sufficient amount of xylitol. In an aspect, a disclosed dry formulation can comprise about 1.0 mg to about 250.0 mg doxycycline or a pharmaceutically acceptable salt thereof and about 1.0 mg to about 10.0 mg clotrimazole. In an aspect, a disclosed dry formulation comprising doxycycline or a pharmaceutically acceptable salt thereof and clotrimazole can be combined with a hydrocortisone/acetic acid otic solution to generate a homogenous compounded composition (i.e., a compounded solution or suspension). In an aspect, a disclosed dry formulation comprising doxycycline or a pharmaceutically acceptable salt thereof and clotrimazole can be combined with a sodium chloride solution to generate a homogenous compounded composition (i.e., a compounded solution or suspension). In an aspect, a disclosed dry formulation can have an established shelf-life of 180 days or about 6 months. In an aspect, a disclosed dry formulation retains its full potency because it is mixed with a diluent (e.g., a hydrocortisone/acetic acid otic solution, a sodium chloride solution, etc.) at the time it is administered to the subject.

D. Compounded Compositions

Disclosed herein are compounded compositions for treating an infection. Disclosed herein are compounded compositions for treating an infection comprising a diluent and a disclosed dry formulation.

1. Mupirocin, an Anti-Bacterial Agent, and an Anti-Fungal Agent

Disclosed herein is a compounded composition comprising a diluent and a dry formulation, wherein the dry formulation comprises a therapeutically effective amount of mupirocin, a therapeutically effective amount of an anti-bacterial agent, and a therapeutically effective amount of an anti-fungal agent. Dry formulations comprising mupirocin, an anti-bacterial agent, and an anti-fungal agent are discussed supra. Disclosed herein is a compounded composition comprising a diluent and a dry formulation, wherein the dry formulation comprises a therapeutically effective amount of mupirocin, a therapeutically effective amount of an anti-bacterial agent, a therapeutically effective amount of an anti-fungal agent, a sufficient amount of an excipient base powder, and a sufficient amount of xylitol. Dry formulations comprising mupirocin, an anti-bacterial agent, an anti-fungal agent, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

2. Mupirocin, Clindamycin Hydrochloride, and Clotrimazole

Disclosed herein is a compounded composition comprising a diluent and a dry formulation, wherein the dry formulation comprises a therapeutically effective amount of mupirocin, a therapeutically effective amount clindamycin hydrochloride, and a therapeutically effective amount of clotrimazole. Dry formulations comprising mupirocin, clindamycin hydrochloride, and clotrimazole are discussed supra. Disclosed herein is a compounded composition comprising a diluent and a dry formulation, wherein the dry formulation comprises a therapeutically effective amount of mupirocin, a therapeutically effective amount of clindamycin hydrochloride, a therapeutically effective amount of clotrimazole, and a sufficient amount of an excipient base powder. Dry formulations comprising mupirocin, clindamycin hydrochloride, clotrimazole, and an excipient base powder are discussed supra. Disclosed herein is a compounded composition comprising a diluent and a dry formulation, wherein the dry formulation comprises a therapeutically effective amount of mupirocin, a therapeutically effective amount of clindamycin hydrochloride, a therapeutically effective amount of clotrimazole, a sufficient amount of an excipient base powder, and a sufficient amount of xylitol. Dry formulations comprising mupirocin, clindamycin hydrochloride, clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

3. Mupirocin, a Corticosteroid or a Salt Thereof, and an Anti-Fungal Agent

Disclosed herein is a compounded composition comprising a diluent and a dry formulation, wherein the dry formulation comprises a therapeutically effective amount of mupirocin, a therapeutically effective amount of a corticosteroid or a pharmaceutically acceptable salt thereof, and a therapeutically effective amount of an anti-fungal agent. Dry formulations comprising mupirocin, a corticosteroid or a pharmaceutically acceptable salt thereof, and an anti-fungal agent are discussed supra. Disclosed herein is a compounded composition comprising a diluent and a dry formulation, wherein the dry formulation comprises a therapeutically effective amount of mupirocin, a therapeutically effective amount of a corticosteroid or a pharmaceutically acceptable salt thereof, a therapeutically effective amount of an anti-fungal agent, a sufficient amount of an excipient base powder, and a sufficient amount of xylitol. Dry formulations comprising mupirocin, a corticosteroid or a pharmaceutically acceptable salt thereof, an anti-fungal agent, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

4. Mupirocin, Betamethasone Sodium Phosphate, and Clotrimazole

Disclosed herein is a compounded composition comprising a diluent and a dry formulation, wherein the dry formulation comprises a therapeutically effective amount of mupirocin, a therapeutically effective amount of betamethasone sodium phosphate, and a therapeutically effective amount of clotrimazole. Dry formulations comprising mupirocin, betamethasone sodium phosphate, and clotrimazole are discussed supra. Disclosed herein is a compounded composition comprising a diluent and a dry formulation, wherein the dry formulation comprises a therapeutically effective amount of mupirocin, a therapeutically effective amount of betamethasone sodium phosphate, a therapeutically effective amount of clotrimazole, a sufficient amount of an excipient base powder, and a sufficient amount of xylitol. Dry formulations comprising mupirocin, betamethasone sodium phosphate, clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

5. Clotrimazole and an Excipient Base Powder

Disclosed herein is a compounded composition comprising a diluent and a dry formulation, wherein the dry formulation comprises a therapeutically effective amount of clotrimazole and a sufficient amount of an excipient base powder. Dry formulations comprising clotrimazole and an excipient base powder are discussed supra. Disclosed herein is a compounded composition comprising a diluent and a dry formulation, wherein the dry formulation comprises a therapeutically effective amount of clotrimazole, a sufficient amount of an excipient base powder, and a therapeutically effective amount of ceftriaxone. Dry formulations comprising clotrimazole, an excipient base powder, and ceftriaxone are discussed supra. Diluents are known to the art and are discussed supra. In an aspect, the diluent can be a hydrocortisone/acetic acid otic solution. In an aspect, the diluent can be a sodium chloride solution.

6. Clotrimazole, an Excipient Base Powder, and Xylitol

Disclosed herein is a compounded composition comprising a diluent and a dry formulation, wherein the dry formulation comprises a therapeutically effective amount of clotrimazole, a sufficient amount of an excipient base powder, and a sufficient amount of xylitol. Dry formulations comprising clotrimazole, an excipient base powder, and xylitol are discussed supra. Disclosed herein is a compounded composition comprising a diluent and a dry formulation, wherein the dry formulation comprises a therapeutically effective amount of clotrimazole, a sufficient amount of an excipient base powder, a sufficient amount of xylitol, and a therapeutically effective amount of ceftriaxone. Dry formulations comprising clotrimazole, an excipient base powder, xylitol, and ceftriaxone are discussed supra. Diluents are known to the art and are discussed supra. In an aspect, the diluent can be a hydrocortisone/acetic acid otic solution. In an aspect, the diluent can be a sodium chloride solution.

7. Clotrimazole, a Corticosteroid or a Salt Thereof, an Excipient Base Powder, and Xylitol Disclosed herein is a compounded composition comprising a diluent and a dry formulation, wherein the dry formulation comprises a therapeutically effective amount of clotrimazole, a therapeutically effective amount of a corticosteroid or a pharmaceutically acceptable salt thereof, a sufficient amount of an excipient base powder, and a sufficient amount of xylitol. Dry formulations comprising clotrimazole, a corticosteroid or a pharmaceutically acceptable salt thereof, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

8. Clotrimazole, Betamethasone Sodium Phosphate, an Excipient Base Powder, and Xylitol Disclosed herein is a compounded composition comprising a diluent and a dry formulation, wherein the dry formulation comprises a therapeutically effective amount of clotrimazole, a therapeutically effective amount of betamethasone sodium phosphate, a sufficient amount of an excipient base powder, and a sufficient amount of xylitol. Dry formulations comprising clotrimazole, betamethasone sodium phosphate, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

9. Doxycycline or a Salt Thereof, a Corticosteroid or Salt Thereof, and Clotrimazole Disclosed herein is a compounded composition comprising a diluent and a dry formulation, wherein the dry formulation comprises a therapeutically effective amount of doxycycline or a pharmaceutically acceptable salt thereof, a therapeutically effective amount of a corticosteroid or a pharmaceutically acceptable salt thereof, and a therapeutically effective amount of clotrimazole. Dry formulations comprising doxycycline or a pharmaceutically acceptable salt thereof, a corticosteroid or a pharmaceutically acceptable salt thereof, and clotrimazole are discussed supra. Disclosed herein is a compounded composition comprising a diluent and a dry formulation, wherein the dry formulation comprises a therapeutically effective amount of doxycycline or a pharmaceutically acceptable salt thereof, a therapeutically effective amount of a corticosteroid or a pharmaceutically acceptable salt thereof, a therapeutically effective amount of clotrimazole, a sufficient amount of an excipient base powder, and a sufficient amount of xylitol. Dry formulations comprising doxycycline or a pharmaceutically acceptable salt thereof, a corticosteroid or a pharmaceutically acceptable salt thereof, clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

10. Doxycycline Hyclate, Betamethasone Sodium Phosphate, and Clotrimazole

Disclosed herein is a compounded composition comprising a diluent and a dry formulation, wherein the dry formulation comprises a therapeutically effective amount of doxycycline hyclate, a therapeutically effective amount of betamethasone sodium phosphate, a therapeutically effective amount of clotrimazole, a sufficient amount of an excipient base powder, and a sufficient amount of xylitol. Dry formulations comprising doxycycline hyclate, betamethasone sodium phosphate, clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

11. Doxycycline Hyclate, Dexamethasone, and Clotrimazole

Disclosed herein is a compounded composition comprising a diluent and a dry formulation, wherein the dry formulation comprises a therapeutically effective amount of doxycycline hyclate, a therapeutically effective amount of dexamethasone, and a therapeutically effective amount of clotrimazole. Dry formulations comprising doxycycline hyclate, dexamethasone, and clotrimazole are discussed supra. Disclosed herein is a compounded composition comprising a diluent and a dry formulation, wherein the dry formulation comprises a therapeutically effective amount of doxycycline hyclate, a therapeutically effective amount of a dexamethasone, a therapeutically effective amount of clotrimazole, a sufficient amount of an excipient base powder, and a sufficient amount of xylitol. Dry formulations comprising doxycycline hyclate, dexamethasone, clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

12. Miscellaneous

Disclosed herein is a compounded composition comprising a diluent and a dry formulation, wherein the dry formulation comprises a therapeutically effective amount of azithromycin, a therapeutically effective amount of fluticasone, and a therapeutically effective amount of fluconazole. Dry formulations comprising azithromycin, fluticasone, and fluconazole are discussed supra. Disclosed herein is a compounded composition comprising a diluent and a dry formulation, wherein the dry formulation comprises a therapeutically effective amount of azithromycin, a therapeutically effective amount of fluticasone, a therapeutically effective amount of fluconazole, a sufficient amount of an excipient base powder, and a sufficient amount of xylitol. Dry formulations comprising azithromycin, fluticasone, fluconazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

Disclosed herein is a compounded composition comprising a diluent and a dry formulation, wherein the dry formulation comprises a therapeutically effective amount of sulfamethoxazole, a therapeutically effective amount of trimethoprim, a therapeutically effective amount of fluticasone, and a therapeutically effective amount of fluconazole. Dry formulations comprising sulfamethoxazole, trimethoprim, fluticasone, and fluconazole are discussed supra. Disclosed herein is a compounded composition comprising a diluent and a dry formulation, wherein the dry formulation comprises a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol. Dry formulations comprising sulfamethoxazole, trimethoprim, fluticasone, fluconazole, an excipient base powder, and xylitol are discussed supra. In an aspect, the diluent can be a hydrocortisone/acetic acid otic solution. Diluents are known to the art and are discussed supra. In an aspect, the diluent can be a sodium chloride solution.

Disclosed herein is a compounded composition comprising a diluent and a dry formulation, wherein the dry formulation comprises a therapeutically effective amount of levofloxacin hemihydrate, a therapeutically effective amount of fluticasone, and a therapeutically effective amount of fluconazole. Dry formulations comprising levofloxacin hemihydrate, fluticasone, and fluconazole are discussed supra. Disclosed herein is a compounded composition comprising a diluent and a dry formulation, wherein the dry formulation comprises a therapeutically effective amount of levofloxacin hemihydrate, a therapeutically effective amount of fluticasone, a therapeutically effective amount of fluconazole, a sufficient amount of an excipient base powder, and a sufficient amount of xylitol. Dry formulations comprising levofloxacin hemihydrate, fluticasone, fluconazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

Disclosed herein is a compounded composition comprising a diluent and a dry formulation, wherein the dry formulation comprises a therapeutically effective amount of fluticasone and a therapeutically effective amount of fluconazole. Dry formulations comprising fluticasone and fluconazole are discussed supra. Disclosed herein is a compounded composition comprising a diluent and a dry formulation, wherein the dry formulation comprises a therapeutically effective amount of fluticasone, a therapeutically effective amount of fluconazole, a sufficient amount of an excipient base powder, and a sufficient amount of xylitol. Dry formulations comprising fluticasone, fluconazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

Disclosed herein is a compounded composition comprising a diluent and a dry formulation, wherein the dry formulation comprises a therapeutically effective amount of vancomycin hydrochloride and a therapeutically effective amount of mupirocin. Dry formulations comprising vancomycin and mupirocin are discussed supra. Disclosed herein is a compounded composition comprising a diluent and a dry formulation, wherein the dry formulation comprises a therapeutically effective amount of vancomycin hydrochloride, a therapeutically effective amount of mupirocin, a sufficient amount of an excipient base powder, and a sufficient amount of xylitol. Dry formulations comprising vancomycin, mupirocin, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

Disclosed herein is a compounded composition comprising a diluent and a dry formulation, wherein the dry formulation comprises a therapeutically effective amount of mupirocin and a therapeutically effective amount of clotrimazole. Dry formulations comprising mupirocin and clotrimazole are discussed supra. Disclosed herein is a compounded composition comprising a diluent and a dry formulation, wherein the dry formulation comprises a therapeutically effective amount of mupirocin, a therapeutically effective amount of clotrimazole, a sufficient amount of an excipient base powder, and a sufficient amount of xylitol. Dry formulations comprising mupirocin, clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

Disclosed herein is a compounded composition comprising a diluent and a dry formulation, wherein the dry formulation comprises a therapeutically effective amount of mupirocin, a therapeutically effective amount of clindamycin, and a therapeutically effective amount of clotrimazole. Dry formulations comprising mupirocin, clindamycin, and clotrimazole are discussed supra. Disclosed herein is a compounded composition comprising a diluent and a dry formulation, wherein the dry formulation comprises a therapeutically effective amount of mupirocin, a therapeutically effective amount of clindamycin, a therapeutically effective amount of clotrimazole, a sufficient amount of an excipient base powder, and a sufficient amount of xylitol. Dry formulations comprising mupirocin, clindamycin, clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

Disclosed herein is a compounded composition comprising a diluent and a dry formulation, wherein the dry formulation comprises a therapeutically effective amount of ceftriaxone. Dry formulations comprising ceftriaxone are discussed supra. Disclosed herein is a compounded composition comprising a diluent and a dry formulation, wherein the dry formulation comprises a therapeutically effective amount of ceftriaxone, a sufficient amount of an excipient base powder, and a sufficient amount of xylitol. Dry formulations comprising ceftriaxone, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

Disclosed herein is a compounded composition comprising a diluent and a dry formulation, wherein the dry formulation comprises a therapeutically effective amount of clotrimazole. Dry formulations comprising clotrimazole are discussed supra. Disclosed herein is a compounded composition comprising a diluent and a dry formulation, wherein the dry formulation comprises a therapeutically effective amount of clotrimazole, a sufficient amount of an excipient base powder, and a sufficient amount of xylitol. Dry formulations comprising clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

Disclosed herein is a compounded composition comprising a diluent and a dry formulation, wherein the dry formulation comprises a therapeutically effective amount of doxycycline hyclate and a therapeutically effective amount of clotrimazole. Dry formulations comprising doxycycline hyclate and clotrimazole are discussed supra. Disclosed herein is a compounded composition comprising a diluent and a dry formulation, wherein the dry formulation comprises a therapeutically effective amount of doxycycline hyclate, a therapeutically effective amount of clotrimazole, a sufficient amount of an excipient base powder, and a sufficient amount of xylitol. Dry formulations comprising doxycycline hyclate, clotrimazole, an excipient base powder, and xylitol are discussed supra. Diluents are known to the art and are discussed supra. In an aspect, the diluent can be a hydrocortisone/acetic acid otic solution. In an aspect, the diluent can be a sodium chloride solution.

E. Capsules

Disclosed herein is a capsule comprising a disclosed dry formulation. Disclosed herein is a capsule comprising a disclosed dry formulation, wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole.

Disclosed herein is a capsule comprising a disclosed dry formulation, wherein the dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline or a pharmaceutically acceptable salt thereof and a therapeutically effective amount of clotrimazole, and (20) a therapeutically effective amount of doxycycline or a pharmaceutically acceptable salt thereof, a therapeutically effective amount of clotrimazole, a sufficient amount of an excipient base powder, and a sufficient amount of xylitol.

In an aspect, a disclosed capsule can comprise about 1 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg, about 100 mg to about 200 mg, or about 200 mg to about 2000 mg of a disclosed dry formulation. In an aspect, a disclosed capsule can comprise about 1 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed dry formulation. In an aspect, a disclosed capsule can comprise about 10 mg of a disclosed dry formulation.

As used herein, the term "capsule" includes a soft or hard shell capsule. A capsule shell can be a unibody delivery vehicle or can be comprised of two capsule shell pieces. In an aspect, the longer capsule shell piece can be called the "body" and the smaller capsule shell piece can be called the "cap". The body and the cap can engage with each other as one shell body. As known to the art, capsule sizes can differ considering various factors that are tailored for any particular application, such as dosage amount or route of administration. Capsules can be manufactured to achieve a variety of capsule shell thicknesses. The release characteristics of a capsule can vary depending on the capsule shell thickness and composition. Standard capsule sizes are known in the art, and include, but are not limited to, the following sizes: Su07 (28 mL), 7 (24 mL), 10 (18 mL), 11 (10 mL), 12e1 (7.5 mL), 12 (5 mL), 13 (3.2 mL), 000 (1.37 mL), 00 (0.95 mL), 0 (0.68 mL), 1 (0.50 mL), 2 (0.37 mL), 3 (0.30 mL), 4 (0.21 mL), and 5 (0.13 mL). Actual volumes in mL are shown in parenthesis. Capsules for oral administration typically range from a size 5 (volume of 0.1 mL) capsule to a size 000 (volume of 1.37 mL) capsule. In an aspect, a disclosed dry formulation can be encapsulated in a capsule or in one or more capsules.

In an aspect, a disclosed capsule comprising a disclosed dry formulation can be broken apart such that its contents can be retrieved. In an aspect, a disclosed capsule can be dissolved in water such that its contents can be contacted with the water.

In an aspect, a disclosed capsule can comprise a therapeutically effective amount of one or more additional active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed capsule can comprise one or more excipients or additives. In an aspect, excipients or additives include, but are not limited to, the following:

solvents, surfactants, humectants, preservatives, flavorings, stabilizers (including antioxidants), binders, and colorants.

Dry formulations and methods of making dry formulations are discussed supra.

F. Containers

Disclosed herein is a container comprising a disclosed dry formulation. Disclosed herein is a container comprising a dry formulation, wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole.

Disclosed herein is a container comprising a dry formulation, wherein the disclosed dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, and a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline and a therapeutically effective amount of clotrimazole, and (20) a therapeutically effective amount of doxycycline, a therapeutically effective amount of clotrimazole, a sufficient amount of an excipient base powder, and a sufficient amount of xylitol.

In an aspect, a disclosed container can be a glass container or a non-glass container and can comprise a stopper or a seal. The stopper can comprise siliconized or non-siliconized rubber. The stopper or seal can comprise metal. The stopper or seal can comprise a Teflon coating or a Teflon treatment. In an aspect, a disclosed container can comprise a syringe. In an aspect, a disclosed container can be a disposable packet. The disposable packet can be moisture free. In an aspect, a disclosed container can be a glass or non-glass vial and can comprise a stopper or a seal. In an aspect, a disclosed container can be a tube and can comprise a removable cap or a removable lid.

In an aspect, a disclosed container can hold or accommodate about 1 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg, about 100 mg to about 200 mg, or about 200 mg to about 2000 mg of a disclosed dry formulation. In an aspect, a disclosed container can comprise about 1 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed dry formulation.

Dry formulations and methods of making dry formulations are discussed infra.

G. Kits

Disclosed herein is a kit comprising a disclosed dry formulation. Disclosed herein is a kit comprising a plurality of containers, each comprising a disclosed dry formulation. Disclosed herein is a kit comprising a plurality of containers, each comprising a disclosed dry formulation, and instructions for using the dry formulation.

Disclosed herein is a kit comprising: a plurality of containers, each container comprising a dry formulation, wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole.

Disclosed herein is a kit comprising: a plurality of containers, each container comprising a dry formulation, wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole, a sufficient amount of an excipient base powder, and a sufficient amount of xylitol, (6) a therapeutically effective amount of clotrimazole, a sufficient amount of an excipient base powder, a sufficient amount of xylitol, and a therapeutically effective amount of ceftriaxone, (7) a therapeutically effective amount of clotrimazole, a therapeutically effective amount of a corticosteroid or a pharmaceutically acceptable salt thereof, a sufficient amount of an excipient base powder, and a sufficient amount of xylitol, (8) a therapeutically effective amount of clotrimazole, a therapeutically effective amount of a betamethasone sodium phosphate, a sufficient amount of an excipient base powder, and a sufficient amount of xylitol, (9) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (10) a therapeutically effective amount of doxycycline hyclate, a therapeutically effective amount of betamethasone sodium phosphate, and a therapeutically effective amount of clotrimazole, and instructions for using the dry formulation, and (11) a therapeutically effective amount of doxycycline hyclate, a therapeutically effective amount of a dexamethasone, and a therapeutically effective amount of clotrimazole; and instructions for using the dry formulation.

Disclosed herein is a kit comprising: a plurality of containers, each container comprising a dry formulation, wherein the dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, and a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline and a therapeutically effective amount of clotrimazole, and (20) a therapeutically effective amount of doxycycline, a therapeutically effective amount of clotrimazole, a sufficient amount of an excipient base powder, and a sufficient amount of xylitol.

Disclosed herein is a kit comprising: a plurality of containers, each container comprising a dry formulation, wherein the dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, and a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline and a therapeutically effective amount of clotrimazole, and (20) a therapeutically effective amount of doxycycline, a therapeutically effective amount of clotrimazole, a sufficient amount of an excipient base powder, and a sufficient amount of xylitol, and instructions for using the dry formulation.

Dry formulation are discussed supra. Methods of making dry formulations are discussed infra.

In an aspect, the plurality of containers can comprise more than 1 container. In an aspect, the plurality can comprise at least 3 containers, at least 7 containers, or at least 10 containers, at least 14 containers, at least 21 containers, at least 30 containers, at least 60 containers, at least 90 containers, at least 120 containers, or at least 150 containers, or more than 150 containers. Containers are known to the art and are discussed supra.

In an aspect, the plurality of containers can comprise a 3 day's supply, or a week's supply, or a 10 day's supply, or a two week's supply, or a month's supply, or a two month's supply, or a three month's supply, or a six month's supply, or more than a six month's supply of a disclosed dry formulation.

In an aspect, the instructions for using the dry formulation can comprise instructions for mixing a dry formulation with a diluent. In an aspect, a disclosed kit can comprise a diluent for a disclosed dry formulation. In an aspect, a diluent can comprise a hydrocortisone/acetic acid otic solution. In an aspect, the hydrocortisone/acetic acid otic solution can be a 1% hydrocortisone/2% acetic acid otic solution. In an aspect, a hydrocortisone/acetic acid otic solution can be commercially available. Diluents are known to the art and are discussed supra.

In an aspect, a disclosed kit can comprise one or more syringes. In an aspect, a syringe can be a disposable syringe or a reusable syringe. In an aspect, a syringe can be a glass syringe or a non-glass syringe. In an aspect, a syringe an comprise a bent configuration. In an aspect, a syringe can comprise a straight configuration.

In an aspect, a disclosed kit can comprise one or more medicine droppers. In an aspect, a medicine dropper can be a device that administers a disclosed compounded composition in a drop wise fashion. In an aspect, a dropper can be a disposable dropper or a reusable dropper. In an aspect, a dropper can comprise a plastic dropper or a glass dropper. In an aspect, a dropper can comprise a bent configuration. In an aspect, a dropper can comprise a straight configuration.

In an aspect, a disclosed kit can comprise a foot bath. Foot baths are known to the art and are discussed supra. In an aspect, a disclosed kit can comprise one or more funnels. In an aspect, a disclosed kit can comprise one or more mixing containers. In an aspect, a disclosed kit can comprise one or more scoops or spoons, such as a 5 cc scoop or spoon or a 1 cc scoop or spoon.

In an aspect, a disclosed kit can comprise one or more bottles of diluent. In an aspect, a disclosed kit can comprise a 3 day's supply, or a week's supply, or a 10 day's supply, or a two week's supply, or a month's supply, or a two month's supply, or a three month's supply, or a six month's supply, or more than a six month's supply of a disclosed diluent. Diluents are known to the art and are discussed supra.

H. Methods of Making a Dry Formulation

Disclosed herein are methods of making a disclosed dry formulation.

1. Mupirocin, an Anti-Bacterial Agent, and an Anti-Fungal Agent

Disclosed herein is a method of making a dry formulation, the method comprising: mixing a therapeutically effective amount of mupirocin, a therapeutically effective amount of an anti-bacterial agent, and a therapeutically effective amount of an anti-fungal agent to make a homogenous dry formulation. Disclosed herein is a method of making a dry formulation, the method comprising: mixing a therapeutically effective amount of mupirocin, a therapeutically effective amount of an anti-bacterial agent, a therapeutically effective amount of an anti-fungal agent, a sufficient amount of an excipient base powder, and a sufficient amount of xylitol to make a homogenous dry formulation.

In an aspect, a disclosed method can comprise obtaining mupirocin, obtaining an anti-bacterial agent, obtaining an anti-fungal agent, obtaining an excipient base powder, obtaining xylitol, or a combination thereof. In an aspect, obtaining can comprise obtaining a bulk source of mupirocin, obtaining a bulk source of an anti-bacterial agent, obtaining a bulk source of an anti-fungal agent, obtaining a bulk source of an excipient base powder, obtaining a bulk source of xylitol, or a combination thereof.

Mupirocin is known to the art and is discussed supra. Anti-bacterial agents are known to the art and are discussed supra. Anti-fungal agents are known to the art and are discussed supra. Excipient base powders, such LoxaSperse™ and XyliFos™, are known to the art and are discussed supra. Xylitol is known to the art and is discussed supra.

In an aspect, the combined ingredients (e.g., the mupirocin, the anti-bacterial agent, the anti-fungal agent, the excipient base powder, and the xylitol, or a combination thereof) can be sifted through a fine mesh strainer and placed in a mixer for a pre-determined amount of time. Methods of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise packaging the dry formulation comprising mupirocin, an anti-bacterial agent, and an anti-fungal agent into a container and sealing the container. In an aspect, a disclosed method can comprise packaging the dry formulation comprising mupirocin, an anti-bacterial agent, an anti-fungal agent, an excipient base powder, and xylitol into a container and sealing the container. In an aspect, a container can be a container disclosed herein, such as, for example, a tube, a vial, a syringe, a dropper, a capsule, etc. In an aspect, a disclosed method can comprise sterilizing the dry formulation comprising mupirocin, an anti-bacterial agent, and an anti-fungal agent. In an aspect, a disclosed method can comprise sterilizing the dry formulation comprising mupirocin, an anti-bacterial agent, an anti-fungal agent, an excipient base powder, and xylitol.

In an aspect, a disclosed method can comprise encapsulating a disclosed composition comprising mupirocin, an anti-bacterial agent, and an anti-fungal agent in a capsule or in one or more capsules. In an aspect, a disclosed method can comprise encapsulating a disclosed composition comprising mupirocin, an anti-bacterial agent, an anti-fungal agent, an excipient base powder, and xylitol in a capsule or in one or more capsules.

2. Mupirocin, Clindamycin Hydrochloride, and Clotrimazole

Disclosed herein is a method of making a dry formulation, the method comprising: mixing a therapeutically effective amount of mupirocin, a therapeutically effective amount of clindamycin hydrochloride, and a therapeutically effective amount of clotrimazole to make a homogenous dry formulation. Disclosed herein is a method of making a dry formulation, the method comprising: mixing a therapeutically effective amount of mupirocin, a therapeutically effective amount of clindamycin hydrochloride, a therapeutically effective amount of clotrimazole, a sufficient amount of an excipient base powder, and a sufficient amount of xylitol to make a homogenous dry formulation.

In an aspect, a disclosed method can comprise obtaining mupirocin, obtaining clindamycin hydrochloride, obtaining clotrimazole, obtaining an excipient base powder, obtaining xylitol, or a combination thereof. In an aspect, obtaining can comprise obtaining a bulk source of mupirocin, obtaining a bulk source of clindamycin hydrochloride, obtaining a bulk source of clotrimazole, obtaining a bulk source of an excipient base powder, obtaining a bulk source of xylitol, or a combination thereof.

Mupirocin is known to the art and is discussed supra. Clindamycin hydrochloride is known to the art and is discussed supra. Clotrimazole is known to the art and is discussed supra. Excipient base powders, such as LoxaSperse™ and XyliFos™, are known to the art and are discussed supra. Xylitol is known to the art and is discussed supra.

In an aspect, the combined ingredients (e.g., the mupirocin, clindamycin hydrochloride, clotrimazole, the excipient base powder, and the xylitol, or a combination thereof) can be sifted through a fine mesh strainer and placed in a mixer for a pre-determined amount of time. Methods of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise packaging the dry formulation comprising mupirocin, clindamycin hydrochloride, and clotrimazole into a disclosed container and sealing the container. In an aspect, a disclosed method can comprise packaging the dry formulation comprising mupirocin, clindamycin hydrochloride, clotrimazole, an excipient base powder, and xylitol into a disclosed container and sealing the container. In an aspect, a container can be a container disclosed herein, such as, for example, a tube, a vial, a syringe, a dropper, a capsule, etc.

In an aspect, a disclosed method can comprise sterilizing the dry formulation comprising mupirocin, clindamycin hydrochloride, and clotrimazole. In an aspect, a disclosed method can comprise sterilizing the dry formulation comprising mupirocin, clindamycin hydrochloride, clotrimazole, an excipient base powder, and xylitol.

In an aspect, a disclosed method can comprise encapsulating a disclosed dry formulation comprising mupirocin, clindamycin hydrochloride, and clotrimazole in a capsule or in one or more capsules. In an aspect, a disclosed method can comprise encapsulating a disclosed dry formulation comprising mupirocin, clindamycin hydrochloride, clotrimazole, an excipient base powder, and xylitol in a capsule or in one or more capsules.

a. Example 1

In an aspect, to make 1 g of the dry formulation, about 0.0256 g mupirocin, about 0.032 g clindamycin hydrochloride, about 0.0038 g clotrimazole, about 0.0918 g an excipient base powder, and about 0.8448 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 1, the term "about" means a value falling within a range that is ±10% of the stated value. In an aspect, the skilled person can combine 0.0256 g±10% mupirocin, 0.032 g±10% clindamycin hydrochloride, 0.0038 g±10% clotrimazole, 0.0918 g±10% excipient base powder, and 0.844 g±10% xylitol and mix together according to a method described above to make about 1.0 g±10% of the dry formulation.

b. Example 2

In an aspect, to make a capsule comprising the dry formulation, about 0.02 g mupirocin, about 0.025 g clindamycin hydrochloride, about 0.003 g clotrimazole, about 0.0716 g an excipient base powder, and about 0.659 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 2, the term "about" means a value falling within a range that is ±10% of the stated value. In an aspect, the skilled person can combine 0.02 g±10% mupirocin, 0.025 g±10% clindamycin hydrochloride, 0.003 g±10% clotrimazole, 0.0716 g±10% excipient base powder, and 0.659 g±10% xylitol and mix together according to a method described above to make 1 capsule comprising the dry formulation.

c. Example 3

In an aspect, to make a capsule comprising the dry formulation, about 2% mupirocin, about 2.5% clindamycin hydrochloride, about 3% clotrimazole, about 7.16% excipient base powder, and about 65.9% xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 3, the term "about" means a value falling within a range that is ±10% of the stated value. In an aspect, the skilled person can combine 2%±10% mupirocin, 2.5%±10% clindamycin hydrochloride, 3%±10% clotrimazole, 7.16%±10% excipient base powder, and 65.9%±10% xylitol and mix together according to a method described above to make 1 capsule comprising the dry formulation.

d. Example 4

In an aspect, to make a capsule comprising the dry formulation, about 2% mupirocin, about 2.5% clindamycin hydrochloride, about 3% clotrimazole, and about 64.7% excipient base powder, can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 4, the term "about" means a value falling within a range that is ±10% of the stated value. In an aspect, the skilled person can combine 2%±10% mupirocin, 2.5%±10% clindamycin hydrochloride, 3%±10% clotrimazole, and 64.7%±10% excipient base powder and mix together according to a method described above to make 1 capsule comprising the dry formulation.

e. Example 5

In an aspect, to make a capsule comprising the dry formulation, about 0.02 g mupirocin, about 0.025 g clindamycin hydrochloride, about 0.003 g clotrimazole, and about 0.647 g excipient base powder can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 5, the term "about" means a value falling within a range that is ±10% of the stated value. In an aspect, the skilled person can combine 0.02 g±10% mupirocin, 0.025 g±10% clindamycin hydrochloride, 0.003 g±10% clotrimazole, and 0.647 g±10% excipient base powder and mix together according to a method described above to make 1 capsule comprising the dry formulation.

f. Example 6

In an aspect, to make 1 g of the dry formulation, about 0.0285 g mupirocin, about 0.0357 g clindamycin hydrochloride, about 0.004 g clotrimazole, and about 0.924 g an excipient base powder can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 6, the term "about" means a value falling within a range that is ±10% of the stated value. In an aspect, the skilled person can combine 0.0285 g±10% mupirocin, 0.0357 g±10% clindamycin hydrochloride, 0.004 g±10% clotrimazole, and 0.924 g±10% excipient base powder and mix together according to a method described above to make about 1.0 g±10% of the dry formulation.

3. Mupirocin, a Corticosteroid or a Salt Thereof, and an Anti-Fungal Agent

Disclosed herein is a method of making a dry formulation, the method comprising: mixing a therapeutically effective amount of mupirocin, a therapeutically effective amount of a corticosteroid or a pharmaceutically acceptable salt thereof, and a therapeutically effective amount of an anti-fungal agent to make a homogenous dry formulation. Disclosed herein is a method of making a dry formulation, the method comprising: mixing a therapeutically effective amount of mupirocin, a therapeutically effective amount of a corticosteroid or a pharmaceutically acceptable salt thereof, and a therapeutically effective amount of an anti-fungal agent, a sufficient amount of an excipient base powder, and a sufficient amount of xylitol to make a homogenous dry formulation.

In an aspect, a disclosed method can comprise obtaining mupirocin, obtaining a corticosteroid or a pharmaceutically acceptable salt thereof, obtaining an anti-fungal agent, obtaining an excipient base powder, obtaining xylitol, or a combination thereof. In an aspect, obtaining can comprise obtaining a bulk source of mupirocin, obtaining a bulk source of a corticosteroid, obtaining a bulk source of an anti-fungal agent, obtaining a bulk source of an excipient base powder, obtaining a bulk source of xylitol, or a combination thereof.

Mupirocin is known to the art and is discussed supra. Corticosteroids as well as their pharmaceutically acceptable salts thereof are known to the art and are discussed supra. Anti-fungal agents are known to the art and are discussed supra. Excipient base powders, such LoxaSperse™ and XyliFos™, are known to the art and are discussed supra. Xylitol is known to the art and is discussed supra.

In an aspect, the combined ingredients (e.g., mupirocin, the corticosteroid or a pharmaceutically acceptable salt thereof, the anti-fungal agent, the excipient base powder, the xylitol, or a combination thereof) can be sifted through a fine mesh strainer and placed in a mixer for a pre-determined amount of time. Methods of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise packaging the dry formulation comprising mupirocin, a corticosteroid or a pharmaceutically acceptable salt thereof, and an antifungal agent into a container and sealing the container. In an aspect, a disclosed method can comprise packaging the dry formulation comprising mupirocin, a corticosteroid or a pharmaceutically acceptable salt thereof, an anti-fungal agent, an excipient base powder, and xylitol into a container and sealing the container. In an aspect, a container can be a container disclosed herein, such as, for example, a tube, a vial, a syringe, a dropper, a capsule, etc.

In an aspect, a disclosed method can comprise sterilizing the dry formulation comprising mupirocin, a corticosteroid or a pharmaceutically acceptable salt thereof, and an anti-fungal agent. In an aspect, a disclosed method can comprise sterilizing the dry formulation comprising mupirocin, a corticosteroid or a pharmaceutically acceptable salt thereof, an anti-fungal agent, an excipient base powder, and xylitol.

In an aspect, a disclosed method can comprise encapsulating a disclosed composition comprising mupirocin, a corticosteroid or a pharmaceutically acceptable salt thereof, and an anti-fungal agent in a capsule or in one or more capsules. In an aspect, a disclosed method can comprise encapsulating a disclosed composition comprising mupirocin, a corticosteroid or a pharmaceutically acceptable salt thereof, an anti-fungal agent, an excipient base powder, and xylitol in a capsule or in one or more capsules.

4. Mupirocin, Betamethasone Sodium Phosphate, and Clotrimazole

Disclosed herein is a method of making a dry formulation, the method comprising: mixing a therapeutically effective amount of mupirocin, a therapeutically effective amount of a betamethasone sodium phosphate, and a therapeutically effective amount of clotrimazole to make a homogenous dry formulation. Disclosed herein is a method of making a dry formulation, the method comprising: mixing a therapeutically effective amount of mupirocin, a therapeutically effective amount of betamethasone sodium phosphate, a therapeutically effective amount of clotrimazole to make a homogenous dry formulation, a sufficient amount of excipient base powder, and a sufficient amount of xylitol.

In an aspect, a disclosed method can comprise obtaining mupirocin, obtaining betamethasone sodium phosphate, obtaining clotrimazole, obtaining an excipient base powder, obtaining xylitol, or a combination thereof. In an aspect, obtaining can comprise obtaining a bulk source of mupirocin, obtaining a bulk source of betamethasone sodium phosphate, obtaining a bulk source of clotrimazole, obtaining a bulk source of excipient base powder, obtaining a bulk source of xylitol, or a combination thereof.

Mupirocin is known to the art and is discussed supra. Betamethasone sodium phosphate is known to the art and is discussed supra. Clotrimazole is known to the art and is discussed supra. Excipient base powders, such LoxaSperse™ and XyliFos™, are known to the art and are discussed supra. Xylitol is known to the art and is discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, the combined ingredients (e.g., mupirocin, betamethasone sodium phosphate, clotrimazole, excipient base powder, and xylitol, or a combination thereof) can be sifted through a fine mesh strainer and placed in a mixer for a pre-determined amount of time. Method of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise packaging the dry formulation comprising mupirocin, betamethasone sodium phosphate, and clotrimazole into a container and sealing the container. In an aspect, a disclosed method can comprise packaging the dry formulation comprising mupirocin, betamethasone sodium phosphate, clotrimazole, an excipient base powder, and xylitol into a container and sealing the container. In an aspect, a container can be a container disclosed herein, such as, for example, a tube, a vial, a syringe, a dropper, a capsule, etc.

In an aspect, a disclosed method can comprise sterilizing the dry formulation comprising mupirocin, betamethasone sodium phosphate, and clotrimazole. In an aspect, a disclosed method can comprise sterilizing the dry formulation comprising mupirocin, betamethasone sodium phosphate, clotrimazole, an excipient base powder, and xylitol.

In an aspect, a disclosed method can comprise encapsulating a disclosed dry formulation comprising mupirocin, betamethasone sodium phosphate, and clotrimazole in a capsule or in one or more capsules. In an aspect, a disclosed method can comprise encapsulating a disclosed dry formulation comprising mupirocin, betamethasone sodium phosphate, clotrimazole, an excipient base powder, and xylitol in a capsule or in one or more capsules.

a. Example 7

In an aspect, to make 1 g of the dry formulation, about 0.0256 g mupirocin, about 0.0012 g betamethasone sodium phosphate, about 0.0038 g clotrimazole, about 0.0918 g an excipient base powder, and about 0.879 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 7, the term "about" means a value falling within a range that is ±10% of the stated value. In an aspect, the skilled person can combine 0.0256 g±10% mupirocin, 0.0012 g±10% betamethasone sodium phosphate, 0.0038 g±10% clotrimazole, 0.0918 g±10% excipient base powder, and 0.879 g±10% xylitol and mix together according to a method described above to make about 1.0 g±10% of the dry formulation.

b. Example 8

In an aspect, to make a capsule comprising the dry formulation, about 0.02 g mupirocin, about 0.001 g betamethasone sodium phosphate, about 0.003 g clotrimazole, about 0.0716 g an excipient base powder, and about 0.686 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 8, the term "about" means a value falling within a range that is ±10% of the stated value. In an aspect, the skilled person can combine 0.02 g±10% mupirocin, 0.001 g±10% betamethasone sodium phosphate, 0.003 g±10% clotrimazole, 0.0716 g±10% excipient base powder, and 0.686 g±10% xylitol and mix together according to a method described above to make 1 capsule comprising the dry formulation.

c. Example 9

In an aspect, to make a capsule comprising the dry formulation, about 2% mupirocin, about 0.1% betamethasone sodium phosphate, about 0.3% clotrimazole, about 7.16% excipient base powder, and about 68.6% xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 9, the term "about" means a value falling within a range that is ±10% of the stated value. In an aspect, the skilled person can combine 2%±10% mupirocin, 0.1%±10% betamethasone sodium phosphate, 0.3%±10% clotrimazole, 7.16%±10% excipient base powder, and 68.6%±10% xylitol and mix together according to a method described above to make 1 capsule comprising the dry formulation.

5. Clotrimazole and an Excipient Base Powder

Disclosed herein is a method of making a dry formulation, the method comprising: mixing a therapeutically effective amount of clotrimazole and a sufficient amount of an excipient base powder make a homogenous dry formulation. Disclosed herein is a method of making a dry formulation, the method comprising: mixing a therapeutically effective amount of clotrimazole, a sufficient amount of an excipient base powder, and a therapeutically effective amount of ceftriaxone to make a homogenous dry formulation.

In an aspect, a disclosed method can comprise obtaining clotrimazole, obtaining an excipient base powder, obtaining ceftriaxone, or a combination thereof. In an aspect, obtaining can comprise obtaining a bulk source of clotrimazole, obtaining a bulk source of an excipient base powder, obtaining a bulk source of ceftriaxone, or a combination thereof.

Clotrimazole is known to the art and is discussed supra. Excipient base powders, such as LoxaSperse™ and XyliFos™, are known to the art and are discussed supra. Ceftriaxone is known to the art and is discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, the combined ingredients (e.g., clotrimazole, excipient base powder, and ceftriaxone, or a combination thereof) can be sifted through a fine mesh strainer and placed in a mixer for a pre-determined amount of time. Method of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise packaging the dry formulation comprising clotrimazole and an excipient base powder into a container and sealing the container. In an aspect, a disclosed method can comprise packaging the dry formulation comprising clotrimazole, an excipient base powder, and ceftriaxone into a container and sealing the container. In an aspect, a container can be a container disclosed herein, such as, for example, a tube, a vial, a syringe, a dropper, a capsule, etc.

In an aspect, a disclosed method can comprise sterilizing the dry formulation comprising clotrimazole and an excipient base powder. In an aspect, a disclosed method can comprise sterilizing the dry formulation comprising clotrimazole, an excipient base powder, and ceftriaxone.

In an aspect, a disclosed method can comprise encapsulating a disclosed composition comprising clotrimazole and an excipient base powder in a capsule or in one or more capsules. In an aspect, a disclosed method can comprise encapsulating a disclosed composition comprising clotrimazole, an excipient base powder, and ceftriaxone in a capsule or in one or more capsules.

a. Example 10

In an aspect, to make 1 g of the dry formulation, about 0.014 g clotrimazole and about 0.992 g an excipient base powder can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation comprising clotrimazole and an excipient base powder can be encapsulated in a capsule. For example, in an aspect, a capsule can be a #00 capsule. Capsules are known to the art and are discussed supra. As used in Example 10, the term "about" means a value falling within a range that is ±10% of the stated value. In an aspect, the skilled person can combine 0.014 g±10% clotrimazole and 0.992 g±10% excipient base powder and mix together according to a method described above to make about 1.0 g±10% of the dry formulation.

b. Example 11

In an aspect, to make a capsule comprising the dry formulation, about 0.01 g clotrimazole and about 0.705 g excipient base powder can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 11, the term "about" means a value falling within a range that is ±10% of the stated value. In an aspect, the skilled person can combine 0.01 g±10% clotrimazole and 0.705 g±10% excipient base powder and mix together according to a method described above to make a capsule comprising the dry formulation.

6. Clotrimazole, an Excipient Base Powder, and Xylitol

Disclosed herein is a method of making a dry formulation, the method comprising: mixing a therapeutically effective amount of clotrimazole, a sufficient amount of an excipient base powder, and a sufficient amount of xylitol to make a homogenous dry formulation. In an aspect, a disclosed method can comprise obtaining clotrimazole, obtaining an excipient base powder, obtaining xylitol, or a combination thereof. In an aspect, obtaining can comprise obtaining a bulk source of clotrimazole, obtaining a bulk source of an excipient base powder, obtaining a bulk source of xylitol, or a combination thereof.

Clotrimazole is known to the art and is discussed supra. Excipient base powders, such as LoxaSperse™ and XyliFos™, are known to the art and are discussed supra. Xylitol is known to the art and is discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, the combined ingredients (e.g., clotrimazole, excipient base powder, and xylitol, or a combination thereof) can be sifted through a fine mesh strainer and placed in a mixer for a pre-determined amount of time. Method of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise packaging the dry formulation comprising clotrimazole, an excipient base powder, and xylitol into a container and sealing the container. In an aspect, a container can be a container disclosed herein, such as, for example, a tube, a vial, a syringe, a dropper, a capsule, etc.

In an aspect, a disclosed method can comprise sterilizing the dry formulation comprising clotrimazole, an excipient base powder, and xylitol.

In an aspect, a disclosed method can comprise encapsulating a disclosed composition comprising clotrimazole, an excipient base powder, and xylitol in a capsule or in one or more capsules.

a. Example 12

In an aspect, to make 1 g of the dry formulation, about 0.01238 g clotrimazole, about 0.08865 g an excipient base powder, and about 0.8989 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 12, the term "about" means a value falling within a range that is ±10% of the stated value. In an aspect, the skilled person can combine 0.01238 g±10% clotrimazole, 0.08865 g±10% excipient base powder, and 0.8989±10% g xylitol and mix together according to a method described above to make about 1.0 g±10% of the dry formulation.

b. Example 13

In an aspect, to make a capsule comprising the dry formulation, about 0.01 g clotrimazole, about 0.0716 g excipient base powder, and about 0.726 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 13, the term "about" means a value falling within a range that is ±10% of the stated value. In an aspect, the skilled person can combine 0.01 g±10% clotrimazole, 0.0716 g±10% excipient base powder, and 0.726±10% g xylitol and mix together according to a method described above to make a capsule comprising the dry formulation.

c. Example 14

In an aspect, to make a capsule comprising the dry formulation, about 1% clotrimazole, about 7.16% excipient base powder, and about 72.6% xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 14, the term "about" means a value falling within a range that is ±10% of the stated value. In an aspect, the skilled person can combine 1%±10% clotrimazole, 7.16% g±10% excipient base powder, and 72.6%±10% g xylitol and mix together according to a method described above to make a capsule comprising the dry formulation.

7. Clotrimazole, a Corticosteroid or a Salt Thereof, an Excipient Base Powder, and Xylitol Disclosed herein is a method of making a dry formulation, the method comprising: mixing a therapeutically effective amount of clotrimazole, a therapeutically effective amount of a corticosteroid or a pharmaceutically acceptable salt thereof, a sufficient amount of an excipient base powder, and a sufficient amount of xylitol to make a homogenous dry formulation.

In an aspect, a disclosed method can comprise obtaining clotrimazole, obtaining a corticosteroid or a pharmaceutically acceptable salt thereof, obtaining an excipient base powder, obtaining xylitol, or a combination thereof. In an aspect, obtaining can comprise obtaining a bulk source of clotrimazole, obtaining a bulk source of a corticosteroid or a pharmaceutically acceptable salt thereof, obtaining a bulk source of an excipient base powder, obtaining a bulk source of xylitol, or a combination thereof.

Clotrimazole is known to the art and is discussed supra. Corticosteroids as well as their pharmaceutically acceptable salts thereof are known to the art and are discussed supra. Excipient base powders, such LoxaSperse™ and XyliFos™, are known to the art and are discussed supra. Xylitol is known to the art and is discussed supra.

In an aspect, the combined ingredients (e.g., clotrimazole, a corticosteroid or a pharmaceutically acceptable salt thereof, excipient base powder, xylitol, or a combination thereof) can be sifted through a fine mesh strainer and placed in a mixer for a pre-determined amount of time. Method of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise packaging the dry formulation comprising clotrimazole, a corticosteroid or a pharmaceutically acceptable salt thereof, an excipient base powder, and xylitol into a container and sealing the container. In an aspect, a container can be a container disclosed herein, such as, for example, a tube, a vial, a syringe, a dropper, a capsule, etc. In an aspect, a disclosed method can comprise sterilizing the dry formulation comprising clotrimazole, a corticosteroid or a pharmaceutically acceptable salt thereof, an excipient base powder, and xylitol.

In an aspect, a disclosed method can comprise encapsulating a disclosed dry formulation comprising clotrimazole, a corticosteroid or a pharmaceutically acceptable salt thereof, an excipient base powder, and xylitol in a capsule or in one or more capsules.

8. Clotrimazole, Betamethasone Sodium Phosphate, an Excipient Base Powder, and Xylitol Disclosed herein is a method of making a dry formulation, the method comprising: mixing a therapeutically effective amount of clotrimazole, a therapeutically effective amount of a betamethasone sodium phosphate, a sufficient amount of an excipient base powder, and a sufficient amount of xylitol to make a homogenous dry formulation.

In an aspect, a disclosed method can comprise obtaining clotrimazole, obtaining betamethasone sodium phosphate, obtaining an excipient base powder, obtaining xylitol, or a combination thereof. In an aspect, obtaining can comprise obtaining a bulk source of clotrimazole, obtaining a bulk source of betamethasone sodium phosphate, obtaining a bulk source of excipient base powder, obtaining a bulk source of xylitol, or a combination thereof.

Clotrimazole is known to the art and is discussed supra. Betamethasone sodium phosphate is known to the art and is discussed supra. Excipient base powders, such LoxaSperse™ and XyliFos™, are known to the art and are discussed supra. Xylitol is known to the art and is discussed supra.

In an aspect, the combined ingredients (e.g., clotrimazole, betamethasone sodium phosphate, the excipient base powder, and the xylitol, or a combination thereof) can be sifted through a fine mesh strainer and placed in a mixer for a pre-determined amount of time. Method of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise packaging the dry formulation comprising clotrimazole, betamethasone sodium phosphate, an excipient base powder, and xylitol into a container and sealing the container. In an aspect, a container can be a container disclosed herein, such as, for example, a tube, a vial, a syringe, a dropper, a capsule, etc. In an aspect, a disclosed method can comprise sterilizing the dry formulation comprising clotrimazole, betamethasone or a salt thereof, an excipient base powder, and xylitol.

In an aspect, a disclosed method can comprise encapsulating a disclosed dry formulation comprising clotrimazole, betamethasone sodium phosphate, an excipient base powder, and xylitol in a capsule or in one or more capsules.

a. Example 15

In an aspect, to make 1 g of the dry formulation, about 0.0037 g clotrimazole, about 0.0012 g betamethasone sodium phosphate, about 0.08839 g an excipient base powder, and about 0.9049 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 15, the term "about" means a value falling within a range that is ±10% of the stated value. In an aspect, the skilled person can combine 0.0037 g±10% of clotrimazole, about 0.0012 g±10% of betamethasone sodium phosphate, 0.08839 g±10% of an excipient base powder, and 0.9049±10% g of xylitol and mix together according to a method described above to make about 1.0 g±10% of the dry formulation.

b. Example 16

In an aspect, to make a capsule comprising the dry formulation, about 0.003 g clotrimazole, about 0.001 g betamethasone sodium phosphate, about 0.0716 g an excipient base powder, and about 0.733 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 16, the term "about" means a value falling within a range that is ±10% of the stated value. In an aspect, the skilled person can combine 0.003 g±10% clotrimazole, about 0.001 g±10% betamethasone sodium phosphate, 0.0716 g±10% excipient base powder, and 0.733±10% g xylitol and mix together according to a method described above to make a capsule comprising the dry formulation.

c. Example 17

In an aspect, to make a capsule comprising the dry formulation, about 0.3% clotrimazole, about 0.1% betamethasone sodium phosphate, about 7.16% excipient base powder, and about 73.3% xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can be encapsulated in a capsule. For example, in an aspect, a capsule can be a #00 capsule. Capsules are known to the art and are discussed supra. As used in Example 17, the term "about" means a value falling within a range that is ±10% of the stated value. In an aspect, the skilled person can combine 0.3%±10% clotrimazole, about 0.1%±10% betamethasone sodium phosphate, 71.6%±10% excipient base powder, and 73.3%±10% g xylitol and mix together according to a method described above to make a capsule comprising the dry formulation.

9. Doxycycline or a Salt Thereof, a Corticosteroid or a Salt Thereof, and Clotrimazole Disclosed herein is a method of making a dry formulation, the method comprising: mixing a therapeutically effective amount of doxycycline or pharmaceutically acceptable salt thereof, a therapeutically effective amount of a corticosteroid or a pharmaceutically acceptable salt thereof, and a therapeutically effective amount of clotrimazole to make a homogenous dry formulation.

Disclosed herein is a method of making a dry formulation, the method comprising: mixing a therapeutically effective amount of doxycycline or pharmaceutically acceptable salt thereof, a therapeutically effective amount of a corticosteroid or a pharmaceutically acceptable salt thereof, a therapeutically effective amount of an clotrimazole, a sufficient amount of an excipient base powder, and a sufficient amount of xylitol to make a homogenous dry formulation.

In an aspect, a disclosed method can comprise obtaining doxycycline or a pharmaceutically acceptable salt thereof, obtaining a corticosteroid or a pharmaceutically acceptable salt thereof, obtaining clotrimazole, obtaining an excipient base powder, obtaining xylitol, or a combination thereof. In an aspect, obtaining can comprise obtaining a bulk source of doxycycline or pharmaceutically acceptable salt thereof, obtaining a bulk source of corticosteroid or a pharmaceutically acceptable salt thereof, obtaining a bulk source of clotrimazole, obtaining a bulk source of an excipient base powder, obtaining a bulk source of xylitol, or a combination thereof.

Doxycycline as well as pharmaceutically acceptable salts thereof are known to the art and are discussed supra.

Corticosteroids as well as pharmaceutically acceptable salts thereof are known to the art and are discussed supra. Clotrimazole is known to the art and is discussed supra. Excipient base powders, such LoxaSperse™ and XyliFos™, are known to the art and are discussed supra. Xylitol is known to the art and is discussed supra.

In an aspect, the combined ingredients (e.g., doxycycline or a pharmaceutically acceptable salt thereof, a corticosteroid or a pharmaceutically acceptable salt thereof, clotrimazole, the excipient base powder, and the xylitol, or a combination thereof) can be sifted through a fine mesh strainer and placed in a mixer for a pre-determined amount of time. Method of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise packaging the dry formulation comprising doxycycline or pharmaceutically acceptable salt thereof, a corticosteroid or a pharmaceutically acceptable salt thereof, and clotrimazole into a container and sealing the container. In an aspect, a disclosed method can comprise packaging the dry formulation comprising doxycycline or pharmaceutically acceptable salt thereof, a corticosteroid or a pharmaceutically acceptable salt thereof, clotrimazole, an excipient base powder, and xylitol into a container and sealing the container. In an aspect, a container can be a container disclosed herein, such as, for example, a tube, a vial, a syringe, a dropper, a capsule, etc.

In an aspect, a disclosed method can comprise sterilizing the dry formulation comprising doxycycline or pharmaceutically acceptable salt thereof, a corticosteroid or a pharmaceutically acceptable salt thereof, and clotrimazole. In an aspect, a disclosed method can comprise sterilizing the dry formulation comprising doxycycline or pharmaceutically acceptable salt thereof, a corticosteroid or a pharmaceutically acceptable salt thereof, clotrimazole, an excipient base powder, and xylitol.

In an aspect, a disclosed method can comprise encapsulating a disclosed dry formulation comprising doxycycline or pharmaceutically acceptable salt thereof, a corticosteroid or a pharmaceutically acceptable salt thereof, and clotrimazole in a capsule or in one or more capsules. In an aspect, a disclosed method can comprise encapsulating a disclosed dry formulation comprising doxycycline or pharmaceutically acceptable salt thereof, a corticosteroid or a pharmaceutically acceptable salt thereof, clotrimazole, an excipient base powder, and xylitol in a capsule or in one or more capsules.

10. Doxycycline Hyclate, Betamethasone Sodium Phosphate, and Clotrimazole

Disclosed herein is a method of making a dry formulation, the method comprising: mixing a therapeutically effective amount of doxycycline hyclate, a therapeutically effective amount of a betamethasone sodium phosphate, and a therapeutically effective amount of clotrimazole to make a homogenous dry formulation.

Disclosed herein is a method of making a dry formulation, the method comprising: mixing a therapeutically effective amount of doxycycline hyclate, a therapeutically effective amount of betamethasone sodium phosphate, a therapeutically effective amount of an clotrimazole, a sufficient amount of an excipient base powder, and a sufficient amount of xylitol to make a homogenous dry formulation.

In an aspect, a disclosed method can comprise obtaining doxycycline hyclate, obtaining betamethasone sodium phosphate, obtaining clotrimazole, obtaining an excipient base powder, obtaining xylitol, or a combination thereof. In an aspect, obtaining can comprise obtaining a bulk source of doxycycline hyclate, obtaining a bulk source of betamethasone sodium phosphate, obtaining a bulk source of clotrimazole, obtaining a bulk source of an excipient base powder, obtaining a bulk source of xylitol, or a combination thereof.

Doxycycline hyclate is known to the art and is discussed supra. Betamethasone sodium phosphate is known to the art and is discussed supra. Clotrimazole is known to the art and is discussed supra. Excipient base powders, such LoxaSperse™ and XyliFos™, are known to the art and are discussed supra. Xylitol is known to the art and is discussed supra.

In an aspect, the combined ingredients (e.g., doxycycline hyclate, betamethasone sodium phosphate, clotrimazole, excipient base powder, xylitol, or a combination thereof) can be sifted through a fine mesh strainer and placed in a mixer for a pre-determined amount of time. Method of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise packaging the dry formulation comprising doxycycline hyclate, betamethasone sodium phosphate, and clotrimazole into a container and sealing the container. In an aspect, a disclosed method can comprise packaging the dry formulation comprising doxycycline hyclate, betamethasone sodium phosphate, clotrimazole, an excipient base powder, and xylitol into a container and sealing the container. In an aspect, a container can be a container disclosed herein, such as, for example, a tube, a vial, a syringe, a dropper, a capsule, etc.

In an aspect, a disclosed method can comprise sterilizing the dry formulation comprising doxycycline hyclate, betamethasone sodium phosphate, and clotrimazole. In an aspect, a disclosed method can comprise sterilizing the dry formulation comprising doxycycline hyclate, betamethasone sodium phosphate, clotrimazole, an excipient base powder, and xylitol.

In an aspect, a disclosed method can comprise encapsulating a disclosed dry formulation comprising doxycycline hyclate, betamethasone sodium phosphate, and clotrimazole in a capsule or in one or more capsules. In an aspect, a disclosed method can comprise encapsulating a disclosed dry formulation comprising doxycycline hyclate, betamethasone sodium phosphate, clotrimazole, an excipient base powder, and xylitol in a capsule or in one or more capsules.

a. Example 18

In an aspect, to make about 1.0 g of the dry formulation, about 0.0394 g doxycycline hyclate, about 0.0013 g betamethasone sodium phosphate, about 0.0039 g clotrimazole, about 0.4605 g excipient base powder, and about 0.4986 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can then be encapsulated in a capsule. For example, in an aspect, a capsule can be a #00 capsule. Capsules are known to the art and are discussed supra. As used in Example 18, the term "about" means a value falling within a range that is ±10% of the stated value. In an aspect, the skilled person can combine 0.0394 g±10% doxycycline hyclate, about 0.0013 g±10% betamethasone sodium phosphate, about 0.0039 g±10% clotrimazole, about 0.4605 g±10% excipient base powder, and about 0.4986 g±10% xylitol and mix together according to a method described above to make the dry formulation.

b. Example 19

In an aspect, to make a capsule comprising the dry formulation, about 0.03 g doxycycline hyclate, about 0.001 g betamethasone sodium phosphate, about 0.003 g clotrimazole, about 0.35 g excipient base powder, and about 0.379 g xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can then be encapsulated in a capsule. For example, in an aspect, a capsule can be a #00 capsule. Capsules are known to the art and are discussed supra. As used in Example 19, the term "about" means a value falling within a range that is ±10% of the stated value. In an aspect, the skilled person can combine about 0.03 g±10% doxycycline hyclate, about 0.001 g±10% betamethasone sodium phosphate, about 0.003 g±10% clotrimazole, about 0.35 g±10% excipient base powder, and about 0.379 g±10% xylitol and mix together according to a method described above to make the dry formulation.

c. Example 20

In an aspect, to make a capsule comprising the dry formulation, about 3% doxycycline hyclate, about 0.1% g betamethasone sodium phosphate, about 0.3% clotrimazole, about 35% excipient base powder, and about 37.9% xylitol can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can then be encapsulated in a capsule. For example, in an aspect, a capsule can be a #00 capsule. Capsules are known to the art and are discussed supra. As used in Example 20, the term "about" means a value falling within a range that is ±10% of the stated value. In an aspect, the skilled person can combine about 3%±10% doxycycline hyclate, about 0.1%±10% betamethasone sodium phosphate, about 0.3%±10% clotrimazole, about 35%±10% excipient base powder, and about 37.9%±10% xylitol and mix together according to a method described above to make the dry formulation.

11. Doxycycline Hyclate, Dexamethasone, and Clotrimazole

Disclosed herein is a method of making a dry formulation, the method comprising: mixing a therapeutically effective amount of doxycycline hyclate, a therapeutically effective amount of a dexamethasone, and a therapeutically effective amount of clotrimazole to make a homogenous dry formulation. Disclosed herein is a method of making a dry formulation, the method comprising: mixing a therapeutically effective amount of doxycycline hyclate, a therapeutically effective amount of dexamethasone, a therapeutically effective amount of an clotrimazole, a sufficient amount of an excipient base powder, and a sufficient amount of xylitol to make a homogenous dry formulation.

In an aspect, a disclosed method can comprise obtaining doxycycline hyclate, obtaining dexamethasone, obtaining clotrimazole, obtaining an excipient base powder, obtaining xylitol, or a combination thereof. In an aspect, obtaining can comprise obtaining a bulk source of doxycycline hyclate, obtaining a bulk source of dexamethasone, obtaining a bulk source of clotrimazole, obtaining a bulk source of an excipient base powder, obtaining a bulk source of xylitol, or a combination thereof.

Doxycycline hyclate is known to the art and is discussed supra. Dexamethasone is known to the art and is discussed supra. Clotrimazole is known to the art and is discussed supra. Excipient base powders, such LoxaSperse™ and XyliFos™, are known to the art and are discussed supra. Xylitol is known to the art and is discussed supra.

In an aspect, the formula presented below can be used to identify the approximate amount of powder from crushed doxycycline hyclate tablets needed for 1 g of the compounded composition:

avg. tablet weight (g)×% of a tablet needed=amt. of powder from crushed tablets needed (g)

For example, in an aspect, the average weight of a 100 mg doxycycline hyclate tablet is about 243.5 mg, the average weight of a 6 mg dexamethasone tablet is about 99 mg, and the average weight of a 10 mg clotrimazole troche is about 1000 mg.

In an aspect, a disclosed capsule can comprise about 117.5 mg doxycycline hyclate, which is equivalent to about 1.175 doxycycline hyclate 100 mg tablets, which is equivalent to about 286 mg of powder from a crushed 100 mg doxycycline hyclate tablet. In an aspect, a disclosed capsule can comprise about 2 mg dexamethasone, which is equivalent to about 0.333 dexamethasone 6 mg tablet, which is equivalent to about 33 mg of powder from a crushed 6 mg dexamethasone tablet. In an aspect, a disclosed capsule can comprise about 2.46 mg clotrimazole, which is equivalent to about 0.246 clotrimazole 10 mg troche, which is equivalent to about 246 mg of powder from a crushed 10 mg clotrimazole troche.

In an aspect, the combined ingredients (e.g., doxycycline hyclate, dexamethasone, and clotrimazole) can be sifted through a fine mesh strainer and placed in a mixer for a pre-determined amount of time. Method of mixing and mixing devices are known to the art. In an aspect, the mixing can comprise using an electronic mortar and pestle (EMP). In an aspect, the mixing can comprise using an electronic mixer-shaker, such as, for example, a TURBULA. In an aspect, the pre-determined amount of time can be about 1 hour. In an aspect, the pre-determined amount of time can be about 15 minutes to about 30 minutes, about 30 minutes to about 1 hour, about 1 hour to about 2 hours, about 2 hours to about 3 hours, or about 3 or more hours. In an aspect, the dry formulation can then be distributed into one or more disclosed containers (i.e., tube, a vial, a syringe, a dropper, a capsule, etc.). For example, the dry formulation can be encapsulated in one or more capsules, such as, a #00 capsule. Capsules are known to the art and are discussed supra.

In an aspect, a disclosed method can comprise mixing one or more excipients or additives with the dry formulation. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional active agents with the dry formulation. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise packaging the dry formulation comprising doxycycline hyclate, dexamethasone, and clotrimazole into a container and sealing the container. In an aspect, a disclosed method can comprise packaging the dry formulation comprising doxycycline hyclate, dexamethasone, clotrimazole, an excipient base powder, and xylitol into a container and sealing the container. In an aspect, a container can be a container disclosed herein, such as, for example, a tube, a vial, a syringe, a dropper, a capsule, etc.

In an aspect, a disclosed method can comprise sterilizing the dry formulation comprising doxycycline hyclate, dexamethasone, and clotrimazole. In an aspect, a disclosed method can comprise sterilizing the dry formulation comprising doxycycline hyclate, dexamethasone, clotrimazole, an excipient base powder, and xylitol.

In an aspect, a disclosed method can comprise encapsulating a disclosed dry formulation comprising doxycycline hyclate, dexamethasone, and clotrimazole in a capsule or in one or more capsules. In an aspect, a disclosed method can comprise encapsulating a disclosed dry formulation comprising doxycycline hyclate, dexamethasone, clotrimazole, an excipient base powder, and xylitol in a capsule or in one or more capsules.

a. Example 21

In an aspect, to make a capsule comprising the dry formulation, crushed powder from about 1.175 tablets of doxycycline hyclate (i.e., a 100 mg doxycycline hyclate tablet having an average weight of about 243.5 g), crushed powder from about 0.3333 tablets of dexamethasone (i.e., a 6 mg dexamethasone tablet having an average weight of about 99 mg), and crushed powder from about 0.246 troches of clotrimazole (i.e., a 10 mg clotrimazole troche having an average weight of about 1000 mg) can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can then be encapsulated in a capsule. For example, in an aspect, a capsule can be a #00 capsule. Capsules are known to the art and are discussed supra. As used in Example 21, the term "about" means a value falling within a range that is ±10% of the stated value. In an aspect, to make a capsule, the skilled person can combine crushed powder from about 1.175 tablets ±10% of doxycycline hyclate (i.e., a 100 mg doxycycline hyclate tablet having an average weight of about 243.5 g), crushed powder from about 0.3333 tablets ±10% of dexamethasone (i.e., a 6 mg dexamethasone tablet having an average weight of about 99 mg), and crushed powder from about 0.246 troches ±10% of clotrimazole (i.e., a 10 mg clotrimazole troche having an average weight of about 1000 mg) and mix together according to a disclosed method.

b. Example 22

In an aspect, to make a capsule comprising the dry formulation, about 286 mg of crushed powder from doxycycline hyclate tablets (i.e., a 100 mg doxycycline hyclate tablet having an average tablet weight of about 243.5 g), about 33 mg of crushed powder from dexamethasone tablet (i.e., a 6 mg dexamethasone tablet having an average tablet weight of about 99 mg), and about 246 mg of powder from crushed clotrimazole troches (i.e., a 10 mg clotrimazole troche having an average tablet weight of about 1000 mg) can be combined and mixed together according to a method described above. In an aspect, the combined ingredients can be sifted through a fine mesh strainer and placed in a TURBULA for a pre-determined amount of time. In an aspect, the pre-determined amount of time can be about 1 hr. In an aspect, the dry formulation can then be encapsulated in a capsule. For example, in an aspect, a capsule can be a #00 capsule. Capsules are known to the art and are discussed supra. As used in Example 22, the term "about" means a value falling within a range that is ±10% of the stated value. In an aspect, the skilled person can combine 286 mg±10% of crushed powder from doxycycline hyclate tablets (i.e., a 100 mg doxycycline hyclate tablet), 33 mg±10% of crushed powder from dexamethasone tablet (i.e., a 6 mg dexamethasone tablet), and 246 mg±10% of crushed powder from clotrimazole troches (i.e., a 10 mg clotrimazole troche) and mix together according to a disclosed method.

12. Miscellaneous

Disclosed herein is a method of making a dry formulation, the method comprising: mixing a therapeutically effective amount of azithromycin, a therapeutically effective amount of fluticasone, and a therapeutically effective amount of fluconazole to make a homogenous dry formulation. Disclosed herein is a method of making a dry formulation, the method comprising: mixing a therapeutically effective amount of azithromycin, a therapeutically effective amount of fluticasone, a therapeutically effective amount of fluconazole, a sufficient amount of an excipient base powder, and a sufficient amount of xylitol to make a homogenous dry formulation. In an aspect, a disclosed method can comprise obtaining azithromycin, obtaining fluticasone, obtaining fluconazole, obtaining an excipient base powder, obtaining xylitol, or a combination thereof. In an aspect, obtaining can comprise obtaining a bulk source of azithromycin, obtaining a bulk source of fluticasone, obtaining a bulk source of fluconazole, obtaining a bulk source of an excipient base powder, obtaining a bulk source of xylitol, or a combination thereof.

Disclosed herein is a method of making a dry formulation, the method comprising: mixing a therapeutically effective amount of sulfamethoxazole, a therapeutically effective amount of trimethoprim, a therapeutically effective amount of fluticasone, and a therapeutically effective amount of fluconazole to make a homogenous dry formulation. Disclosed herein is a method of making a dry formulation, the method comprising: mixing a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol to make a homogenous dry formulation. In an aspect, a disclosed method can comprise obtaining sulfamethoxazole, obtaining trimethoprim, obtaining fluticasone, obtaining fluconazole, obtaining an excipient base powder, obtaining xylitol, or a combination thereof. In an aspect, obtaining can comprise obtaining a bulk source of sulfamethoxazole, obtaining a bulk source of trimethoprim, obtaining a bulk source of fluticasone, obtaining a bulk source of fluconazole, obtaining a bulk source of an excipient base powder, obtaining a bulk source of xylitol, or a combination thereof.

Disclosed herein is a method of making a dry formulation, the method comprising: mixing a therapeutically effective amount of levofloxacin hemihydrate, a therapeutically effective amount of fluticasone, and a therapeutically effective amount of fluconazole to make a homogenous dry formulation. Disclosed herein is a method of making a dry formulation, the method comprising: mixing a therapeutically effective amount of levofloxacin hemihydrate, a therapeutically effective amount of fluticasone, a therapeutically effective amount of fluconazole, a sufficient amount of an excipient base powder, and a sufficient amount of xylitol to make a homogenous dry formulation. In an aspect, a disclosed method can comprise obtaining levofloxacin hemihydrate, obtaining fluticasone, obtaining fluticasone, obtaining fluconazole, obtaining an excipient base powder, obtaining xylitol, or a combination thereof. In an aspect, obtaining can comprise obtaining a bulk source of sulfamethoxazole, obtaining a bulk source of trimethoprim, obtaining a bulk source of fluticasone, obtaining a bulk source of fluconazole, obtaining a bulk source of an excipient base powder, obtaining a bulk source of xylitol, or a combination thereof.

Disclosed herein is a method of making a dry formulation, the method comprising: mixing a therapeutically effective amount of fluticasone and a therapeutically effective amount of fluconazole to make a homogenous dry formulation. Disclosed herein is a method of making a dry formulation, the method comprising: mixing a therapeutically effective amount of fluticasone, a therapeutically effective amount of fluconazole, a sufficient amount of an excipient base powder, and a sufficient amount of xylitol to make a homogenous dry formulation. In an aspect, a disclosed method can comprise obtaining fluticasone, obtaining fluconazole, obtaining an excipient base powder, obtaining xylitol, or a combination thereof. In an aspect, obtaining can comprise obtaining a bulk source of fluticasone, obtaining a bulk source of fluconazole, obtaining a bulk source of an excipient base powder, obtaining a bulk source of xylitol, or a combination thereof.

Disclosed herein is a method of making a dry formulation, the method comprising: mixing a therapeutically effective amount of vancomycin hydrochloride and a therapeutically effective amount of mupirocin to make a homogenous dry formulation. Disclosed herein is a method of making a dry formulation, the method comprising: mixing a therapeutically effective amount of vancomycin hydrochloride, a therapeutically effective amount of mupirocin, a sufficient amount of an excipient base powder, and a sufficient amount of xylitol to make a homogenous dry formulation. In an aspect, a disclosed method can comprise obtaining vancomycin hydrochloride, obtaining mupirocin, obtaining an excipient base powder, obtaining xylitol, or a combination thereof. In an aspect, obtaining can comprise obtaining a bulk source of vancomycin hydrochloride, obtaining a bulk source of mupirocin, obtaining a bulk source of an excipient base powder, obtaining a bulk source of xylitol, or a combination thereof.

Disclosed herein is a method of making a dry formulation, the method comprising: mixing a therapeutically effective amount of mupirocin and a therapeutically effective amount of clotrimazole to make a homogenous dry formulation. Disclosed herein is a method of making a dry formulation, the method comprising: mixing a therapeutically effective amount of mupirocin and a therapeutically effective amount of clotrimazole, a sufficient amount of an excipient base powder, and a sufficient amount of xylitol to make a homogenous dry formulation. In an aspect, a disclosed method can comprise obtaining mupirocin, obtaining clotrimazole, obtaining an excipient base powder, obtaining xylitol, or a combination thereof. In an aspect, obtaining can comprise obtaining a bulk source of mupirocin, obtaining a bulk source of clotrimazole, obtaining a bulk source of an excipient base powder, obtaining a bulk source of xylitol, or a combination thereof.

Disclosed herein is a method of making a dry formulation, the method comprising: mixing a therapeutically effective amount of mupirocin, a therapeutically effective amount of clindamycin, and a therapeutically effective amount of clotrimazole to make a homogenous dry formulation. Disclosed herein is a method of making a dry formulation, the method comprising: mixing a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol to make a homogenous dry formulation. In an aspect, a disclosed method can comprise obtaining mupirocin, obtaining clindamycin or a pharmaceutically acceptable salt thereof, obtaining clotrimazole, obtaining an excipient base powder, obtaining xylitol, or a combination thereof. In an aspect, obtaining can comprise obtaining a bulk source of mupirocin, obtaining a bulk source of clindamycin or a pharmaceutically acceptable salt thereof, obtaining a bulk source of clotrimazole, obtaining a bulk source of an excipient base powder, obtaining a bulk source of xylitol, or a combination thereof.

Disclosed herein is a method of making a dry formulation, the method comprising: mixing a therapeutically effective amount of ceftriaxone. Disclosed herein is a method of making a dry formulation, the method comprising: mixing a therapeutically effective amount of ceftriaxone, a sufficient amount of an excipient base powder, and a sufficient amount of xylitol to make a homogenous dry formulation. In an aspect, a disclosed method can comprise obtaining ceftriaxone, obtaining an excipient base powder, obtaining xylitol, or a combination thereof. In an aspect, obtaining can comprise obtaining a bulk source of ceftriaxone, obtaining a bulk source of an excipient base powder, obtaining a bulk source of xylitol, or a combination thereof.

Disclosed herein is a method of making a dry formulation, the method comprising: mixing a therapeutically effective amount of clotrimazole to make a homogenous dry formulation. Disclosed herein is a method of making a dry formulation, the method comprising: mixing a therapeutically effective amount of clotrimazole, a sufficient amount of an excipient base powder, and a sufficient amount of xylitol to make a homogenous dry formulation. In an aspect, a disclosed method can comprise obtaining clotrimazole, obtaining an excipient base powder, obtaining xylitol, or a combination thereof. In an aspect, obtaining can comprise obtaining a bulk source of clotrimazole, obtaining a bulk source of an excipient base powder, obtaining a bulk source of xylitol, or a combination thereof.

Disclosed herein is a method of making a dry formulation, the method comprising: mixing a therapeutically effective amount of doxycycline or a pharmaceutically acceptable salt thereof and a therapeutically effective amount of clotrimazole to make a homogenous dry formulation. Disclosed herein is a method of making a dry formulation, the method comprising: mixing a therapeutically effective amount of doxycycline or a pharmaceutically acceptable salt thereof, a therapeutically effective amount of clotrimazole, a sufficient amount of an excipient base powder, and a sufficient amount of xylitol to make a homogenous dry formulation. In an aspect, a disclosed method can comprise obtaining doxycycline or a pharmaceutically acceptable salt thereof, obtaining clotrimazole, obtaining an excipient base powder, obtaining xylitol, or a combination thereof. In an aspect, obtaining can comprise obtaining a bulk source of doxycycline or a pharmaceutically acceptable salt thereof, obtaining a bulk source of clotrimazole, obtaining a bulk source of an excipient base powder, obtaining a bulk source of xylitol, or a combination thereof.

I. Methods of Making a Compounded Composition

Disclosed herein is a method of making a compounded composition comprising: mixing a dry formulation with a diluent to generate a homogenous compounded composition (i.e., a compounded solution or suspension), wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole.

Disclosed herein is a method of making a compounded composition comprising: mixing a dry formulation with a diluent to generate a homogenous compounded composition (i.e., a compounded solution or suspension), wherein the dry formulation comprises wherein the dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline or a pharmaceutically acceptable salt thereof and a therapeutically effective amount of clotrimazole, and (20) a therapeutically effective amount of doxycycline or a pharmaceutically acceptable salt thereof, a therapeutically effective amount of clotrimazole, a sufficient amount of an excipient base powder, and a sufficient amount of xylitol.

Diluents are known to the art. In an aspect, a diluent can be a hydrocortisone/acetic acid otic solution. In an aspect, a hydrocortisone/acetic acid solution can be a commercially available hydrocortisone/acetic acid otic solution, for example, a hydrocortisone 1%/acetic acid 2% otic solution. In an aspect, a diluent can be a sodium chloride solution.

In an aspect, mixing a dry formulation with a diluent can comprise adding to a mixing container a diluent and the contents of one capsule comprising a dry formulation and agitating the contents of the mixing container. In an aspect, mixing a dry formulation with a diluent can comprise adding to a mixing container a dry formulation and agitating the contents of the mixing container. In an aspect, agitation can ensure dissolution of the disclosed dry formulation into a disclosed diluent. Mixing containers are known to the art and are discussed supra.

In an aspect, a disclosed method can comprise packaging the compounded composition into a disclosed container and sealing the container. In an aspect, a container can be a container disclosed herein, such as, for example, a tube, a vial, a syringe, a dropper, a capsule, etc. In an aspect, a disclosed method can comprise sterilizing the compounded composition.

Dry formulations are discussed supra. Methods of making a disclosed dry formulation are discussed supra. Containers are known to the art and are discussed supra.

J. Methods of Treating or Preventing an Ear Infection

Disclosed herein is a method of treating or preventing an ear infection, the method comprising: (i) administering to an affected ear of a subject a compounded composition, wherein the compounded composition comprises a dry formulation mixed with a diluent, wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole.

Disclosed herein is a method of treating or preventing an ear infection, the method comprising: (i) administering to an affected ear of a subject a compounded composition, wherein the compounded composition comprises a dry formulation mixed with a diluent, wherein the dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline or a pharmaceutically acceptable salt thereof and a therapeutically effective amount of clotrimazole, and (20) a therapeutically effective amount of doxycycline or a pharmaceutically acceptable salt thereof, a therapeutically effective amount of clotrimazole, a sufficient amount of an excipient base powder, and a sufficient amount of xylitol.

Disclosed herein is a method of treating or preventing an ear infection, the method comprising: (i) preparing a homogenous compounded composition, wherein the compounded composition comprises a dry formulation mixed with a diluent, wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole; and (ii) administering to an affected ear of a subject the compounded composition.

Disclosed herein is a method of treating or preventing an ear infection, the method comprising: (i) preparing a homogenous compounded composition, wherein the compounded composition comprises a dry formulation mixed with a diluent, wherein the dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline or a pharmaceutically acceptable salt thereof and a therapeutically effective amount of clotrimazole, and (20) a therapeutically effective amount of doxycycline or a pharmaceutically acceptable salt thereof, a therapeutically effective amount of clotrimazole, a sufficient amount of an excipient base powder, and a sufficient amount of xylitol; and (ii) administering to an affected ear of a subject the compounded composition.

In an aspect, a subject can be diagnosed with or can be suspected of having a bacterial infection or a fungal infection or both that affects one or both of the subject's ears.

In an aspect, preparing a compounded composition can comprise mixing a disclosed dry formulation with a diluent to generate a homogenous compounded composition (i.e., a compounded solution or suspension). Methods of preparing a disclosed compounded composition are discussed supra. Diluents are known to the art. In an aspect, a diluent can be a hydrocortisone/acetic acid otic solution. In an aspect, a diluent can be a sodium chloride solution.

Mixing containers are known to the art and are discussed supra. In an aspect, a disclosed method can comprise cleaning and drying a mixing container.

In an aspect, a disclosed method can comprise orally administering to the subject a pharmaceutical composition comprising one or more active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise repeating the administering to the affected ear step until the bacterial infection, suspected bacterial infection, the fungal infection, or the suspected fungal infection is eradicated or appears to be eradicated. In an aspect, a disclosed method can comprise repeating the administering step twice daily until the bacterial infection, suspected bacterial infection, the fungal infection, or the suspected fungal infection is eradicated or appears to be eradicated. In an aspect, a disclosed method can comprise administering step twice daily for a pre-determined amount of time. In an aspect, the pre-determined amount of time can comprise at least 5 days, at least 7 days, at least 10 days, at least 14 days, at least 15 days, at least 21 days, at least 30 days, or more than 30 days. In an aspect, the pre-determined amount can comprise an amount of time lasting at least 5-7 days, at least 7-10 days, at least 10-14 days, at least 14-21 days, at least 21-30 days, such as 15 days, at least 30 days, such as 30 days, or more than 30 days.

In an aspect, administering a compounded composition to the affected ear can comprise contacting a disclosed compounded composition with the subject's affected ear. For example, in an aspect, a disclosed compounded composition can be administered to the subject's affected ear in a drop-wise fashion. In an aspect, the tragus can be pumped several times by pushing inward to facilitate penetration of the drops into the middle ear. In an aspect, the subject can lie with the affected ear upward, and then the compounded composition can be administered drop wise into the subject's affected ear. In an aspect, after the administration of the compounded composition to the subject's affected ear, the subject can maintain this position for about 30 to 90 seconds. In an aspect, the subject can maintain this position for about 45 seconds, about 60 seconds, or about 75 seconds. In an aspect, the subject can maintain this position for about 60 second.

In an aspect, after administering a disclosed compounded composition to the affected ear of a subject, the subject can administer a disclosed compounded composition the other ear.

In an aspect, a disclosed compounded composition can be warmed by holding the container in one's hand for one or two minutes (as the administration of a cold composition into a subject's ear may elicit dizziness).

In one embodiment, the method includes utilization of isopropyl alcohol. For example, isopropyl alcohol may be utilized in the treatment of a patient having an ear infection or an ear infection and a perforated tympanic membrane. In one embodiment, isopropyl alcohol may be used in combination with topical antibiotics or antiseptics into the ear. In a further embodiment, isopropyl alcohol may be included in the compounded composition. For example, isopropyl alcohol may be embedded in an aqueous solution carrier including the compounded composition.

In an aspect, a disclosed method of treating or preventing an infection can comprise modifying one or more aspects of the disclosed method. For example, in an aspect, a disclosed method can comprise changing or altering the amount of the disclosed compounded composition applied to one or both of the subject's ears, or by changing the frequency of the subject's use of the compounded composition, or by changing the duration of time that the subject uses the compounded composition, or by substituting one compounded composition for another compounded composition, or a combination thereof.

K. Methods of Treating or Preventing a Skin Infection

Disclosed herein is a method of treating or preventing a skin infection, the method comprising: (i) applying to the skin of a subject a compounded composition, wherein the compounded composition comprises a dry formulation mixed with a diluent, wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole.

Disclosed herein is a method of treating or preventing a skin infection, the method comprising: (i) applying to the skin of a subject a compounded composition, wherein the compounded composition comprises a dry formulation mixed with a diluent, wherein the dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline or a pharmaceutically acceptable salt thereof and a therapeutically effective amount of clotrimazole, and (20) a therapeutically effective amount of doxycycline or a pharmaceutically acceptable salt thereof, a therapeutically effective amount of clotrimazole, a sufficient amount of an excipient base powder, and a sufficient amount of xylitol.

Disclosed herein is a method of treating or preventing a skin infection, the method comprising: (i) preparing a homogenous compounded composition, wherein the compounded composition comprises a dry formulation mixed with a diluent, wherein the dry formulation comprises (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole; and (ii) applying the compounded composition to the skin of the subject.

Disclosed herein is a method of treating or preventing a skin infection, the method comprising: (i) preparing a homogenous compounded composition, wherein the compounded composition comprises a dry formulation mixed with a diluent, wherein the dry formulation comprises (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline or a pharmaceutically acceptable salt thereof and a therapeutically effective amount of clotrimazole, and (20) a therapeutically effective amount of doxycycline or a pharmaceutically acceptable salt thereof, a therapeutically effective amount of clotrimazole, a sufficient amount of an excipient base powder, and a sufficient amount of xylitol; and (ii) applying the compounded composition to the skin of the subject.

In an aspect, a subject can be diagnosed with or can be suspected of having a bacterial infection or a fungal infection or both that affects the subject's skin. In an aspect, the subject can have diabetes, can be obese, can be immuno-compromised, can be non-ambulatory, or can have poor blood flow, or a combination thereof. In an aspect, the subject can routinely wear thick socks or wear heavy boots.

In an aspect, preparing a compounded composition can comprise mixing a disclosed dry formulation with a diluent in a mixing container and agitating the containers of the mixing container to generate a homogenous compounded composition (i.e., a compounded solution or suspension). Methods of preparing a disclosed compounded composition are discussed supra. Diluents are known to the art. In an aspect, a diluent can be a hydrocortisone/acetic acid otic solution. In an aspect, a diluent can be a sodium chloride solution. Mixing containers are known to the art and discussed herein. In an aspect, a disclosed method can comprise cleaning and drying a mixing container.

In an aspect, a disclosed method can comprise orally administering to the subject a pharmaceutical composition comprising one or more active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method can comprise pre-treating the subject's hands or the subject's skin. In an aspect, a subject can apply a liquid skin cleanser (e.g., Hibiclens) to his hands or to the affected portion of the skin. Using water, the subject can wash his hands or the affected portion of the skin with the Hibiclens for at least 5 seconds, at least 10 seconds, at least 15 seconds, at least 20 seconds, or at least 30 seconds.

In an aspect, a disclosed method can comprise repeating the applying step until the bacterial infection, suspected bacterial infection, the fungal infection, or the suspected fungal infection is eradicated or appears to be eradicated. In an aspect, a disclosed method can comprise repeating the applying step twice daily until the bacterial infection, suspected bacterial infection, the fungal infection, or the suspected fungal infection is eradicated or appears to be eradicated. In an aspect, a disclosed method can comprise repeating the applying step twice daily for a pre-determined amount of time. In an aspect, the pre-determined amount of time can comprise at least 5 days, at least 7 days, at least 10 days, at least 14 days, at least 15 days, at least 21 days, at least 30 days, or more than 30 days. In an aspect, the pre-determined amount can comprise an amount of time lasting at least 5-7 days, at least 7-10 days, at least 10-14 days, at least 14-21 days, at least 21-30 days, such as 15 days, at least 30 days, such as 30 days, or more than 30 days.

In an aspect, applying the compounded composition can comprise contacting the compounded composition with at least a portion of the subject's skin until the compounded composition has been absorbed or substantially absorbed by the skin. In an aspect, applying can comprise using a sterile applicator to contact the compounded composition with the skin. In an aspect, a disclosed compounded composition can be applied to skin in conjunction with an occlusive dressing. In an aspect, a disclosed method can comprise applying a covering to the skin affected by the infection.

In an aspect, a disclosed compounded composition can be applied to the subject's skin as a liquid or as an ointment. In an aspect, a disclosed compounded composition can be applied to the subject's skin as a cream, or lotion, or emulsion, or gel.

In an aspect, a disclosed method of treating or preventing an infection can comprise modifying one or more aspects of the disclosed method. For example, in an aspect, a disclosed method can comprise changing or altering the amount of the disclosed compounded composition applied to a subject's skin, or by changing the frequency of the subject's use of the compounded composition, or by changing the duration of time that the subject uses the compounded composition, or by substituting one compounded composition for another compounded composition, or a combination thereof.

L. Methods of Treating or Preventing a Foot Infection

Disclosed herein is a method of treating or preventing a foot infection, the method comprising: (i) adding a dry formulation to water contained within a foot bath; (ii) adding a diluent to the water contained within the foot bath; (iii) agitating the water contained within the foot bath; and (iv) contacting the agitated water with at least a part of one or both feet of a subject.

Disclosed herein is a method of treating or preventing a foot infection, the method comprising: (i) agitating water contained within a foot bath; (ii) adding a dry formulation to the water contained with the foot bath; (iii) adding a diluent to the water contained within the foot bath; and (iv) contacting the agitated water with at least a part of one or both feet of a subject.

Disclosed herein is a method of treating or preventing a foot infection, the method comprising: (i) mixing a dry formulation with a diluent to create a compounded composition; (ii) adding the compounded composition to the water contained within the foot bath; (iii) agitating the water contained within the foot bath; and (iv) contacting the agitated water with at least part of one or both feet of a subject.

Disclosed herein is a method of treating or preventing a foot infection, the method comprising: (i) mixing a dry formulation with a diluent to create a compounded composition; (ii) agitating water contained within a foot bath; (iii) adding the compounded composition to the water contained within the foot bath; and (iv) contacting the agitated water with at least part of one or both feet of a subject.

Disclosed herein is a method of treating or preventing a foot infection, the method comprising: (i) adding a dry formulation to water contained within a foot bath; (ii) adding a diluent to the water contained within the foot bath; (iii) agitating the water contained within the foot bath; and (iv) contacting the agitated water with at least a part of one or both feet of a subject.

Disclosed herein is a method of treating or preventing a foot infection, the method comprising: (i) agitating water contained within a foot bath; (ii) adding a dry formulation to the water contained with the foot bath; (iii) adding a diluent to the water contained within the foot bath; and (iv) contacting the agitated water with at least a part of one or both feet of a subject.

Disclosed herein is a method of treating or preventing a foot infection, the method comprising: (i) adding a dry formulation to water contained within a foot bath; (ii) agitating the water contained within the foot bath; and (iii) contacting the agitated water with at least a part of one or both feet of a subject.

Disclosed herein is a method of treating or preventing a foot infection, the method comprising: (i) agitating water contained within a foot bath; (ii) adding a dry formulation to the water contained with the foot bath; and (iii) contacting the agitated water with at least a part of one or both feet of a subject.

Dry formulations are discussed supra. In an aspect, a disclosed dry formulation can comprise (1) a therapeutically effective amount of mupirocin, therapeutically effective amount of an anti-bacterial agent, and a therapeutically effective amount of an anti-fungal agent, (2) a therapeutically effective amount of mupirocin, a therapeutically effective amount of clindamycin hydrochloride, and a therapeutically effective amount of clotrimazole, (3) a therapeutically effective amount of mupirocin, a therapeutically effective amount of a corticosteroid or a pharmaceutically acceptable salt thereof, and an anti-fungal agent, (4) a therapeutically effective amount of mupirocin, a therapeutically effective amount of betamethasone sodium phosphate, and a therapeutically effective amount of clotrimazole, (5) a therapeutically effective amount of clotrimazole and a sufficient amount of an excipient base powder, (6) a therapeutically effective amount of clotrimazole, a sufficient amount of an excipient base powder, and a sufficient amount of xylitol, (7) a therapeutically effective amount of clotrimazole, a sufficient amount of an excipient base powder, a sufficient amount of xylitol, and a therapeutically effective amount of ceftriaxone, (8) a therapeutically effective amount of clotrimazole, a therapeutically effective amount of a corticosteroid or a pharmaceutically acceptable salt thereof, a sufficient amount of an excipient base powder, and a sufficient amount of xylitol, (9) a therapeutically effective amount of clotrimazole, a therapeutically effective amount of a betamethasone sodium phosphate, a sufficient amount of an excipient base powder, and a sufficient amount of xylitol, (10) a therapeutically effective amount of doxycycline or a pharmaceutically acceptable salt thereof, a therapeutically effective amount of a corticosteroid or a pharmaceutically acceptable salt thereof, and a therapeutically effective amount of an anti-fungal agent, (11) a therapeutically effective amount of doxycycline hyclate, a therapeutically effective amount of betamethasone sodium phosphate, and a therapeutically effective amount of clotrimazole, and (12) a therapeutically effective amount of doxycycline hyclate, a therapeutically effective amount of a dexamethasone, and a therapeutically effective amount of clotrimazole.

In an aspect, a disclosed dry formulation can comprise (1) a therapeutically effective amount of azithromycin, a therapeutically effective amount of fluticasone, and a therapeutically effective amount of fluconazole, (2) a therapeutically effective amount of azithromycin, a therapeutically effective amount of fluticasone, a therapeutically effective amount of fluconazole, a sufficient amount of an excipient base powder, and a sufficient amount of xylitol, (3) a therapeutically effective amount of sulfamethoxazole, a therapeutically effective amount of trimethoprim, a therapeutically effective amount of fluticasone, and a therapeutically effective amount of fluconazole, (4) a therapeutically effective amount of sulfamethoxazole, a therapeutically effective amount of trimethoprim, a therapeutically effective amount of fluticasone, a therapeutically effective amount of fluconazole, a sufficient amount of an excipient base powder, and a sufficient amount of xylitol, (5) a therapeutically effective amount of levofloxacin hemihydrate, a therapeutically effective amount of fluticasone, and a therapeutically effective amount of fluconazole, (6) a therapeutically effective amount of levofloxacin hemihydrate, a therapeutically effective amount of fluticasone, a therapeutically effective amount of fluconazole, a sufficient amount of an excipient base powder, and a sufficient amount of xylitol, (7) a therapeutically effective amount of fluticasone and a therapeutically effective amount of fluconazole, (8) a therapeutically effective amount of fluticasone, a therapeutically effective amount of fluconazole, a sufficient amount of an excipient base powder, and a sufficient amount of xylitol, (9) a therapeutically effective amount of vancomycin hydrochloride and a therapeutically effective amount of mupirocin, (10) a therapeutically effective amount of vancomycin hydrochloride, a therapeutically effective amount of mupirocin, a sufficient amount of an excipient base powder, and a sufficient amount of xylitol, (11) a therapeutically effective amount of mupirocin and a therapeutically effective amount of clotrimazole, (12) a therapeutically effective amount of mupirocin, a therapeutically effective amount of clotrimazole, a sufficient amount of an excipient base powder, and a sufficient amount of xylitol, (13) a therapeutically effective amount of mupirocin, a therapeutically effective amount of clindamycin, and a therapeutically effective amount of clotrimazole, (14) a therapeutically effective amount of mupirocin, a therapeutically effective amount of clindamycin or a pharmaceutically acceptable salt thereof, a therapeutically effective amount of clotrimazole, a sufficient amount of an excipient base powder, and a sufficient amount of xylitol, (15) a therapeutically effective amount of ceftriaxone, (16) a therapeutically effective amount of ceftriaxone, a sufficient amount of an excipient base powder, and a sufficient amount of xylitol, (17) a therapeutically effective amount of clotrimazole, (18) a therapeutically effective amount of clotrimazole, a sufficient amount of an excipient base powder, and a sufficient amount of xylitol, (19) a therapeutically effective amount of doxycycline or a pharmaceutically acceptable salt thereof and a therapeutically effective amount of clotrimazole, and (20) a therapeutically effective amount of doxycycline or a pharmaceutically acceptable salt thereof, a therapeutically effective amount of clotrimazole, a sufficient amount of an excipient base powder, and a sufficient amount of xylitol.

In an aspect, the subject can have diabetes, can be obese, can be immunocompromised, can be non-ambulatory, or can have poor blood flow, or a combination thereof. In an aspect, the subject can routinely wear thick socks or wear heavy boots. In an aspect, a subject can be diagnosed with or can be suspected of having a bacterial infection or a fungal infection or both that affects one or both of the subject's feet. In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

In an aspect, adding a disclosed dry formulation to the water contained within a foot bath can comprise adding to the water between about 1 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg, about 100 mg to about 200 mg, or about 200 mg to about 2000 mg of a disclosed dry formulation. Foot baths are known to the art and are discussed supra. In an aspect, adding a disclosed dry formulation to the water contained within a foot bath can comprise adding to the water about 1 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed dry formulation.

In an aspect, adding a disclosed dry formulation to the water contained within a foot bath can comprise adding to the water the contents of one capsule comprising a disclosed dry formulation. In an aspect, adding a disclosed dry formulation to the water contained within a foot bath can comprise adding to the water the contents of one or more capsules, each comprising a disclosed dry formulation. Capsules comprising a disclosed dry formulation are described supra.

In an aspect, a disclosed method can comprise adding the diluent to the water contained in the foot bath. In an aspect, the amount of diluent can be about 1 mL, 2 mL, 3 mL, 4 mL, 5 mL, 6 mL, 7 mL, 8 mL, 9 mL, or 10 mL, or from about 1 mL to about 5 mL, or from about 5 mL to about 10 mL, or from about 10 mL to about 20 mL, or from about 20 mL to 30 mL, or from about 30 mL to about 40 mL, or from about 40 mL to about 50 mL, or from about 50 mL to about 100 mL, or more than 100 mL.

In an aspect, adding a disclosed dry formulation to the mixing container can comprise adding to the mixing container between about 1 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg, about 100 mg to about 200 mg, or about 200 mg to about 2000 mg of a disclosed dry formulation. Mixing containers are known to the art and are discussed supra. In an aspect, adding a disclosed dry formulation to the mixing container can comprise adding to the water about 1 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed dry formulation.

In an aspect, adding a disclosed dry formulation to the mixing container can comprise adding to the mixing container the contents of one capsule comprising a disclosed dry formulation. In an aspect, adding a disclosed dry formulation to the mixing container can comprise adding to the mixing container the contents of one or more capsules, each comprising a disclosed dry formulation. Capsules comprising a disclosed dry formulation are described supra.

In an aspect, a disclosed dry formulation and a diluent can be added to a mixing container and the contents of the mixing container can be agitated to generate a homogenous compounded composition (i.e., a compounded solution or suspension). Diluents are known to the art and are discussed supra. In an aspect, a diluent can comprise a hydrocortisone/ acetic acid otic solution. In an aspect, a diluent can comprise a sodium chloride solution. In an aspect, a disclosed method can comprise adding the diluent to the mixing container. In an aspect, the amount of diluent can be about 1 mL, 2 mL, 3 mL, 4 mL, 5 mL, 6 mL, 7 mL, 8 mL, 9 mL, or 10 mL, or from about 1 mL to about 5 mL, or from about 5 mL to about 10 mL, or from about 10 mL to about 20 mL, or from about 20 mL to 30 mL, or from about 30 mL to about 40 mL, or from about 40 mL to about 50 mL, or from about 50 mL to about 100 mL, or more than 100 mL.

In an aspect, the compounded composition can be added to the water contained in the foot bath. In an aspect, the amount of a disclosed compounded composition can be about 1 mL, 2 mL, 3 mL, 4 mL, 5 mL, 6 mL, 7 mL, 8 mL, 9 mL, or 10 mL, or from about 1 mL to about 5 mL, or from about 5 mL to about 10 mL, or from about 10 mL to about 20 mL, or from about 20 mL to 30 mL, or from about 30 mL to about 40 mL, or from about 40 mL to about 50 mL, or from about 50 mL to about 100 mL, or more than 100 mL.

In an aspect, a disclosed dry formulation can be added to the water contained within the foot bath while the water is being heated. In an aspect, a disclosed dry formulation can be added to the water contained within the foot bath while the water is being agitated. In an aspect, a disclosed compounded composition can be added to the water contained within the foot bath while the water is being heated. In an aspect, a disclosed compounded composition can be added to the water contained within the foot bath while the water is being agitated. In an aspect, a disclosed diluent can be added to the water contained within the foot bath while the water is being heated. In an aspect, a disclosed diluent can be added to the water contained within the foot bath while the water is being agitated.

In an aspect, a disclosed method can comprise heating the water contained within the foot bath. In an aspect, a disclosed method can comprise agitating the water contained within the foot bath. In an aspect, a foot bath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the foot bath. Motors and agitators are known to the art. In an aspect, mechanical agitation can serve to distribute the dry formulation, the diluent, or the compounded composition throughout the water contained within the foot bath. In an aspect, agitation can ensure dissolution of the disclosed dry formulation or the dissolution of the compounded composition throughout the water. Heating agents and/or means to heat water in a compartment are known to the art. In an aspect, agitation can ensure optimal contact of a disclosed dry formulation or a disclosed compounded composition.

In an aspect, a disclosed method can comprise repeating daily steps (i)-(iii) or steps (i)-(iv). In an aspect, a disclosed method can comprise repeating daily steps (i)-(iii) or steps (i)-(iv) until the bacterial infection, suspected bacterial infection, the fungal infection, or the suspected fungal infection is eradicated or appears to be eradicated. In an aspect, a disclosed method can comprise repeating twice daily the applying step for a pre-determined amount of time. In an aspect, the pre-determined amount of time can comprise at least 5 days, at least 7 days, at least 10 days, at least 14 days, at least 15 days, at least 21 days, at least 30 days, or more than 30 days. In an aspect, the pre-determined amount can comprise an amount of time lasting at least 5-7 days, at least 7-10 days, at least 10-14 days, at least 14-21 days, at least 21-30 days, such as 15 days, at least 30 days, such as 30 days, or more than 30 days.

In an aspect, contacting can comprise placing at least part of one or both feet of the subject in the foot bath. In an aspect, contacting can comprise placing at least part of one or both feet of the subject in the foot bath for about 5 to about 15 minutes. In an aspect, contacting can comprise placing at least part of one or both feet of the subject in the foot bath for about 10 minutes.

In an aspect, the method can comprise removing the disclosed dry formulation from a container, such as, for example, a tube, a packet, a capsule, a syringe, a dropper, a vial, etc., prior to adding the disclosed dry formulation to the water. In an aspect, the method can comprise removing the disclosed dry formulation from a container, such as, for example, a tube, a packet, a capsule, a syringe, a dropper, a vial, etc., prior to adding the disclosed dry formulation to the diluent.

In an aspect, the method can comprise removing the disclosed compounded composition from a container, such as, for example, a tube, a packet, a capsule, a syringe, a dropper, a vial, etc., prior to adding the disclosed compounded composition to the water.

In an aspect, a disclosed method can comprise emptying the water from the foot bath. In an aspect, a disclosed method can comprise cleaning the foot bath. In an aspect, a disclosed method can comprise drying the foot bath.

In an aspect, a disclosed method can comprise orally administering to the subject a pharmaceutical composition comprising one or more active agents. Additional active agents are known to the art and are discussed supra. Additional active agents include, but are not limited to, the following: anti-infective agents (e.g., anti-bacterial agents, anti-fungal agents, combinations thereof), corticosteroids, antihistamines, anticholinergics, mucolytics, leukotriene receptors antagonists, etc., pharmaceutically acceptable salts thereof, or combinations thereof.

In an aspect, a disclosed method of treating or preventing a foot infection can comprise modifying one or more aspects of the disclosed method. For example, in an aspect, a method can be altered by changing the amount of a disclosed dry formulation or a disclosed compounded composition added to a foot bath, by changing the frequency of the subject's use of the foot bath, or by changing the duration of time that the subject's foot or feet contact the water contained within the foot bath, or by substituting one disclosed dry formulation for another disclosed dry formulation or one disclosed compounded composition for another disclosed compounded composition, or a combination thereof.

In an aspect, a disclosed method can comprise preparing a disclosed dry formulation. Methods of preparing a disclosed dry formulation are discussed supra. In an aspect, a disclosed method can comprise preparing a disclosed compounded composition. Methods of preparing a disclosed compounded composition are discussed supra.

M. Expected Efficacy of Various Anti-Infective Agents

Table 1 shows the expected efficacy of anti-fungal agents against various fungi.

Tables 2 and 3 show the expected efficacy of anti-bacterial agents against various bacteria.

TABLE 1

EFFICACY OF VARIOUS ANTIFUNGAL AGENTS

| | Fluconazole | Itraconazole | Voriconazole | Amphotericin | Nystatin |
|---|---|---|---|---|---|
| *Aspergillus flavus* | yes | yes | yes | yes | |
| *Aspergillus fumigatus* | yes | yes | yes | yes | |
| *Aspergillus niger* | | | yes | yes | |
| *Aspergillus terreus* | | | yes | yes | |
| *Blastomyces dermatitidis* | yes | yes | | yes | |
| *Candida* species | yes | yes | yes | yes | yes |
| *Coccidioides immitis* | yes | yes | | yes | |
| *Cryptococcus neoformans* | yes | yes | | yes | |
| *Fusarium* species | | | yes | | |
| *Histoplasma capsulatum* | yes | | | yes | |
| *Histoplasma duboisii* | | yes | | | |
| *Leishmania donovani* | | | | yes | |
| *Leishmania infantum* | | | | yes | |
| *Paracoccidioides brasiliensis* | | yes | | yes | |
| *Scedosporium apiospermum* | | | yes | | |
| *Sporothrix schenckii* | | yes | | | |
| *Trichophyton mentagrophytes* | | yes | | | |
| *Trichophyton rubrum* | | yes | | | |

TABLE 2

EFFICACY OF VARIOUS ANTIBIOTIC AGENTS

| | Gram | Bactroban | Ceftriaxone | Vancomycin | Colistimethate | Ciprofloxacin |
|---|---|---|---|---|---|---|
| *Bacteroides fragilis* | anaer | | yes | no | no | no |
| *Clostridium difficile* | anaer | | no | yes | no | no |
| *Clostridium perfringens* | anaer | no | yes | no | | |
| *Chlamydia pneumoniae* | n/a | | no | no | no | yes |
| *Chlamydia psittaci* | n/a | | no | no | no | |
| *Chlamydia trachomatis* | n/a | | no | no | no | |
| *Mycoplasma pneumoniae* | n/a | | no | no | no | yes |
| *Acinetobacter baumannii* | neg | no | no | no | ± | ± |
| *Acinetobacter calcoaceticus* | neg | no | no | no | ± | ± |
| *Acinetobacter lwoffii* | neg | no | no | no | ± | ± |
| *Bartonella bacilliformis* | neg | no | ± | no | | yes |
| *Bordetella pertussis* | neg | no | no | no | no | ± |
| *Brucella* species | neg | no | ± | no | no | ± |
| *Campylobacter jejuni* | neg | no | no | no | | yes |
| *Citrobacter diversus* | neg | no | yes | no | | yes |
| *Citrobacter freundii* | neg | no | yes | no | | yes |
| *Enterobacter aerogenes* | neg | no | yes | no | yes | yes |
| *Enterobacter cloacae* | neg | no | yes | no | yes | yes |
| *Enterobacter sakazakii* | neg | no | yes | no | yes | |
| *Escherichia coli* | neg | no | yes | no | yes | yes |
| *Francisella tularensis* | neg | no | no | no | | yes |
| *Haemophilus ducreyi* | neg | | yes | no | | |
| *Haemophilus influenzae* | neg | no | yes | no | | yes |
| *Haemophilus parainfluenzae* | neg | | yes | no | no | yes |
| *Klebsiella* (*Calymmato-bacterium*) | neg | no | yes | no | yes | |
| *Klebsiella oxytoca* | neg | no | yes | no | yes | yes |
| *Klebsiella pneumoniae* | neg | no | yes | no | yes | yes |
| *Legionella pneumophila* | neg | no | no | no | no | yes |
| *Moraxella catarrhalis* | neg | no | yes | no | no | yes |
| *Morganella morganii* | neg | no | yes | no | yes | |
| *Neisseria gonorrhoeae* | neg | no | yes | no | no | yes |
| *Neisseria meningitidis* | neg | no | yes | no | no | yes |
| *Proteus mirabilis* | neg | no | yes | no | no | yes |
| *Proteus vulgaris* | neg | no | yes | no | no | yes |
| *Providencia rettgeri* | neg | no | yes | no | no | yes |
| *Providencia stuartii* | neg | no | yes | no | no | yes |
| *Pseudomonas aeruginosa* | neg | no | no | no | yes | yes |
| *Pseudomonas fluorescens* | neg | no | ± | no | yes | yes |
| *Rickettsiae* | neg | no | no | no | | yes |
| *Salmonella typhi* | neg | no | yes | no | | yes |
| *Serratia marcescens* | neg | no | yes | no | no | yes |
| *Shigella boydii* | neg | no | yes | no | | yes |
| *Shigella dysenteriae* | neg | no | yes | no | | yes |
| *Shigella flexneri* | neg | no | yes | no | | yes |
| *Shigella sonnei* | neg | no | yes | no | | yes |
| *Vibrio cholerae* | neg | no | no | no | no | yes |
| *Yersinia pestis* | neg | no | no | no | | yes |

TABLE 2-continued

EFFICACY OF VARIOUS ANTIBIOTIC AGENTS

|  | Gram | Bactroban | Ceftriaxone | Vancomycin | Colistimethate | Ciprofloxacin |
|---|---|---|---|---|---|---|
| *Corynebacterium jeikeium* | pos | no | no | yes | no | no |
| *Corynebacterium urealyticum* | pos | no | no | yes | no | ± |
| *Diphtheroids* | pos |  | no | yes | no |  |
| *Enterococcus faecalis* | pos |  | no | yes | no | ± |
| *Enterococcus faecium* | pos |  | no | yes, not VRE | no | no |
| Methicillin resistant *staph aureus* (MRSA) | pos | yes | no | yes | no | no |
| *Peptostreptococcus* | pos |  | yes | yes | no | ± |
| *Staphylococcus aureus* (MSSA) | pos | yes | yes | yes | no | ± |
| *Staphylococcus epidermidis* | pos |  | yes | yes | no | yes |
| *Streptococcus agalactiae* | pos |  | yes | yes | no | ± |
| *Streptococcus pneumoniae* | pos |  | yes | yes | no | ± |
| *Streptococcus pyogenes* | pos | yes | yes | yes | no | ± |
| Viridans group streptococci | pos |  | yes | yes | no | ± |

TABLE 3

EFFICACY OF VARIOUS ANTIBIOTIC AGENTS

|  | Levofloxacin | Tobramycin | Doxycycline | Azithromycin | Clindamycin | Sulfa/Trim |
|---|---|---|---|---|---|---|
| *Bacteroides fragilis* | no | no | ± | no | yes | no |
| *Clostridium difficile* | no | no | ± | no | ± | no |
| *Clostridium perfringens* | yes | no |  | no | yes—partial | no |
| *Chlamydia pneumoniae* | yes | no | yes | yes | ± | no |
| *Chlamydia psittaci* |  | no | yes | yes | no | no |
| *Chlamydia trachomatis* |  | no | yes | yes | no | no |
| *Mycoplasma pneumoniae* | yes | no | ± | yes | no | no |
| *Acinetobacter baumannii* | ± | no | no | no | no | ± |
| *Acinetobacter calcoaceticus* | ± | no | ± | no | no | ± |
| *Acinetobacter lwoffii* | ± | no | no | no | no | ± |
| *Bartonella bacilliformis* | yes | ± | yes | yes | no | yes |
| *Bordetella pertussis* | ± | no | yes | no | yes |  |
| *Brucella* species | ± | ± | yes | no | no | yes |
| *Campylobacter jejuni* | yes | yes | yes | yes | no | no |
| *Citrobacter diversus* | yes | yes | no | no | no | no |
| *Citrobacter freundii* | yes | yes | no | no | no | no |
| *Enterobacter aerogenes* | yes | yes | ± | no | no | yes |
| *Enterobacter cloacae* | yes | yes | ± | no | no | yes |
| *Enterobacter sakazakii* | yes | yes | ± | no | no | no |
| *Escherichia coli* | yes | yes | ± | no | no | yes |
| *Francisella tularensis* | yes | ± | yes | no | no | no |
| *Haemophilus ducreyi* |  | yes | yes |  |  | ± |
| *Haemophilus influenzae* | yes | yes | yes | yes | no | ± |
| *Haemophilus parainfluenzae* | yes |  | yes |  | no | no |
| *Klebsiella* (*Calymmatobacterium*) |  | yes | yes | no |  | yes |
| *Klebsiella oxytoca* | yes | yes | ± | no | no | yes |
| *Klebsiella pneumoniae* | yes | yes | ± | no | no | yes |
| *Legionella pneumophila* | yes | no | yes | yes | no | no |
| *Moraxella catarrhalis* | yes | yes | yes | yes | no | yes |
| *Morganella morganii* | yes | ± | no | no | no | yes |
| *Neisseria gonorrhoeae* | yes | no | ± | ± | no | ± |
| *Neisseria meningitidis* | yes | no | yes | yes | no | yes |
| *Proteus mirabilis* | yes | yes | no | no | no | no |
| *Proteus vulgaris* | yes | yes | no | no | no | no |
| *Providencia rettgeri* | yes | ± | no | no | no | ± |
| *Providencia stuartii* | yes | ± | no | no | no | ± |
| *Pseudomonas aeruginosa* | yes | yes | no | no | no | no |
| *Pseudomonas fluorescens* | yes | yes |  | no | no | ± |
| *Rickettsiae* | yes |  | yes | yes | no | no |
| *Salmonella typhi* | yes |  | ± | ± | no | ± |
| *Serratia marcescens* | yes | yes | no | no | no | ± |
| *Shigella boydii* | yes | yes | ± | ± | no | ± |
| *Shigella dysenteriae* | yes | yes | ± | ± | no | ± |
| *Shigella flexneri* | yes | yes | ± | ± | no | ± |
| *Shigella sonnei* | yes | yes | ± | ± | no | ± |
| *Vibrio cholerae* | yes | no | yes | yes | no | yes |
| *Yersinia pestis* | yes | yes | yes | ± | no | yes |
| *Corynebacterium jeikeium* | no | no |  | no |  |  |
| *Corynebacterium urealyticum* | ± | no | ± | ± |  | no |
| *Diphtheroids* |  | no |  |  |  |  |

TABLE 3-continued

EFFICACY OF VARIOUS ANTIBIOTIC AGENTS

|  | Levofloxacin | Tobramycin | Doxycycline | Azithromycin | Clindamycin | Sulfa/Trim |
|---|---|---|---|---|---|---|
| *Enterococcus faecalis* | yes | no | no | no | no | no |
| *Enterococcus faecium* | no | no | no | no | no | ± |
| Methicillin resistant *staph aureus* (MRSA) | no | no | ± | no | no | yes |
| *Peptostreptococcus* | ± | no | ± | ± | yes | yes |
| Staphylococcus aureus (MSSA) | yes | no | ± | yes | yes | yes |
| *Staphylococcus epidermidis* | yes | no | yes | yes | yes | yes |
| *Streptococcus agalactiae* | yes | no | ± | yes | yes | yes |
| *Streptococcus pneumoniae* | yes | no | yes | yes | yes | yes |
| *Streptococcus pyogenes* | yes | no | ± | yes | yes | ± |
| Viridans group streptococci | yes | no | ± | ± | yes | yes |

What is claimed is:

1. A method of making a compounded composition, the method comprising mixing doxycycline hyclate and a diluent, wherein the diluent comprises a hydrocortisone/acetic acid otic solution.

2. A compounded composition comprising:
mupirocin, clindamycin hydrochloride, xylitol, clotrimazole, and a diluent, wherein the diluent comprises at least one of (a) hydrocortisone/acetic acid otic solution or (b) sodium chloride solution.

3. The compounded composition of claim 2, wherein mupirocin and clindamycin hydrochloride are present in the compounded composition at ratio from about 1:1 to about 1:2.

4. The compound composition of claim 3, wherein the ratio of mupirocin to clindamycin hydrochloride is about 1:1.25.

5. The compounded composition of claim 2, wherein mupirocin and clotrimazole are present in the compounded composition at a ratio from about 1:0.05 to about 1:0.3.

6. The compounded composition of claim 5, wherein the ratio of mupirocin to clotrimazole is about 1:0.15.

7. The compounded composition of claim 2, wherein clindamycin hydrochloride and clotrimazole are present in the compounded composition at a ratio from about 1:0.1 to about 1:0.3.

8. The compounded composition of claim 7, wherein the ratio of clindamycin hydrochloride to clotrimazole is about 1:0.12.

9. The compounded composition of claim 2, wherein the compounded composition comprises a ratio from about 1:1 to about 1:2 mupirocin to clindamycin hydrochloride, a ratio from about 1:0.05 to about 1:0.3 mupirocin to clotrimazole, and a ratio from about 1:0.1 to about 1:0.3 clindamycin hydrochloride to clotrimazole.

10. The compounded composition of claim 9, wherein the compounded composition comprises about 20 mg mupirocin, about 25 mg clindamycin hydrochloride, and about 3 mg clotrimazole.

\* \* \* \* \*